(12) United States Patent
Laurence et al.

(10) Patent No.: US 12,053,614 B2
(45) Date of Patent: Aug. 6, 2024

(54) SYSTEMS AND METHODS FOR CONTROLLED DRUG DELIVERY PUMPS

(71) Applicant: UNL Holdings LLC, New York, NY (US)

(72) Inventors: Lawton Laurence, Phoenixville, PA (US); Ian B. Hanson, Wayne, PA (US); Paul F. Bente, IV, Wayne, PA (US); Robert Trzybinski, Chester Springs, PA (US)

(73) Assignee: UNL HOLDINGS LLC, New York, NY (US)

( * ) Notice: Subject to any disclaimer, the term of this patent is extended or adjusted under 35 U.S.C. 154(b) by 0 days.

(21) Appl. No.: 15/780,137

(22) PCT Filed: Dec. 2, 2016

(86) PCT No.: PCT/IB2016/001835
§ 371 (c)(1),
(2) Date: May 30, 2018

(87) PCT Pub. No.: WO2017/093803
PCT Pub. Date: Jun. 8, 2017

(65) Prior Publication Data
US 2018/0353682 A1 Dec. 13, 2018

Related U.S. Application Data

(60) Provisional application No. 62/262,683, filed on Dec. 3, 2015.

(51) Int. Cl.
*A61M 5/172* (2006.01)
*A61M 5/142* (2006.01)
(Continued)

(52) U.S. Cl.
CPC ............ *A61M 5/172* (2013.01); *A61M 5/142* (2013.01); *A61M 5/14244* (2013.01);
(Continued)

(58) Field of Classification Search
CPC .... A61M 2005/14208; A61M 5/14244; A61M 5/145; A61M 5/172
See application file for complete search history.

(56) References Cited

U.S. PATENT DOCUMENTS 8,109,921 B2   2/2012   Estes et al.
8,192,394 B2   6/2012   Estes et al.
(Continued)

FOREIGN PATENT DOCUMENTS

CN   101868273 A   10/2010
CN   102149416 A   8/2011
(Continued)

OTHER PUBLICATIONS

International Search Report for International Search Report for International Application No. PCT/IB2016/001835, "Systems and Methods for Controlled Drug Delnery Pumps", Date of Mailing: Apr. 27, 2017.
(Continued)

*Primary Examiner* — Phillip A Gray
*Assistant Examiner* — Anna E Goldberg-Richmeier
(74) *Attorney, Agent, or Firm* — MARSHALL, GERSTEIN & BORUN LLP

(57) ABSTRACT

Power and control systems for a drug delivery device allow for the activation, control of, and communication with the drug delivery device. The power and control system allows for a delay between device activation, and optionally needle insertion, and commencing drug delivery. The delay may be for a predetermined time. In addition, the power and control system may communicate with one or more external sensors
(Continued)

and devices. The inputs from the sensors and devices may automatically, or on demand, adjust the delivery parameters of the device. The power and control systems may control a drive system that delivers a fluid at a variable rate or profile, allowing for the delivery to be tailored to maximize the effectiveness of the treatment.

20 Claims, 26 Drawing Sheets

(51) Int. Cl.
- *A61M 5/315* (2006.01)
- *G16H 20/17* (2018.01)
- *G16H 40/63* (2018.01)
- *A61M 5/14* (2006.01)
- *A61M 5/168* (2006.01)

(52) U.S. Cl.
CPC ............ *A61M 5/315* (2013.01); *G16H 20/17* (2018.01); *G16H 40/63* (2018.01); *A61M 5/14* (2013.01); *A61M 5/168* (2013.01)

(56) References Cited

U.S. PATENT DOCUMENTS

| | | | |
|---|---|---|---|
| 9,061,097 B2 | 6/2015 | Holt et al. | |
| 9,066,694 B2 | 6/2015 | Say et al. | |
| 9,173,997 B2* | 11/2015 | Gross ................ | A61M 5/31596 |
| 9,463,280 B2* | 10/2016 | Cabiri ............... | A61M 5/14248 |
| 2008/0300572 A1 | 12/2008 | Rankers et al. | |
| 2009/0028824 A1* | 1/2009 | Chiang .................. | A61P 43/00 |
| | | | 424/85.7 |
| 2010/0168683 A1* | 7/2010 | Cabiri ............... | A61M 5/14248 |
| | | | 604/263 |
| 2010/0228186 A1 | 9/2010 | Estes et al. | |
| 2011/0166512 A1* | 7/2011 | Both ................. | A61M 5/14248 |
| | | | 604/152 |
| 2011/0178472 A1* | 7/2011 | Cabiri ................... | A61M 5/158 |
| | | | 604/198 |
| 2013/0237916 A1* | 9/2013 | Hanson ..................... | A61L 2/00 |
| | | | 604/151 |
| 2013/0253472 A1 | 9/2013 | Cabiri | |
| 2013/0303980 A1 | 11/2013 | Talbot et al. | |
| 2014/0200510 A1 | 7/2014 | Agard et al. | |
| 2016/0296699 A1* | 10/2016 | Cabiri ..................... | A61M 5/20 |
| 2017/0258987 A1* | 9/2017 | Caspers ............... | G06F 1/1613 |
| 2017/0258994 A1* | 9/2017 | Schiendzielorz . | A61M 5/14248 |

FOREIGN PATENT DOCUMENTS

| | | |
|---|---|---|
| CN | 104321093 A | 1/2015 |
| CN | 108472437 A | 8/2018 |
| JP | 2013070863 A | 4/2013 |
| JP | 2014531922 A | 12/2014 |
| WO | 2007035567 A2 | 3/2007 |
| WO | WO 2011/156373 A1 | 12/2011 |
| WO | WO 2013/115843 A1 | 8/2013 |
| WO | 2013134279 A1 | 9/2013 |

OTHER PUBLICATIONS

Written Opinion of the International Searching Authority for International Application No. PCT/IB2016/001835, "Systems and Methods for Controlled Drug Delnery Pumps", Date of Mailing: Apr. 27, 2017.

International Preliminary Report on Patentability for International Application No. PCT/IB2016/001835, entitled: "Systems and Methods for Controlled Drug Delivery Pumps," 9 pages, mailed Jun. 14, 2018.

Japanese Patent Application No. 2021-189985, Notice of Rejection, mailed Sep. 6, 2022.

* cited by examiner

SYSTEMS AND METHODS FOR CONTROLLED DRUG DELIVERY PUMPS

CROSS-REFERENCE TO RELATED APPLICATIONS

This application is the U.S. National Stage of International Application No. PCT/IB2016/001835, filed Dec. 2, 2016, which designates the U.S., published in English, and claims the benefit of U.S. Provisional Application No. 62/262,683, filed Dec. 3, 2015. The entire teachings of the above applications are incorporated herein by reference.

FIELD

The present invention relates to drug delivery pump devices. Particularly, the present invention relates to systems and sub-systems for drug delivery pumps that control drive mechanisms of the drug pump devices and provide time-controlled delivery of drug substances. The invention further relates to methods of operating such drug delivery pump devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injection pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

SUMMARY

The present invention provides drive mechanisms for the controlled delivery of drug substances, controlled drug delivery pumps with such drive mechanisms, the methods of operating such devices, and the methods of assembling such devices. Notably, the drive mechanisms of the present invention may enable or initiate several functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user. The embodiments of the present invention thus are capable of delivering drug substances at variable rates. The drive mechanisms of the present invention may be pre-configurable or dynamically configurable, such as by control by the power and control system, to meet desired delivery rates or profiles, as explained in detail below. Additionally, the drive mechanisms of the present invention provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. Because the end-of-dose indication is related to the physical end of axial translation and/or travel of one or more components of the drive mechanism, the drive mechanism and drug pump provide a true end-of-dose indication to the user. Through these mechanisms, confirmation of drug dose delivery can accurately be provided to the user or administrator. Accordingly, the devices of the present invention alleviate one or more of the problems associated with prior art devices, such as those referred to above.

In one embodiment, the drug delivery device includes a drug container containing a fluid, a drive system, a power and control system, a timer, and a needle insertion mechanism which may be mechanically activated by a user. In such an embodiment, activation of the needle insertion mechanism causes a cannula to be inserted into a target and also causes the power and control system to enter a delay mode for a predetermined duration which is monitored by the timer and further wherein at the completion of the predetermined duration the power and control system enters a delivery mode in which the power and control system causes the drive system to deliver the fluid from the drug container through the needle insertion mechanism and to a target.

The drug delivery pump may further include a status switch and actuation of the status switch causes the power and control system to enter the delay mode. The status switch may be configured to be actuated by contact with a portion of the needle insertion mechanism after activation of the needle insertion mechanism. The needle insertion mechanism may be a rotational needle insertion mechanism and rotation of a portion of the needle insertion mechanism may cause contact with the status switch.

In at least one embodiment, while in the delay mode the power and control system intermittently enters a communication mode in which the power and control system provides a delay mode indicator. The delay mode indicator may be an audible indication or a visual indication.

In at least one embodiment, the drug delivery device delivers a bolus delivery of the fluid.

In at least one embodiment, the power and control system causes activation of an end-of-delivery indicator at completion of delivery of the fluid.

In at least one embodiment, the drug delivery device includes an on-body sensor configured to detect proximity of the drug delivery device to a target and actuation of the on-body sensor causes activation of the power and control system.

In at least one embodiment, the power and control system causes activation of a needle insertion mechanism (NIM) request notification if the needle insertion mechanism is not activated within a predetermined time after activation of the power and control system.

In at least one embodiment, the power and control system causes activation of a delivery mode indicator upon entering the delivery mode. The delivery mode indicator may be a visual indication or an audible indication.

A method of drug delivery may include the steps of: activation by a user of a needle insertion mechanism, activation of a power and control system to enter a delay mode, at the completion of a predetermined duration, the power and control system entering a delivery mode, the power and control system activating a drive system to deliver a fluid from a drug container, through the needle insertion mechanism and to a target. The method may further include the step of actuating a status switch. The status switch may be actuated by contact with the needle insertion mechanism.

The method may further include the step of, while in the delay mode, the power and control system intermittently entering a communication mode to provide a delay mode indicator.

The method may further include the step of actuating an on-body sensor to cause activation of the power and control system.

The method of may further include the step of the power and control system causing activation of a delivery mode indicator upon entering the delivery mode.

The method may further include the step of the power and control system causing activation of a NIM request notification if the needle insertion mechanism is not activated within a predetermined time after activation of the power and control system.

The method may further include the step of the power and control system causing activation of an end-of-delivery indicator at completion of delivery of the fluid.

In at least one embodiment of the present invention, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present invention, the delivery profile may be adjusted automatically based on one or more inputs. For example, the delivery profile may be adjusted based on the patient's activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/ adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device.

The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of the actuator. The change in the rate of movement of the actuator causes a change in the rotation rate of the regulating mechanism which, in turn, controls the rate of drug delivery to the user. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the user. Accordingly, one or more embodiments of the present invention are capable of producing a change to the rate of medicament delivery from the drug container thereby providing a dynamic control capability to the multi-function drive mechanism and/or the drug delivery device.

Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. For example, the embodiments may include one or more batteries utilized to power the motor, drive mechanisms, and drug pumps of the present invention. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein.

DETAILED DESCRIPTION

Figure 1A:
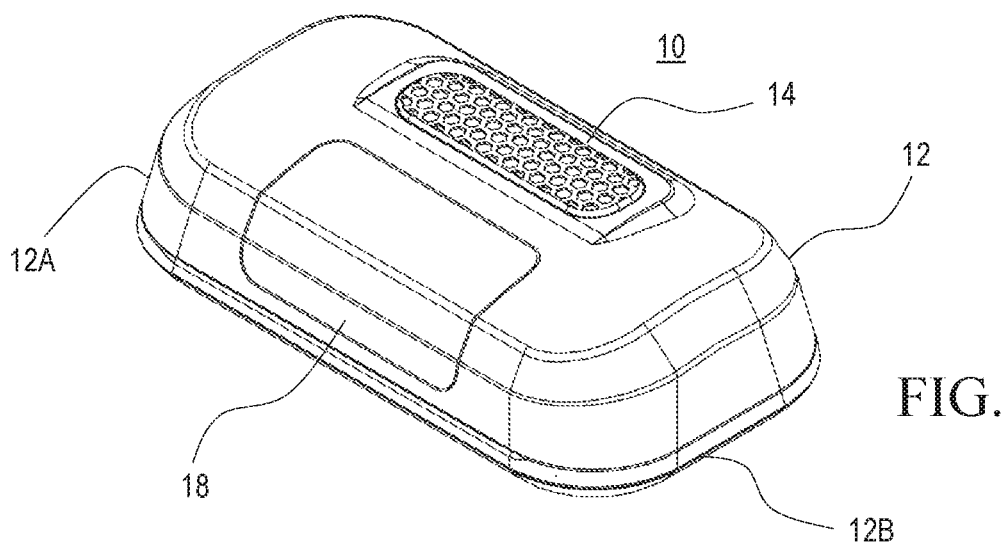
FIG. 1A shows an isometric view of a drug delivery pump having a multi-function drive mechanism, according to one embodiment of the present invention (shown without the adhesive patch)

The present invention provides systems and methods that are related to delivery of drug substances at a predetermined time and at an adjusted delivery rate. Particularly, the present invention relates to drug pump delivery devices that include control systems and sub-systems that are configured to control and drive multi-function drive mechanisms. Additionally, the control systems and sub-systems may be configured to deliver drug substances at appropriate delivery rates after a certain wait or delay time period has elapsed.

In one example, a user may be provided with a pre-filled drug delivery pump device to inject the drug substance via the parenteral method. In such an example, activation of the pump device may establish short range communication with a mobile device (e.g., a smart phone). In one embodiment, the drug pump delivery device may be activated by press of an activation button or a power button. The mobile device may include one or more mobile applications that may be configured to process, receive and transmit data related to the drug delivery process. The mobile application may communicate with external sensors (e.g., a heart rate sensor and a glucose rate sensor) and receive information (e.g., heart rate of the user, glucose/insulin information, etc.) related to the health and/or state of the patient during a monitoring period. The mobile application may further calculate an adjusted delivery rate for the drug based on the data received from the sensors.

Moreover, the drug pump device may request user-activation for the needle insertion, after the device has been activated. The drug pump device may provide visual or audio cues for the needle activation or, alternatively, cause the mobile device to provide the request notification for needle activation. When the needle insertion has been actuated by the user, the drug pump device may then initiate a timer to track a wait time period, prior to the delivery of the drug. Alternatively, the timer may be initiated upon activation of the device. The drug pump device may optionally monitor the temperature to determine whether the drug has reached an optimal temperature for delivery. Additionally, the power and control system may be configured to determine whether the predetermined wait time period has elapsed, and based on the determination may notify the user about the initiation of the drug delivery process. Optionally, the user may have the option of initiating drug delivery after the predetermined wait time has elapsed.

It is noted that, based on the type of the drug and the dose, the drug pump device may regulate the delivery rate of the drug. The regulation and/or adjustment of the delivery rate may also be based on information received from sensors (e.g., temperature sensor, heart rate sensor, glucose monitor sensor).

The drug pump device may further determine whether the drug delivery has ended, and based on the determination, may transmit the end of drug delivery information to the mobile device.

The mobile device may further provide the received end of delivery information to a remote server (e.g., a cloud computer server). The end of delivery information may include, but not limited to, end of delivery indication, delivery rate, delivery start and end times, total delivery time, drug temperature, and data gathered by the sensors. The information may also include information related to the drug and/or pump device such as drug volume, manufacturing date, filling date, serial/lot number, etc.

Moreover, the drug pump delivery device may switch between an active power mode and a non-active power mode. During the active power mode, the power and control system may interact with one or more motors of a drive control system to actuate one or more drive mechanisms, and as such, both the power and control system and the motors may receive power from an energy source (e.g., batteries). On the other hand, in some instances, the power and control system may not need to interact with the drive control system to execute one or more operations of the drug delivery pump device. For example, the drug pump delivery device may establish and communicate with the mobile device, or monitor temperature of the drug without interacting with the drive control system of the drug pump device. In such instances, the power and control system may only be powered, and the drive control system may not receive power from the batteries. Additionally, one or more components or functions of the pump device may be powered intermittently in one or more modes.

The switching between the active power mode and the non-active power mode may substantially save power resources of the drug pump device. For example, upon switching to the non-active power mode, the drug pump device does not need to provide power to the motors, which may, otherwise, significantly drain the batteries.

Particularly, during the active power mode, the power and control system of the drug delivery pump device controls the multi-function drive mechanisms to initiate several sub-systems or functions, including: (i) controlling the rate of drug delivery by metering, providing resistance, or otherwise preventing free axial translation of the plunger seal utilized to force a drug substance out of a drug container; (ii) triggering a needle insertion mechanism to provide a fluid pathway for drug delivery to a user; and (iii) connecting a sterile fluid pathway to a drug container to permit fluid flow from the drug container to the needle insertion mechanism for delivery to the user.

The drive mechanisms of the present invention may control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present invention may include integrated status indication features, such as sensors, which may provide feedback to the power and control system, and in turn, to the user before, during, and after drug delivery. For example, the user may be prompted by one or more sensors to identify that the devices are operational and ready for drug delivery. Upon activation of one or more devices, the sensors may provide one or more drug delivery status indications to the user such as an end-of-dose indication at completion of drug delivery.

As used herein to describe the drive mechanisms, drug delivery pumps, or any of the relative positions of the components of the present invention, the terms "axial" or "axially" refer generally to a longitudinal axis "A" around which the drive mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of the drug pumps. According to various aspects and embodiments described herein, reference is made to a "biasing member", such as in the context of one or more biasing members for asserting force on a plunger seal. It will be appreciated that the biasing member may be any member that is capable of storing and releasing energy. Non-limiting examples include a spring, such as for example a coiled spring, a compression or extension spring, a torsional spring, or a leaf spring, a resiliently compressible or elastic band, or any other member with similar functions. In at least one embodiment of the present invention, the biasing member is a spring, preferably a compression spring.

The devices of the present invention provide drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The devices of the present invention provide these desirable features without any of the problems associated with known prior art devices. Certain non-limiting embodiments of the drug delivery pumps, drive mechanisms, and their respective components are described further herein with reference to the accompanying figures.

Figure 1B:
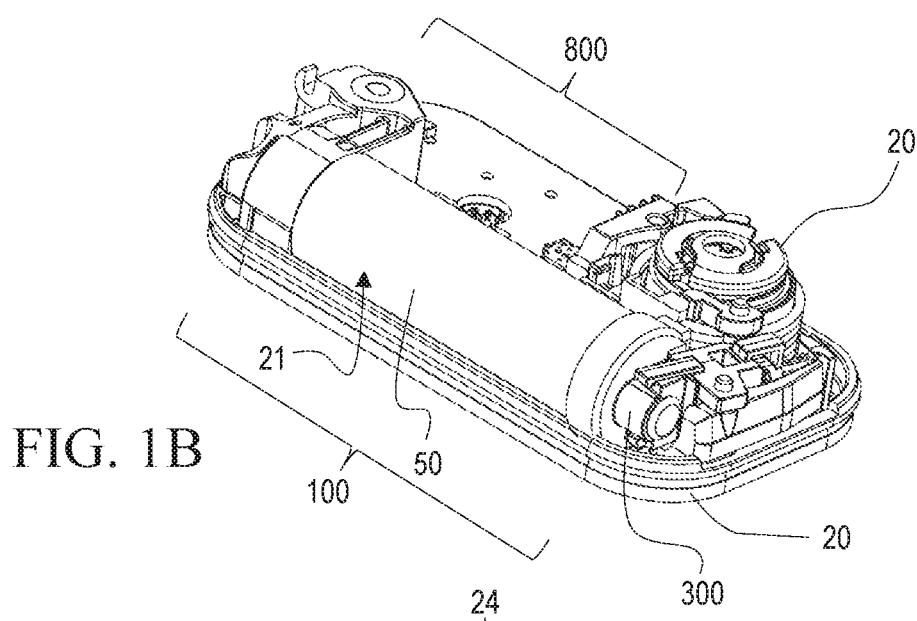
FIG. 1B shows an isometric view of the interior components of the drug delivery pump shown in FIG. 1A (shown without the adhesive patch)
Figure 1C:
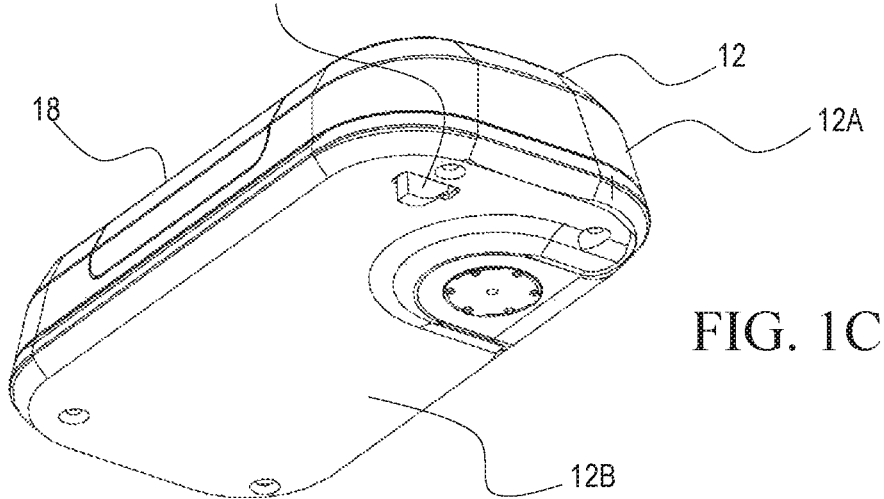
FIG. 1C shows an isometric bottom view of the drug delivery pump shown in FIG. 1A (shown without the adhesive patch)

As used herein, the term "pump" is intended to include any number of drug delivery systems which are capable of dispensing a fluid to a user upon activation. Such drug delivery systems include, for example, injection systems, infusion pumps, bolus injectors, and the like. FIGS. 1A-1C show an exemplary drug delivery device according to at least one embodiment of the present invention. In FIG. 1B the top housing is removed so that the internal components are visible. The drug delivery device may be utilized to administer delivery of a drug treatment into a body of a user. As shown in FIGS. 1A-1C, the drug pump 10 includes a pump housing 12. Pump housing 12 may include one or more housing subcomponents which are fixedly engageable to facilitate easier manufacturing, assembly, and operation of the drug pump. For example, drug pump 10 includes a pump housing 12 which may include an upper housing and a lower housing (not shown for ease of viewing internal components). The pump housing 12 may include one or more tamper evidence features to identify if the drug delivery device has been opened or tampered with. For example, the pump housing 12 may include one or more tamper evidence labels or stickers, such as labels that bridge across the upper housing and the lower housing. Additionally or alternatively, the housing 12 may include one or more snap arms or prongs connecting between the upper housing and the lower housing. A broken or altered tamper evidence feature would signal to the user, the physician, the supplier, the manufacturer, or the like, that the drug delivery device has potentially been tampered, e.g., by accessing the internal aspects of the device, so that the device is evaluated and possibly discarded without use by or risk to the user. The drug pump may further include an activation mechanism, a status indicator, and a window. The window may be any translucent or transmissive surface through which the operation of the drug pump may be viewed. As shown in FIG. 1B, drug pump 10 further includes assembly platform 20, sterile fluid conduit, drive mechanism 100 having drug container 50, insertion mechanism 200, fluid pathway connection 300, and a power and control system 800. One or more of the components of such drug pumps may be modular in that they may be, for example, pre-assembled as separate components and configured into position onto the assembly platform 20 of the drug pump 10 during manufacturing.

The pump housing 12 contains all of the device components and provides a means of removably attaching the device 10 to the skin of the user. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as one or more status indicators (e.g., LED lights, audio tones via speakerphones) and windows, which may provide operation feedback to the user.

In one example, the power and control system may be configured to provide a number of different status indications to the user. For example, the power and control system may be configured such that after the on-body sensor (e.g., skin sensor) is triggered, the power and control system provides a ready-to-start status signal via the status indicator (e.g., audio tones and/or blinking lights) if device start-up checks provide no errors. After providing the ready-to-start status signal and, in an embodiment with the optional on-body sensor, if the on-body sensor remains in contact with the body of the user, the power and control system will power the drive mechanism 100 to begin delivery of the drug treatment through the fluid pathway connection 300 and sterile fluid conduit.

Additionally, the power and control system may be configured to identify removal of the drug pump from its packaging. The power and control system may be mechanically, electronically, or electro-mechanically connected to the packaging such that removal of the drug pump from the packaging may activate or power-on the power and control system for use, or simply enable the power and control system to be powered-on by the user. In such an embodiment, without removal of the drug pump from the packaging the drug pump cannot be activated. This provides an additional safety mechanism of the drug pump and for the user. In at least one embodiment, the drug pump or the power and control system may be electronically or electro-mechanically connected to the packaging, for example, such as by one or more interacting sensors from a range of: Hall effect sensors; giant magneto resistance (GMR) or magnetic field sensors; optical sensors; capacitive or capacitance change sensors; ultrasonic sensors; and linear travel, LVDT, linear resistive, or radiometric linear resistive sensors; and combinations thereof, which are capable of coordinating to transmit a signal between components to identify the location there-between.

Additionally or alternatively, the drug pump or the power and control system may be mechanically connected to the packaging, such as by a pin and slot relationship which activates the system when the pin is removed (i.e., once the drug pump is removed from the packaging).

In a preferred embodiment of the present invention, once the power and control system has been activated, and after a predetermined wait time period, the multi-function drive mechanism is initiated to actuate the drug fluid to be forced from the drug container.

During the drug delivery process, the power and control system may be further configured to provide a dispensing status signal via the status indicator. After the drug has been administered into the body of the user and after the end of any additional dwell time, to ensure that substantially the entire dose has been delivered to the user, the power and control system may provide an okay-to-remove status signal via the status indicator. This may be independently verified by the user by viewing the drive mechanism and drug dose delivery through the window of the pump housing 12. Additionally, the power and control system may be configured to provide one or more alert signals via the status indicator, such as for example alerts indicative of fault or operation failure situations.

The power and control system may additionally be configured to accept various inputs (e.g., via an activation button) from the user to dynamically control the drive mechanisms 100 to meet a desired drug delivery rate or profile. For example, the power and control system may receive inputs, such as from partial or full activation, depression, and/or release of the activation mechanism, to set, initiate, stop, or otherwise adjust the control of the drive mechanism 100 via the power and control system to meet the desired drug delivery rate or profile. Similarly, the power and control system may be configured to receive such inputs to initiate communication with the mobile device, adjust the drug dose volume, to prime the drive mechanism, fluid pathway connection, and fluid conduit; and/or to start, stop, or pause operation of the drive mechanism 100. Such inputs may be received by the user directly acting on the drug pump 10, such as by use of the activation mechanism 14 or a different control interface, or the power and control system may be configured to receive such inputs from a remote device (e.g., a mobile device). Additionally or alternatively, such inputs may be pre-programmed.

Other power and control system configurations may be utilized with the drug pumps of the present invention. For example, certain activation delays may be utilized prior to, or during drug delivery. For example, a wait-time period may be a pre-determined time that may be set in the power and control system, and which may delay the delivery of the drug by the pre-determined amount of time. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the drug pumps.

In one embodiment, the drug delivery pump device 10 may include one or more control systems such as, but not limited to, power and control system 800 and drive control system 820. As disclosed above, the drug delivery pump 10 may further include various mechanisms or sub-systems such as, but not limited to, drive mechanism or sub-system 100, needle insertion mechanism (NIM) or sub-system 200, sterile fluid pathway connection (SFPC) or sub-system 300, and regulating mechanism or sub-system 500. In some examples, the control systems may include printed circuit board (PCB), motherboards and/or daughter boards.

In some embodiments, the sub-systems may be included in the control systems. For example, the drive control system 820 may include the drive sub-system 100, NIM sub-system 200, and/or the regulating sub-system 500. In such examples, the power and control system 800 may control the sub-systems by sending command signals to the drive control system 820.

In other examples, the drive control system 820 may not include the sub-systems. As such, in those examples, the power and control system 800 may control the sub-systems via the drive control system 820. For example, the power and control system 800 may send command signals to the drive control system 820. The drive control system 820, for example, may then selectively control one or more of the sub-systems based on the received command signals from the power and control system 810.

Yet in another embodiment, the power and control system 800 may directly control the sub-systems. In that embodiment, the sub-systems may include respective control units or controller and storage units (not shown) that may be configured to directly communicate with the power and control system 800.

Alternatively, in some implementations, the power and control system 800 may include the drive control system 820 and the sub-systems, and one or more other control systems and sub-systems.

Figure 8A:
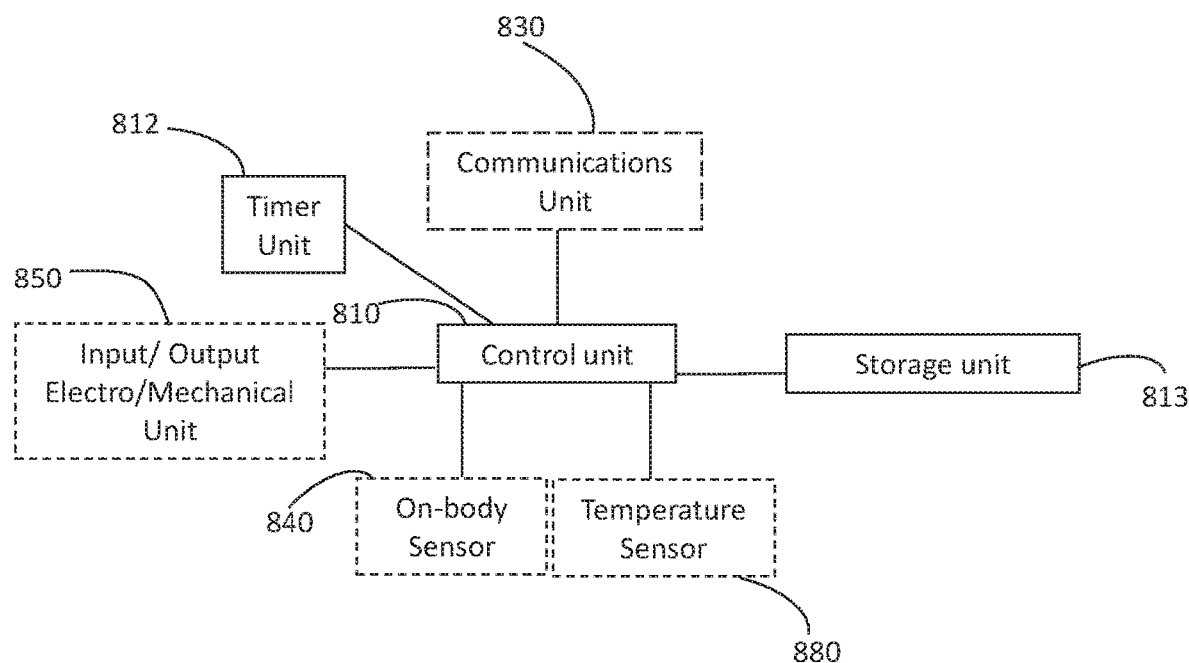
FIG. 8A is an exemplary block diagram illustrating one embodiment of a power and control system of the drug delivery pump.

As shown in FIG. 8A, in one exemplary embodiment, the power and control system 800 may be included in the drug delivery pump 10. The power and control system 800 may include one or more control units that are connected to one or more sensors, timers and storage units of the drug delivery pump 10.

In some implementations, the power and control system 800 may be configured to control a delay time period related to drug delivery. In such implementations, the power and control system 800 may monitor and control time parameters for initiating and delivering the drug after the activation of the drug delivery pump 10. For example, upon the activation of the device 10, the power and control system 800 may monitor a wait period time (e.g., a predetermined delay time) prior to the initiation of the drug delivery. In one example, during the wait period, the power and control system 800 may optionally prime the device.

In one example, the power and control system 800 may provide request notification to activate the NIM mechanism after the device has been activated. The request notification may be provided directly by the drug pump delivery device 10, or via the mobile device 11. Upon notifying the user to initiate the NIM mechanism 200, the power and control system may further determine whether an activation/initiation signal (e.g., from the user) is received via the activation button.

When the power and control system 800 determines that the activation signal is received (e.g., within an NIM activation predetermined time), the power and control system may cause the NIM sub-system to activate. Alternatively, the NIM may be directly activated by the user. The power and control system 800 may further notify the user that the delivery of the drug has been initiated. It is noted that, the power and control system 800 may activate the NIM mechanism upon receiving the activation signal related for the NIM activation and, upon further receiving signal from on-body sensor that indicates that the drug pump device 10 is sensing the skin of the user. Optionally, when the power and control system determines that the activation signal is not received, and/or the on-body sensor is not sensing a skin portion of the user, the power and control system 800 may notify the user (e.g., via an audible tone), and optionally terminate the drug delivery process.

Moreover, in some implementations, when the power and control system 800 determines that the wait period time has elapsed, the power and control system may notify the user about the initiation of the delivery of the drug. The power and control system may further notify the user that the delivery of the drug has been initiated.

Optionally, the power and control system 800 may further notify the user of a time period of the drug delivery (e.g., the total time that will be taken for delivering the drug). The power and control system 800 may communicate the notification to an external device via the communication unit 830.

Upon the initiation of the drug delivery, the power and control system may further control timing and/or rate parameters for the drug delivery. For example, the power and control system may control the regulating sub-system or mechanism to deliver the drug in a given period of time.

Moreover, the power and control system may process various data captured by the internal and external sensors to determine the timing and/or rate parameters for the drug delivery. Based on the determination, the power and control system may deliver the drug to the user within the appropriate time period.

The power and control system may or may not include all the elements of the power and control system 800, and/or may include additional elements. Additionally, in some examples, the drug pump device 10 may include one or more control systems, including, but not limited to, the power and control system, and may include additional elements for the operations of the drug pump device.

In some implementations, control system 800 may include a main control unit or control unit 810. The main control unit 810 may include one or more controllers, microcontrollers, microprocessors, or application specific integrated circuits (ASICs). Main control unit 810 may be implemented as hardware or a combination of hardware and software that may be programmed with instructions. The main control unit 810 may be configured to execute such instructions to effect various operations of the drug pump device 10. Moreover, the power and control system or the main control unit 810 may communicate, for example, by receiving and/or sending signal or data to and from the communication unit 830, timer unit 812, storage unit 813, on-body sensor 840, temperature sensor 880, and I/O unit 850. In addition, the power and control system may include one or more of the above, such as, for example, timer unit 812. The main control unit 810 may process and interpret the data collected or monitored by the various elements in the one or more control systems in order to determine and execute various functions and operations of the drug pump device 10.

It is noted that, the drug pump device 10 may operate in two power modes, namely, an active power mode and a non-active power mode. During the active power mode, the power and control system 800 and the motor 101 may receive power from the power source (e.g., batteries), and the power and control system 800 may command the drive control system 820 to drive various operations, such as the NIM mechanism 200, and/or regulating mechanism 500. Whereas, during the non-active power mode, the power and control system 800 may be powered, and the motor 101 may not be powered. During the non-active power mode, the power and control system 800 may execute various operations of the drug pump device 10 that may not require operations related to the motor 101. For example, the power and control system 800 may establish communication link with the mobile device 11, and further communicate intermittently or continuously with the mobile device 11 during the non-active power mode. Additionally, during the non-drive mode, the power and control system 800 may provide notifications, and alert to the user, and may further communicate with the various sensors (e.g., the temperature sensor and on-body sensor), and/or determine timings of various operations. Optionally, the drug pump device 10 may be primed during the non-active power mode.

Moreover, the drug pump device 10 may switch between the active power mode and the non-active power mode.

The different power modes may be initiated, based on: (a) type of activation (e.g., device activation, activation of the drug delivery, control of the drug delivery, initiation of the timer, etc.), (b) predetermined time set (e.g., after, or, during the wait time period), and/or (c) operations (e.g., communication with the mobile device and/or sensors, control of the various operations by the power and control system 800)

of the drug pump device 10. Alternatively, the activation and/or switching between the modes may be performed manually by the user of the drug pump device 10.

It will be appreciated that, by appropriately powering up the motor 101 and the power and control system 800, the overall power requirement of the drug pump device 10 may be reduced. For example, powering the motor 101 while the motor 101 is idle may prematurely drain the power source or battery of the drug pump device 10. As such, by managing the power cycle, for example, by providing power to the motor 101 only when activities related to the motor 101 are initiated, the life of the battery to operate the drug delivery device 10 may be suitably increased or the demand for power to operate the drug delivery device 10 over the life of the drug delivery period may be significantly reduced.

Timer unit 812 may be a digital clock that may be programmed, for example, to set up time periods for various operations of the drug pump device 10. For example, the timer unit 812 may be configured to indicate, to the main control unit 810, a wait time or a delay period time for a drug (i.e., a time period before the drug can be forced to be delivered). During the wait time period, the power and control system may enter a delay mode in which power consumption is reduced.

Additionally, timer unit 812 may indicate a time-out period for receiving an activation signal (i.e., a time period within which a user may provide an activation signal to initiate drug delivery or NIM 200). In some embodiments, timer unit 812 may directly communicate with the control units of various sensors. In some implementations, the timer unit 812 may be included in the main control unit 810.

Control system 800 may include storage unit 813. Storage unit 813 may include one more storage units, such as a random access memory (RAM) or other dynamic storage device, and/or a read only memory (ROM), and/or an electrically erasable programmable read only memory (EEPROM) for storing temporary parameters, information and instructions for the main control unit 810. In some implementations, the storage unit may be implemented as a non-transitory computer readable medium which stores instructions that may be processed and executed by the control unit to control operations of the control system of the drug pump device. Additionally, storage unit 813 may store error codes or error notification for various operations associated with the sensors and control unit of the drug pump device 10. The error codes may be pre-programmed into the storage unit 813.

Storage unit 813, may additionally, store various predetermined delay or wait time periods related to the drug delivery.

In some examples, power and control system 800 may include communication unit 830. Communication unit 830 may include one or more 802.11 Wi-Fi transceivers, a cellular transceiver, IEEE 802.14 ZigBee transceiver, a Bluetooth transceiver, and/or a Bluetooth Low Energy (BLE) transceiver, and for other wireless communication protocols, such as near-field communication (NFC), infrared or ultrasonic. The drug pump device 10 may include appropriate antenna (not shown), for communication with an external computer device, and may receive/transmit data via the communication unit 830.

Figure 8B:
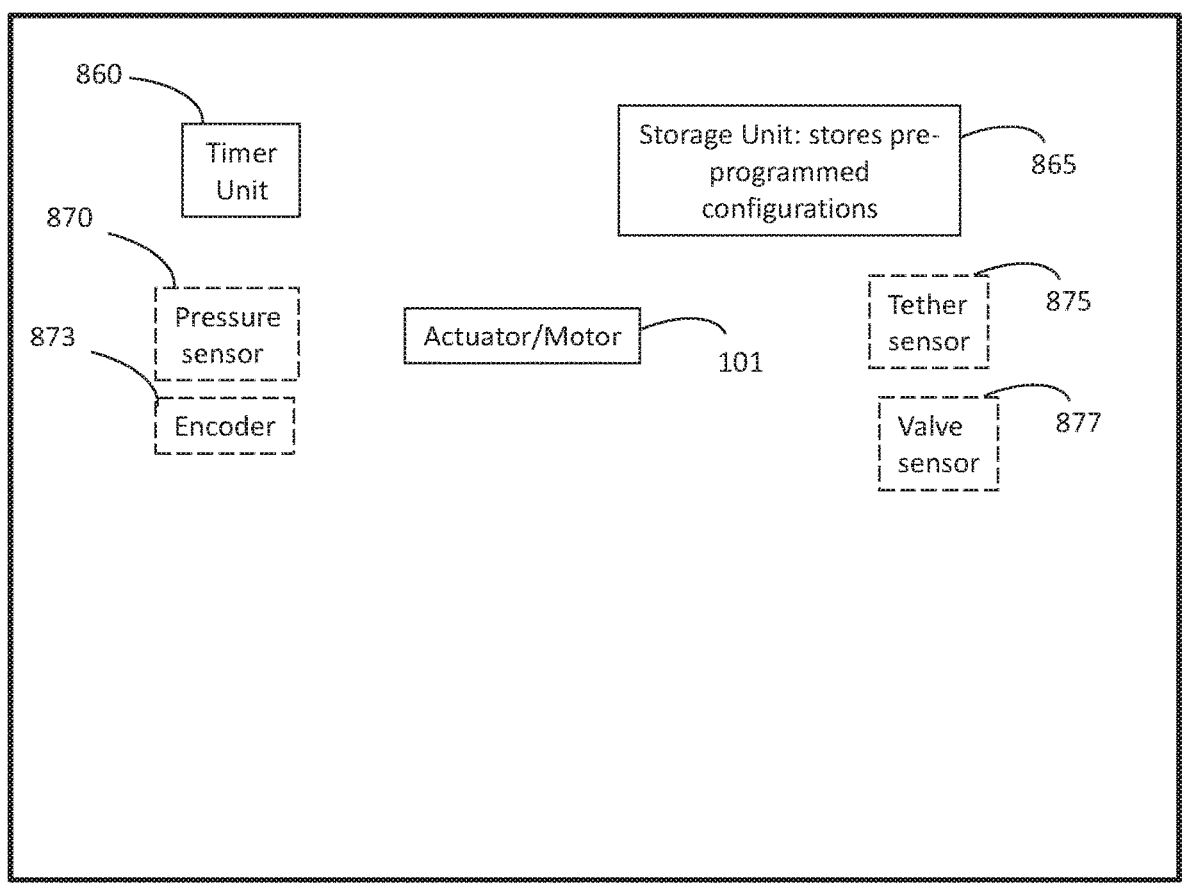
FIG. 8B is an exemplary block diagram depicting one embodiment of a drive control system of the drug delivery pump.
Figure 8C:
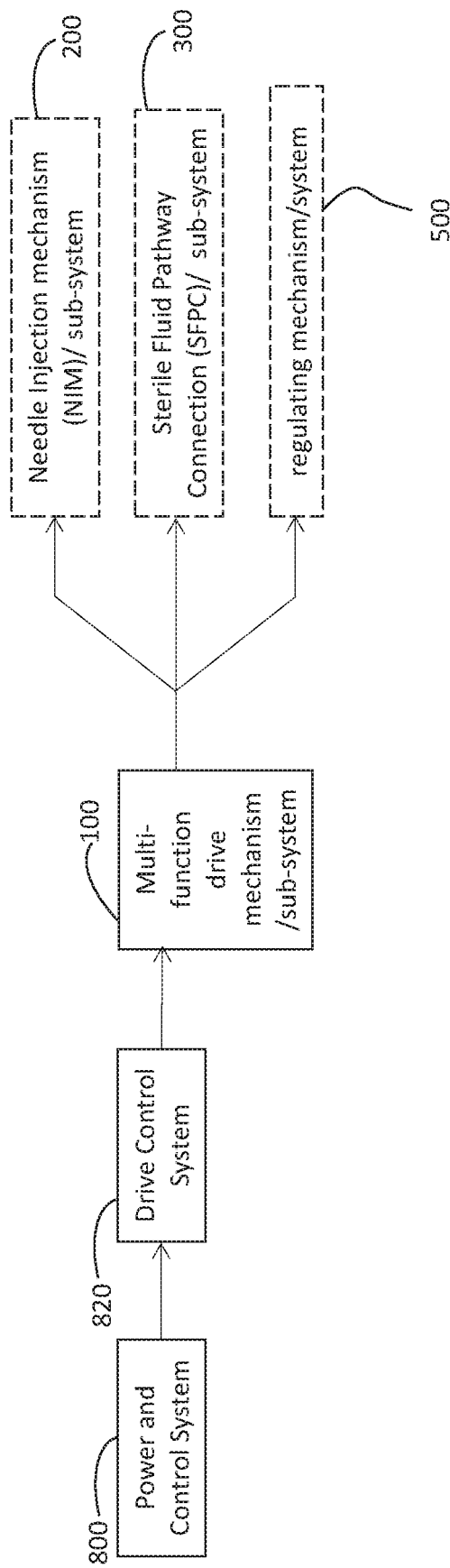
FIG. 8C is an exemplary block diagram of an embodiment illustrating various control mechanisms of the drug delivery pump.
Figure 8D:
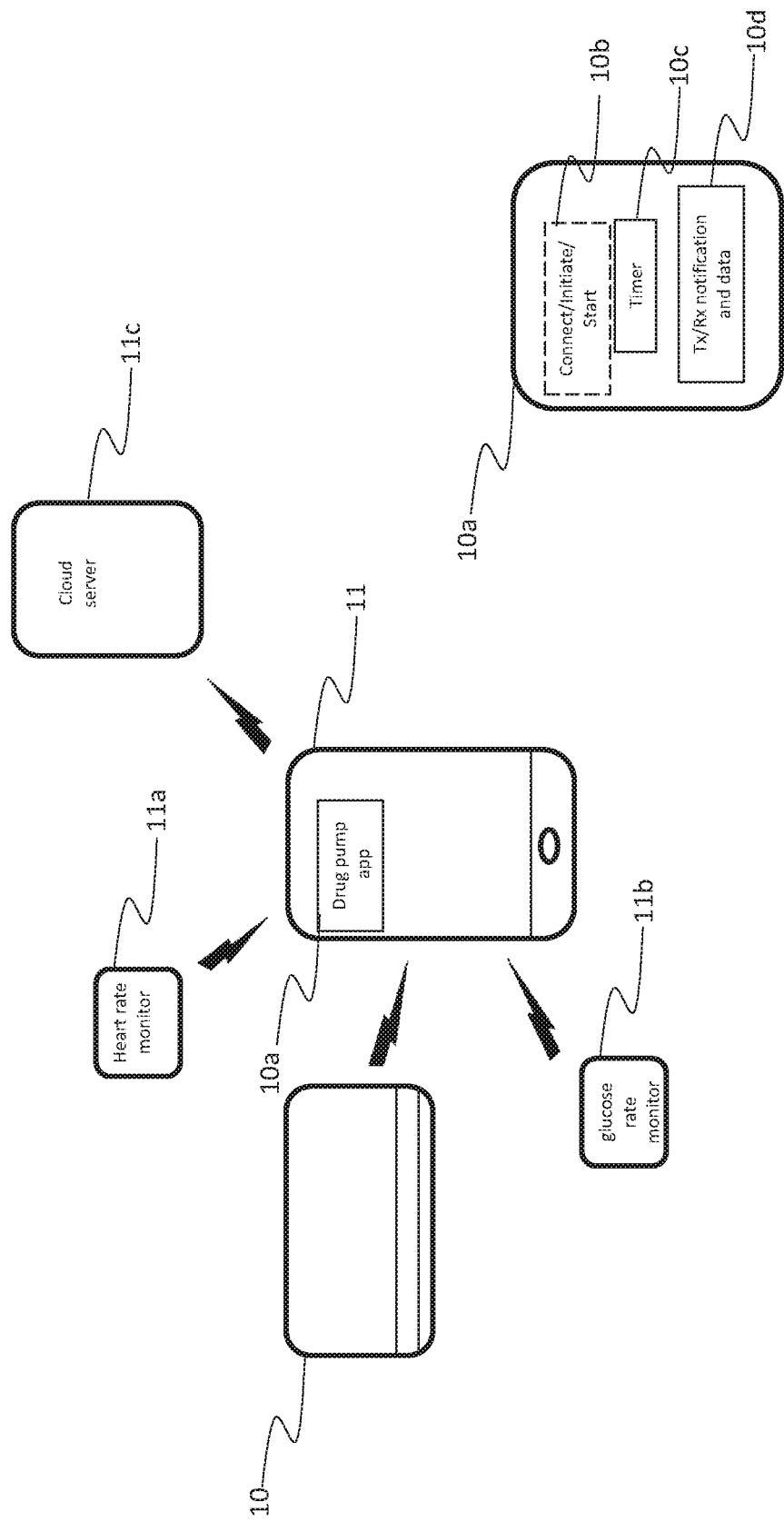
FIG. 8D is an exemplary block diagram of another embodiment illustrating communication among an exemplary drug delivery pump device, an exemplary mobile device, an exemplary cloud server and one or more exemplary sensors.

As shown in FIG. 8D, the drug pump device 10 may communicate with an external computing device (via the communication unit 830). The external computing device may be mobile computing device 11 such as a smart phone which may include various mobile applications and may be configured with the appropriate communication protocols.

In one example, the mobile device 11 may include a pump device mobile application (app) 10a that communicates with the drug pump device 10. In such an example, the mobile app 10a may be provided (from the manufacturer of the drug or drug pump device 10) to the user upon purchasing the drug or the drug pump device 10. For example, the container or the box of the drug pump device 10 may include a unique download identifier that the user may use to download the drug pump device mobile app 10a. For example, the user may use the download identifier to download the app 10a from Apple Store or Google Play store.

Upon downloading the drug pump app 10a to the mobile device 10a, the user may communicate with the drug pump device 10 using the drug pump application 10a (e.g., upon establishing a wireless communication link with the drug pump device 10). The mobile app 10a may be configured to cause the mobile device 11 to process various information received from the drug pump device 10, external entities, such as sensors 11a and 11b, and/or optionally data received from a cloud server. Based on the processing of such data, the mobile app 10a may cause the mobile device 11 to transfer appropriate data to the external cloud server 11c. Mobile app 10a may further cause the mobile device 11 to display appropriate notification to the user based on the processing of such data.

In one example, the user may optionally select the activation button 10b to establish a short range wireless connection with the drug pump device 10. In one example, the activation button 10b may initiate a Bluetooth discovery and pairing process for the mobile device 11.

Moreover, when the drug pump device 10 is activated and in communication with the mobile device 11, mobile app 10a may receive a notification from the drug pump device 10 (via the communication unit 830) that indicates activation of the drug pump device 10. In some examples, activation button 10b may additionally be configured to initiate, modify and/or terminate various mechanisms of the drug delivery process.

In some examples, drug pump app 10a may gather and provide various time period information of the drug delivery process to the user. Particularly, in one example, selection of the timer button 10c may provide information related to various timing periods related to the drug delivery process. The timer button 10c may be triggered, in one example, upon the selection of the activation button 10b. In one example, the selection of the timer button 10c may evoke a clock or stop watch application of the mobile device 11.

In one example, upon the activation of the drug pump device 10 and the initiation of the timer unit 812, the user may gather information related to the predetermined wait time period prior to the initiation of the drug delivery.

Optionally, drug pump app 10a may provide alarm notification. For example, the timer button 10c may be configured to provide alarm notification prior to the initiation of the drug delivery process. In one example, the user may optionally indicate how often to receive alarm notification prior to the drug delivery process. Timer button 10c may be further configured to indicate the delivery time period when the drug is being delivered to the user.

Moreover, drug pump app 10a may be configured to receive information, for example, from the drug pump device 10. For example, a user may select the Tx/Rx notification and data button 10d to receive notification related to the drug delivery process (e.g., from the drug delivery pump device 10), and transmit information related to the drug delivery process (e.g., to the cloud server 11c).

In one example, upon the selection of the Tx/Rx button 10d, the user may view notification related to the drug delivery process, such as the activation of the drug pump device 10, and/or end of dose notification.

Additionally, the user may view data via the Tx/Rx button 10d related to the drug delivery process, such as the rate at which the drug was delivered, the total time period of the delivery process. In one example, the user may further transfer the data and/or notification to a cloud server 11c of relevant entities (e.g., physician, health insurance company, etc.) In such a scenario, the drug pump application 10a may evoke the communication interface (e.g., a cellular communication interface) of the mobile device 11 to communicate such information that is received from drug pump device 10 to the external cloud server 11c.

In one example, the mobile app 10a may collect information from other sensors that are local or external to the mobile device. For example, the mobile app 10a may collect information from a wireless heart rate sensor 11a, a wireless glucose rate monitor 11b and cause the mobile device 11 to process such information. Based on the processed information, the mobile app 10a may determine delivery rate for the drug, and provide instruction to the user about the delivery rate information and activation inputs for the drug pump device 10.

It is contemplated that, the drug pump device 10 may wirelessly communicate with the heart rate sensor 11a and/or the glucose rate monitor 11b and process the received information to determine the drug delivery rate for the drug.

Referring back to FIG. 8A the power and control system 800 may include on-body sensors 840, such as mechanical, electro-mechanical skin sensors, and/or electrical skin sensors, for example, a capacitive skin sensor. In one example, the on-body sensor 840 may be configured to detect whether the pump device 10 is in contact with the skin of the patient. Based on the determination, the on-body sensor may provide appropriate indication (e.g., signals) to the control unit 810. The control unit 810 may then control various functions of the drug pump 10. For example, the control unit 810 may notify the user to initiate a delivery of the drug only when the pump device 10 is in contact with the skin of the user. This may be a safety feature of the drug pump 10, as the drive control system 820 may not be activated until the power and control system receives a signal from the on-body sensor 840.

In one example, on-body sensor 840 may be a mechanical switch, and the depression of the mechanical on-body sensor 840 may trigger the activation of the power and control system 810, and/or the drive control system 820. In another embodiment, the on-body sensor may be a capacitive- or impedance-based skin sensor, and the power and control system and/or the drive control system 820 may be functional upon receiving signal from the on-body sensor. These concepts are not mutually exclusive and one or more combinations may be utilized within the breadth of the present invention to prevent, for example, premature activation of the drug pump 10. In a preferred embodiment, the drug pump 10 utilizes one or more mechanical on-body sensors. Additional integrated safety mechanisms are described herein with reference to other components of the drug pumps.

Power and control system 800 may optionally include one or more temperature sensors 880. The temperature sensor 880 may be suitably positioned near the drug or the drug container 50, and configured to detect the temperature of the drug. The temperature sensor may be thermocouples or thermistors (i.e., resistors whose resistances vary significantly with temperature), and electrically coupled to the control unit 810. The control unit 810 may process the detected temperature information that is received from the temperature sensor 880 to control various operations of the drug pump device 10. In one example, based on the detected temperature of the drug, the control unit 810 may notify the user to initiate the delivery of the drug prior to, or after a predetermined time has elapsed. In such a scenario, the control unit 810 may be configured to override the predefined wait period time related to the drug delivery.

The power and control system 800 may include a power source, such as batteries (not shown), that provides power to various electrical components of the drug pump device 10.

Moreover, the input/output electro-mechanical unit 850 may include an activation button, one or more feedback mechanisms, for example, audible alarms such as piezo alarms and/or light indicators such as light emitting diodes (LEDs).

In one embodiment, the control unit 810 of the power and control system 800 interfaces with the mechanical on-body sensor 24 or the electrical and/or electro mechanical on-body sensor 840 to identify when the device is in contact with the user and/or the activation mechanism to identify when the device has been activated.

The power and control system 800 interfaces and controls the drive control system 820 through one or more interconnects to relay status indication, such as activation, drug delivery, and end-of-dose, and receives status feedback from the drive control system. The status indication or the status feedback may be presented to the user via the I/O unit 850, such as auditory tones or alarms, and/or via visual indicators, such as through the LEDs.

In one embodiment, the control interfaces between the power and control system 800 and the other components of the drive control system 820 are not engaged or connected until activation by the user (e.g., via the activation button). This is a desirable safety feature that prevents accidental operation of the drug pump, and may additionally maintain and save the battery power during storage, transportation, and the like.

In one implementation, upon activation of the drug pump device 10 (e.g., via the activation button of the I/O unit 850), the multi-function drive mechanism 100 of the drive control system 820 is activated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. In at least one embodiment, such delivery of drug fluid into a user is performed by the drive control system multi-function drive mechanism in a controlled manner (e.g., via the flow rate control sub-system 825).

FIG. 8B illustrates an exemplary drive control system 820 that may be configured to drive and control various mechanical and electro-mechanical components of the drug pump device 10. One or more components of the power and control system 800 (e.g., the control unit 810) may interface with the drive control system 820, and instruct the actuator/motor 101 to drive various elements of the drug pump device 10.

In some embodiments, control unit 810 is electrically coupled and configured to communicate with motor 101, and any other elements of the drive control system 820.

In some examples, the drive control system 820 may optionally include various sensors such as, but not limited to, pressure sensor 870 that may be configured to provide information of the pressure in the container 50, tether sensor 875 that may be configured to provide a status information of the tether 525 and a valve senor 877 that may be configured to provide a status information of the fluid pathway connection 300 that may be provided on the container. The sensors 870, 875 and 877 may be electrical and/or electro-mechanical components and may communicate with the control unit 810 by providing status signals corresponding to the respective sensors. The control unit 810 may process such signals to execute and/or delay execution of the control of various sub-systems via the motor 101.

In one example, the drive control system 820 may optionally include timer unit 860. Timer unit 860 may be a digital clock that is coupled to the control unit 810. In one example, the timer unit 860 may be included in the control unit 810. In some examples, the timer unit 860 may be the same as timer unit 812.

The drive control system may include an actuator or motor 101. The actuator 101 may be a number of power/motion sources including, for example, a solenoid, a stepper motor, or a rotational drive motor. In one embodiment, the actuator 101 is a rotational stepper motor with a notch that corresponds with the gear teeth of the main/star gear 102.

In some embodiments (see FIGS. 1A-5D), the actuator 101 is in vertical alignment and in direct engagement with the main/star gear 102. As would be readily appreciated by one having ordinary skill in the mechanical arts, the actuator 101 could be modified to be in horizontal alignment. Additionally or alternatively, the actuator 101 may be modified to be in indirect engagement with the main/star gear 102, as discussed below with reference to FIGS. 7A and 7B.

With reference to FIG. 8C, the drive control system 820 may control the drive mechanisms of the drug pump device 10. In one example, the drive control system may control the drive mechanism or sub-system 100 to control the NIM or sub-system 200, establish the SFPC 300 and further control the regulating mechanism 500 of the drug pump device 10.

In one example, the initiation time of the needle insertion mechanism 200, time to establish the fluid pathway connection 300, and a drug delivery rate of the drug may be determined by the power and control system 800 based on the various inputs received by the power and control system from external sensors (e.g., the glucose rate, heart rate, etc.) The power and control system 800 may then transmit the appropriate command signals and information (e.g., the delivery rate information) to the drive control system 820.

Furthermore, the storage unit 865 of the drive control system 820, and/or the storage unit 813 may store, in a lookup table and/or database, pre-programmed configurations and setting information such as ratio of gear assembly information (e.g., ratio of gear assembly 516), rate of rotation of gear information (e.g., rate of rotation of the main star gear 102), and diameter information of gears and drums. As such, upon receiving the delivery rate information, the control unit 810 may consult the storage unit 865 or storage unit 813 to identify and select the appropriate configuration of the gear assembly and the motor from the lookup table or the database. Based on the selection, the control unit 810 may drive the motor 101 to control the drive mechanism 100, NIM mechanism 200 and the regulating mechanism 500 to deliver the drug at the desired rate.

Moreover, the drive control system 820 may interact with the power and control system 810 and receive command signals after a predetermined time to control the various drive mechanisms of the drug pump device 10.

For example, the drive control system 820 may receive the command signal and timing information to control or initiate the driving mechanism after a predetermined time. In this example, the control unit 810 may consult the timer unit 860 or timer unit 812 to determine the initiation time of the activation of the drive mechanism. Upon determination, control unit 810 may command the actuator/motor 101 after the predetermined time to initiate a drug delivery process by controlling the drive mechanisms as discussed below.

After the initiation of the drug delivery, the control unit 810 may further consult the timer unit 860 or timer unit 812 to complete the drug delivery in a predetermined time. The power and control system 800 may determine the timing periods, and may send command signals to the drive control system 820 prior to, during, and after the drug delivery process to control the drug delivery process.

It is noted that, the drive mechanism 100, insertion mechanism 200, fluid pathway connection 300 and the regulating mechanism 500 may be controlled by the drive control system 820, concurrently, sequentially and/or non-sequentially, based on a timing period set by the power and control system 810.

In some examples, the drive control system 820 may drive or control the insertion mechanism or sub-system 200 via the drive mechanism 100. The controlling of the insertion mechanism 200 may be performed based on the predetermined wait time period or delay time period, either directly by the power and control system 810, or by the drive control system 820.

In one example, the drive control system 820 may additionally control the insertion mechanism 200 to concurrently provide a fluid pathway connection for drug delivery to a user.

Alternatively, the drive control system 820 may separately (and prior to or after the insertion mechanism 200) establish the sterile fluid pathway connection 300 by connecting a sterile fluid pathway to a drug container to permit fluid flow from the drug container to the needle insertion mechanism for delivery to the user. Details of the control of the insertion mechanism 200 are discussed below.

Insertion Mechanism

A number of insertion mechanisms may be utilized within the drug pumps to activate the needle insertion into the body of the patient. The pump-type delivery devices of the present invention may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. The fluid may be introduced into the body through any number of means, including but not limited to: an automatically inserted needle, cannula, micro-needle array, or infusion set tubing.

In one example, the control unit 810 of the power and control system 800 may receive activation inputs to initiate the drug pump device 10. After a predetermined time or after the determination that the on-body sensor 840 is sensing a skin portion of the user, the power and control system 800 may instruct the drive control system 820 to initiate the NIM 200. After the wait time period, the control unit 810 may actuate one or more biasing members to initiate the needle insertion mechanism or sub-system 200. For example, a biasing member such as a spring may be actuated by the motor 101 to provide sufficient force to cause the needle and cannula to pierce the skin of the patient. The same spring, an additional spring, or another similar mechanism may be utilized to retract the needle from the patient.

In one embodiment, the power and control system 800 and/or the drive control system 820 may actuate the insertion mechanism 200 as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present invention, including a rigid needle insertion mechanism and/or a rotational needle insertion mechanism as developed by the assignee of the present invention.

In at least one embodiment, the insertion mechanism 200 includes an insertion mechanism housing having one or more lockout windows, and a base for connection to the assembly platform and/or pump housing (as shown in FIG. 1B and FIG. 1C). The connection of the base to the assembly platform 20 may be, for example, such that the bottom of the base is permitted to pass-through a hole in the assembly platform to permit direct contact of the base to the body of the user. In such configurations, the bottom of the base may include a sealing membrane that is removable prior to use of the drug pump 10. The insertion mechanism may further include one or more insertion biasing members, a needle, a retraction biasing member, a cannula, and a manifold. The manifold may connect to sterile fluid conduit to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 27 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. The base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane (not visible).

According to at least one embodiment of the present invention, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. In one example, the power and control system 800 may send command signals to the drive control system 820 to initiate the needle insertion mechanism 200 after the wait time period. Upon receiving the command signal, the actuator 101 may cause displacement of the lockout pin(s), such as pulling, pushing, sliding, and/or rotation. This may cause the insertion biasing member to decompress from its initial compressed, energized state. Particularly, the decompression of the insertion biasing member drives the needle and, optionally, the cannula into the body of the user. At the end of the insertion stage or at the end of drug delivery (as triggered by the multi-function drive mechanism 100 and/or the regulating mechanism 500), the retraction biasing member is permitted to expand in the proximal direction from its initial energized state. This axial expansion in the proximal direction of the retraction biasing member retracts the needle. If an inserter needle/trocar and cannula configuration are utilized, retraction of the needle may occur while maintaining the cannula in fluid communication with the body of the user. Accordingly, the insertion mechanism may be used to insert a needle and cannula into the user and, subsequently, retract the needle while retaining the cannula in position for drug delivery to the body of the user.

As further discussed below, in some examples, the power and control system 800 and/or the drive control system 820 may control the needle insertion mechanism 200 via the multi-function drive mechanism 100. Additionally, the power and control system 800 and/or the drive control system 820 may control the rate of drug delivery via the drive mechanism 100 and regulating mechanism 500 such as by metering, providing resistance, or otherwise preventing free axial translation of the plunger seal utilized to force a drug substance out of a drug container (thereby delivering drug substances at variable rates and/or delivery profiles).

Referring back to FIGS. 2A-2E and 3A-3D, the multi-function drive mechanisms 100 may concurrently or sequentially perform the steps of: triggering a needle insertion mechanism to provide a fluid pathway for drug delivery to a user; and connecting a sterile fluid pathway to a drug container to permit fluid flow from the drug container to the needle insertion mechanism for delivery to the user.

In at least one embodiment, as shown in FIGS. 2A-2E and 3A-3D, the control unit 810 may initiate motion of the actuator 101 of the drive control system 820, which may cause rotation of the main/star gear 102 of the multi-function drive mechanism 100. Main/star gear 102 is shown as a compound gear with aspects 102A and 102B (see FIG. 4). In one example, main/star gear 102 conveys motion to the regulating mechanism 500 through gear assembly 516.

In another example, main/star gear 102 conveys motion to the needle insertion mechanism 200 through gear 112. As gear 112 is rotated by main/star gear 102, gear 112 engages the needle insertion mechanism 200 to initiate the fluid pathway connection into the user, as described in detail above. In one particular embodiment, needle insertion mechanism 200 is a rotational needle insertion mechanism. Accordingly, gear 112 is configured to engage a corresponding gear surface 208 of the needle insertion mechanism 200 (see FIGS. 2A and 3B). Rotation of gear 112 causes rotation of needle insertion mechanism 200 through the gear interaction between gear 112 of the drive mechanism 100 and corresponding gear surface 208 of the needle insertion mechanism 200. Once suitable rotation of the needle insertion mechanism 200 occurs, for example rotation along axis 'R' shown in FIG. 2B-2C, the needle insertion mechanism may be initiated to create the fluid pathway connection into the user.

Figure 7A:
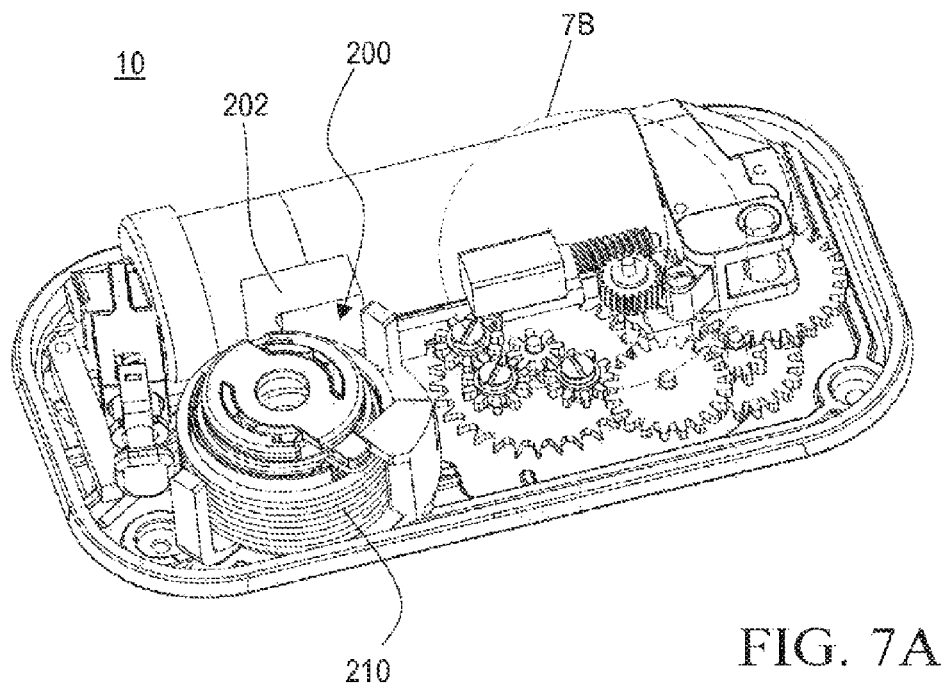
FIG. 7A shows an isometric view of a drug delivery pump in which the insertion mechanism includes a rotational biasing member and the drive mechanism includes a worm gear.

In an alternative embodiment, as shown in FIG. 7A, the insertion mechanism 200 includes a rotationally biased member 210 which is initially held in an energized state. In one example, the rotationally biased member is a torsional spring. The drive control system 820 may actuate one or more components of the multi-function drive mechanism 100, insertion mechanism 200 and/or the regulating mechanism 500 to prevent and/or control the rotation of the rotational biasing member 210.

The gear 112 may be configured to engage a corresponding gear surface of a control arm 202 (visible in FIG. 7B) that contacts or blocks the needle insertion mechanism 200. Rotation of gear 112 causes movement of the control arm 202, which may initiate or permit rotation of needle insertion mechanism 200.

Moreover, the rotational biasing member may be prevented from de-energizing by contact of a component of the insertion mechanism with a rotation prevention feature, such as a blocking aspect of the control arm, of the drug pump. In one example, the rotational biasing member 210 may be prevented from de-energizing by interaction of gear surface 208 with gear 112.

Figure 10:
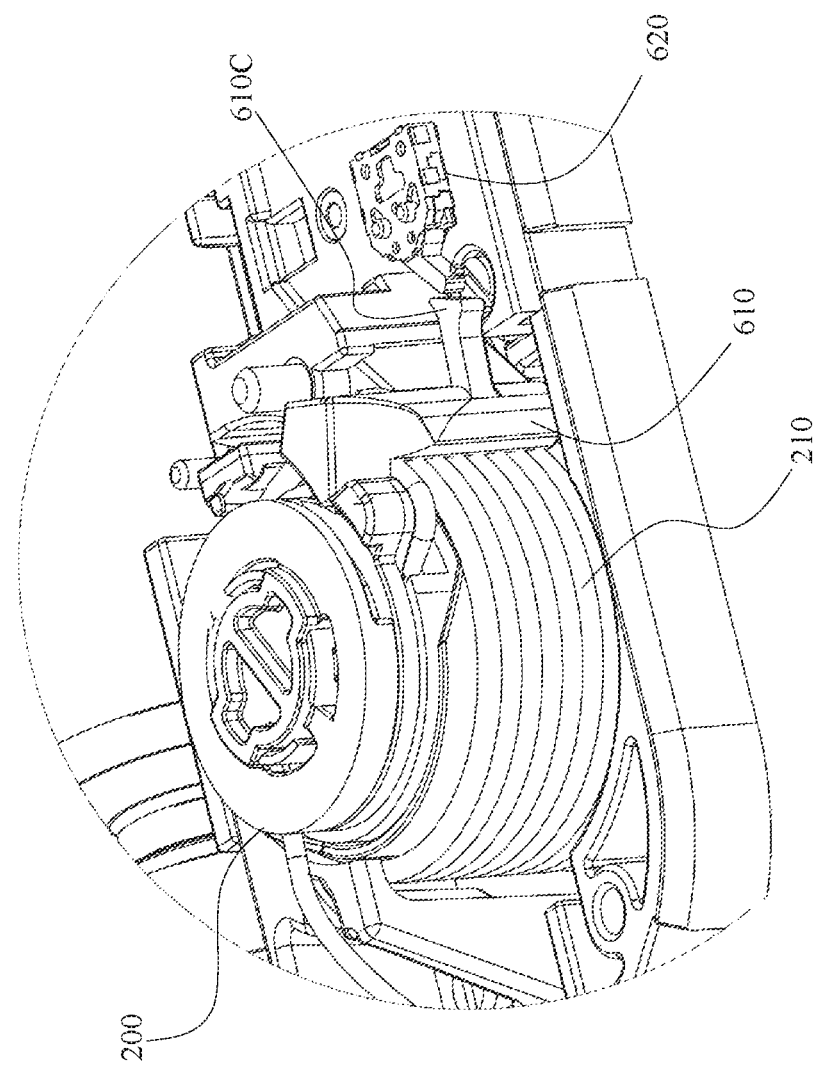
FIG. 10 is a detailed isometric view of a needle insertion mechanism according to at least one embodiment of the present invention.

Additionally, or alternatively, the needle insertion mechanism may be mechanically activated. For example, the rotational biasing member 210 may be caused to de-energize upon depression of the activation button 14. As described in more detail in International Patent Application Publication Number WO 2016/130679, which is incorporated herein by reference, depression of activation button 14 may allow rotation of NIM retainer 610. This rotation of NIM retainer 610 allows de-energizing of biasing member 210 and insertion of a cannula into the patient. In addition, as shown in FIG. 10, extension 610C of NIM retainer 610 may contact status switch 620, thereby providing a signal to power and control system 800 that needle insertion has been activated. This signal may, as described herein, trigger a number of functions of power and control system 800, including the entering of a delay mode. Embodiments of the mechanical activation of the needle insertion may be found in International Patent Application Publication WO 2016/130679, which is incorporated herein by reference.

It is contemplated that, in one example, at least the prevention of the rotation of the rotational biasing member 210 may be implemented prior to the on-body sensing. As such, when the on-body sensor 840 senses skin portion of the user, and/or the power and control system 800 receives input for initiation of the drug delivery (e.g., via the activation button) and/or input for needle insertion, the power and control system 800 may command the drive control system 820 to permit the rotationally biased member 210 to, at least partially, de-energize. This may cause one or more components of the insertion mechanism 200, drive control mechanism 100 and/or regulating mechanism 500 to rotate and, in turn, cause, or allow, the insertion of the needle into the patient. Furthermore, a cannula may be inserted into the patient as described above.

As detailed below, during the delivery of the drug, based on the interactions among the drive control system 820, the drive mechanism 100 and the regulating mechanism 500, the insertion mechanism may be further controlled. For example, when the control arm or another component of the drive control system 820 recognizes a slack in the tether, the rotationally biased member may be allowed to further de-energize, causing additional rotation of one or more components of the insertion mechanism 200.

This rotation may cause, or allow, the drive control system 820 to retract the needle from the patient. The needle may be fully retracted in a single step or there may be multiple steps of retraction.

In at least one embodiment, the needle insertion mechanism 200 may be configured such that a particular degree of rotation upon rotational axis 'R' (shown in FIGS. 2B-2C) enables the needle/trocar to retract as detailed above. Additionally or alternatively, such needle/trocar retraction may be configured to occur upon a user-activity or upon movement or function of another component of the drug pump. In at least one embodiment, needle/trocar retraction may be configured to occur upon end-of-drug-delivery, as triggered by, for example, the regulating mechanism 500 and/or one or more of the sensors (e.g., the tether sensor, pressure sensor, etc.) During these stages of operation, delivery of fluid substances from the drug chamber 21 may be initiated, on-going, and/or completed by the expansion of the biasing member 122 from its initial energized state acting upon the piston 110 and plunger seal 60.

Figure 17A:
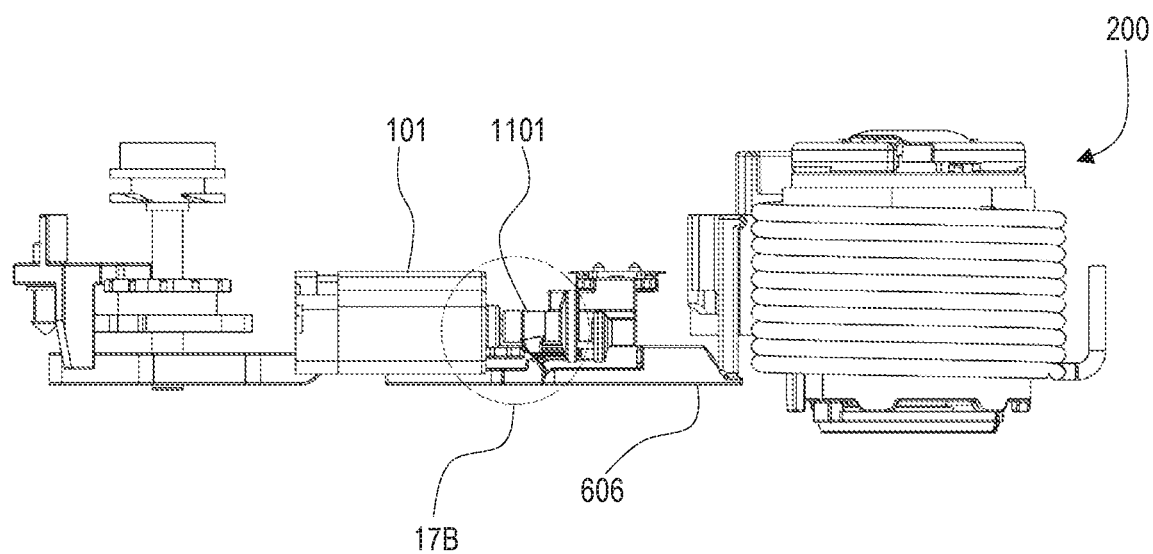
FIG. 17A is a side elevation view of an enabling mechanism according to at least one embodiment of the present invention.
Figure 17B:
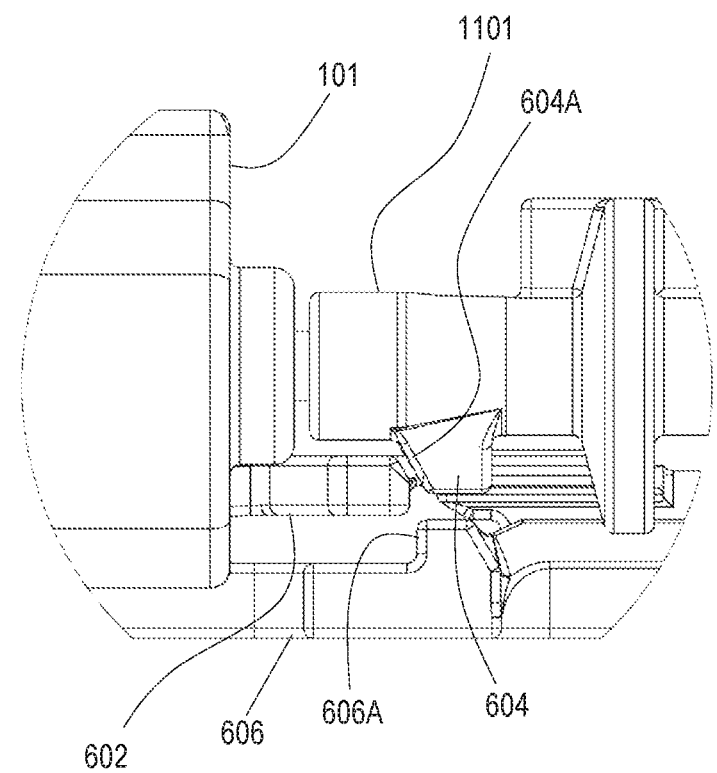
FIG. 17B is an enlarged, fragmentary side elevation view of the enabling mechanism of FIG. 17A.

In one embodiment, translation of the activation mechanism may be a part of, or operate, a NIM activation mechanism. The NIM activation mechanism may include an enabling mechanism as shown in FIGS. 17A-17B. In this embodiment, translation of the activation mechanism 14 may be directly or indirectly coupled to a slide 602. In a first configuration, the enabling mechanism is configured such that translation of the activation mechanism and slide does not cause activation of the needle insertion mechanism 200 or sterile fluid pathway connection 300.

FIGS. 17A-17B illustrate the enabling mechanism configured such that translation of the activation mechanism 14 (See FIG. 1A) and slide 602 causes activation of the needle insertion mechanism 200. Transformation of the enabling mechanism from the first configuration to the second configuration may be initiated by, for example, triggering of an on-body sensor, or by the elapsing of a predetermined amount of time after power-on of the device. The transformation of the enabling mechanism from the first to the second configuration may be performed by rotation of the actuator 101 which may cause a selector member 604 to become aligned with an aspect of the slide 602. The selector member 604 may include a ramped surface 604A which is configured to contact a portion of the slide 602 upon translation of the activation mechanism 14 and slide 602. The selector member 604 may be mounted to or be an integral portion of the gear interface such as key 1101. Contact of the slide 602 with the selector member 604 may cause the slide 602 to be displaced such that a portion of the slide is aligned with a portion of a throw arm or control arm 606, such as protrusion 606A. In this configuration, translation of the activation mechanism 14 causes translation of the throw arm 606. Translation of the throw arm 606 causes activation of the needle insertion mechanism 200 to insert the fluid path into the target. During manufacturing, transportation, and storage, the enabling mechanism is in the first configuration in which depression of the activation mechanism 14 does not activate the needle insertion mechanism 200. In this way, the needle insertion mechanism is prevented from activating prematurely. Contact of the slide 602 with the selector member 604 may cause substantially rigid body displacement of the slide or, alternatively, the contact may cause a deformation of the slide. For example, the slide may include a deformable (i.e., less rigid) portion which may be displaced by the contact. At step 930 (see FIG. 9B) the enabling mechanism may be caused to enter this configuration, in order to allow NIM activation. With the enabling mechanism in this configuration, depression of activation button 14 may constitute step 932.

One example of a NIM activation mechanism is shown in FIGS. 11A-16B. For clarity, a number of components of the drug delivery device are hidden in these figures. The NIM activation mechanism includes: a slide 602, a throw arm 606, a NIM interlock 608, and a NIM retainer 610. Initially, as shown in FIGS. 11A-12B, the NIM retainer 610 is positioned such that the NIM retainer 610 is in contact with a protrusion 204 of the NIM 200 such that the protrusion 204 is prevented from rotating about axis R (see FIG. 13B), thereby preventing activation of the NIM 200. In the embodiment shown, the NIM retainer 610 is configured for rotational movement about axis B (see FIG. 15B). The NIM retainer 610 may, for example, be mounted to the housing 12 at the bore 610A. For example, a pin or shaft may be disposed in bore 610A around which the NIM retainer 610 may rotate. The pin or shaft may an integral portion of the housing 12 or, alternatively, may be a separate component. The NIM retainer 610 is prevented from rotating by contact between an arm 610B of the NIM retainer 610 with the NIM interlock 608. The NIM interlock 608 is disposed for translational motion (in the direction of the hatched arrow of FIG. 11B) and is initially held in position by a flex arm. The NIM interlock 608 is initially in a first position in which it is in contact with or adjacent to a lower surface 606B of the throw arm 606.

Figure 11A:
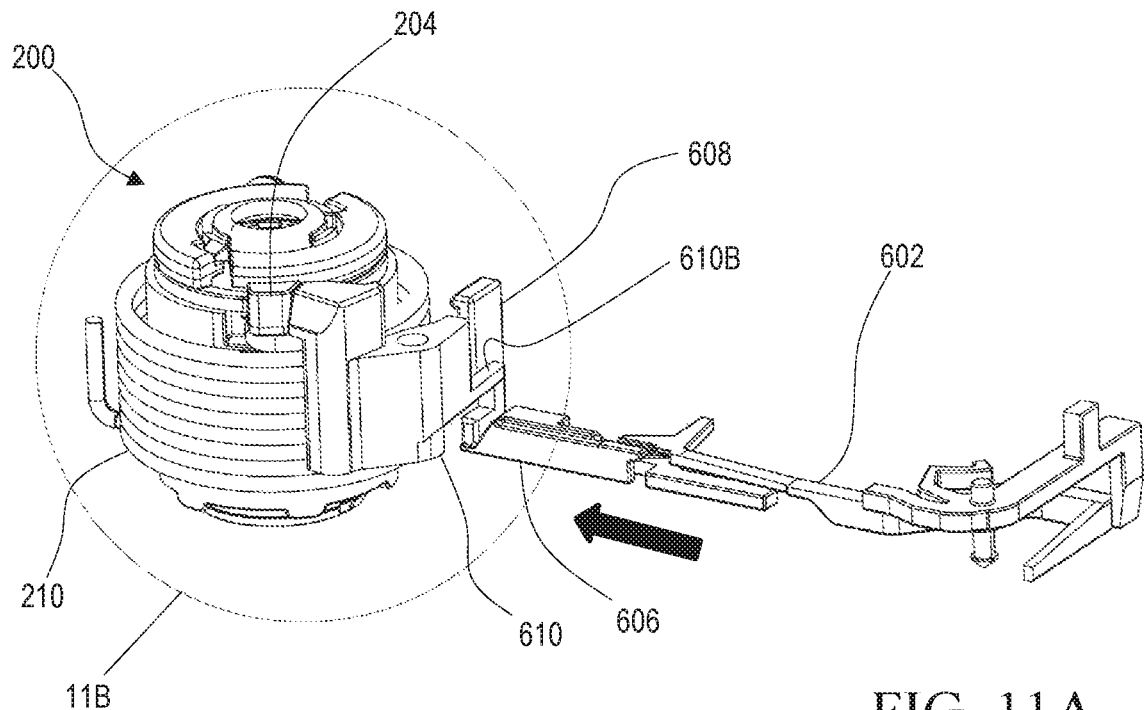
FIG. 11A is an isometric view of an insertion mechanism in an initial configuration.
Figure 11B:
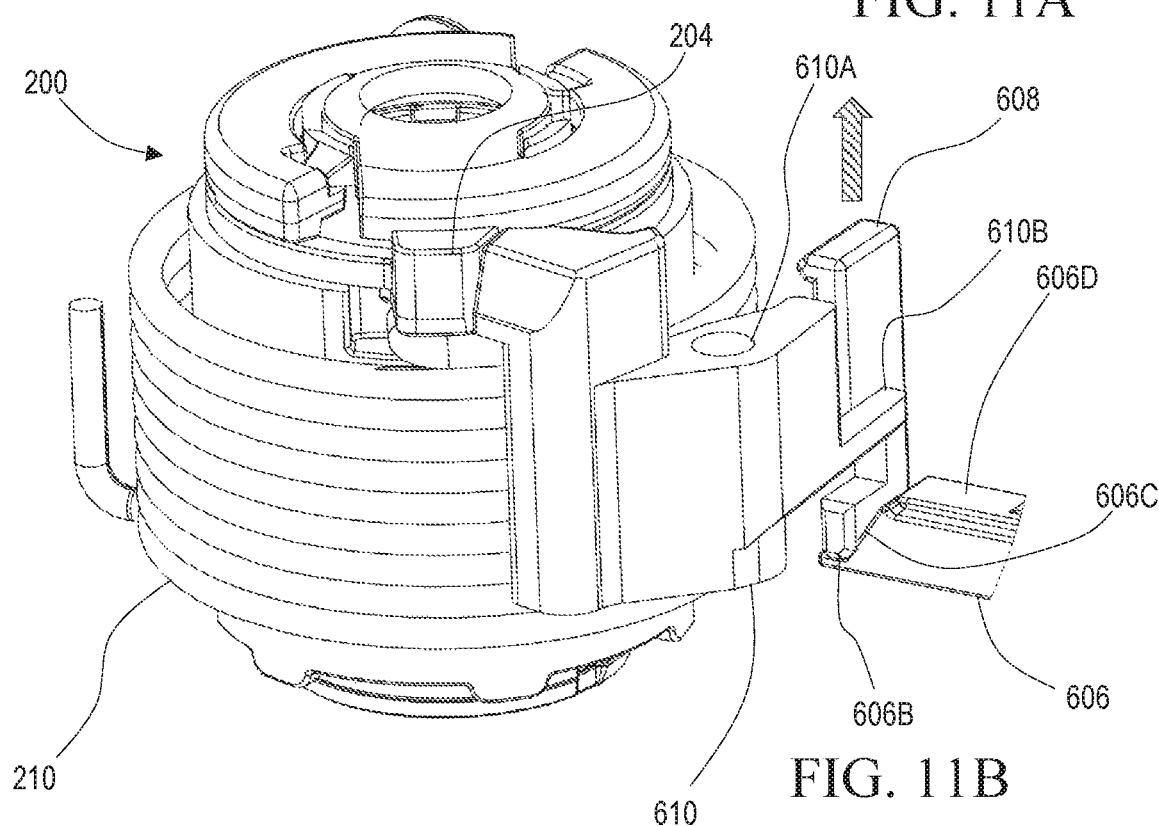
FIG. 11B is an enlarged, fragmentary isometric view of the insertion mechanism of FIG. 11A.
Figure 12A:
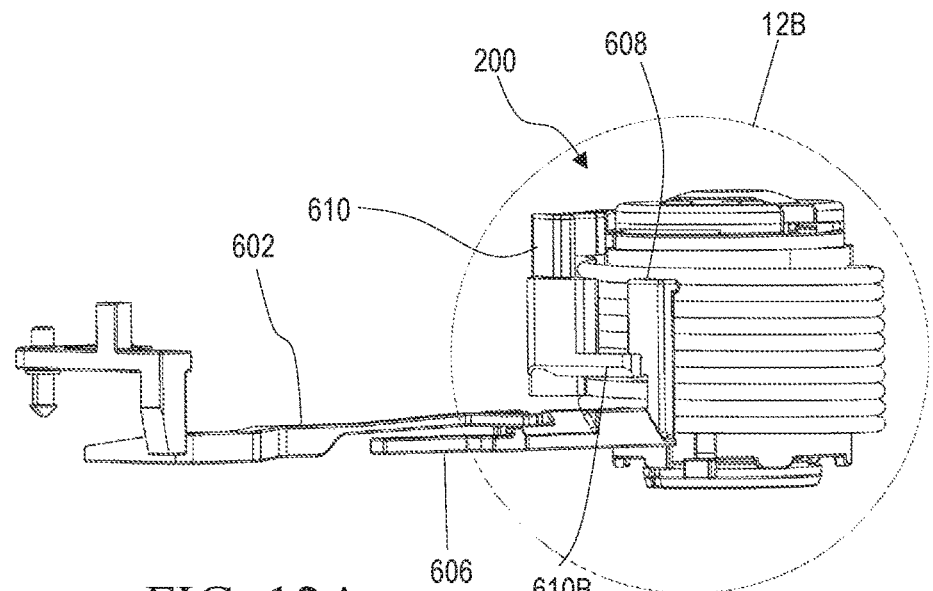
FIG. 12A is a side elevation view of the insertion mechanism of FIG. 11A in an initial configuration.
Figure 12B:
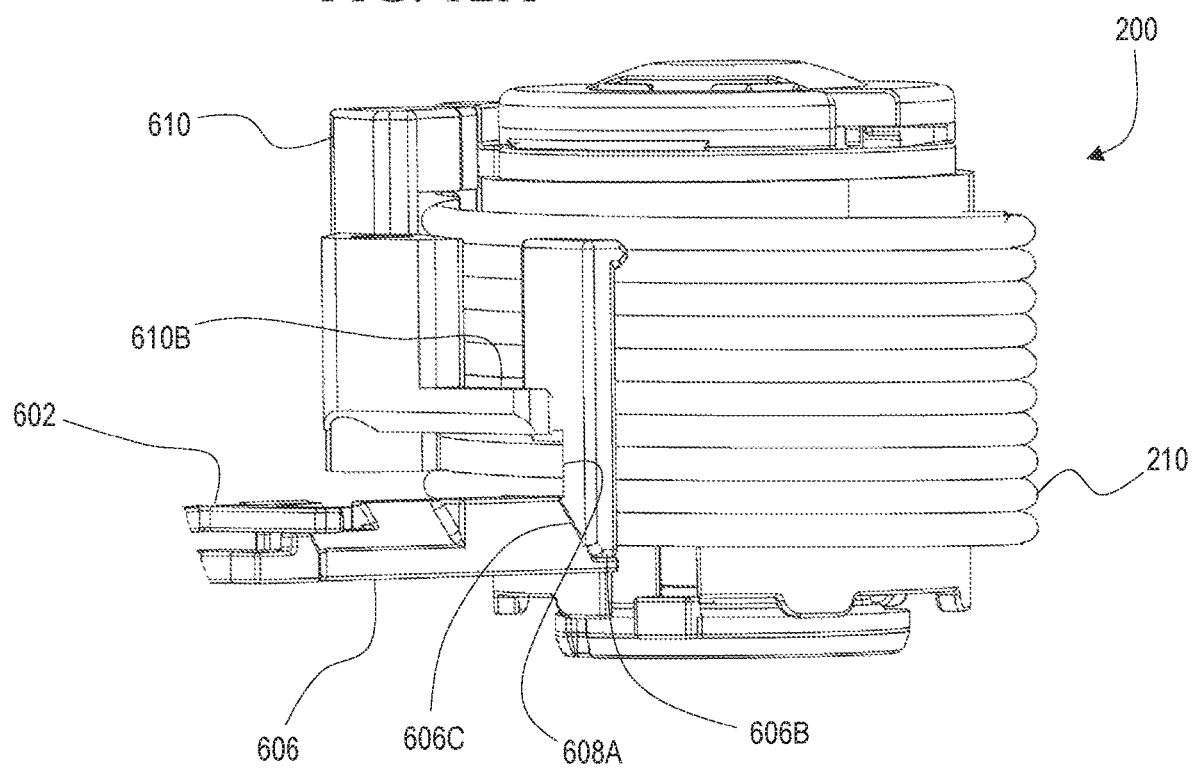
FIG. 12B is an enlarged, fragmentary, side elevation view of the insertion mechanism of FIG. 12A.
Figure 13A:
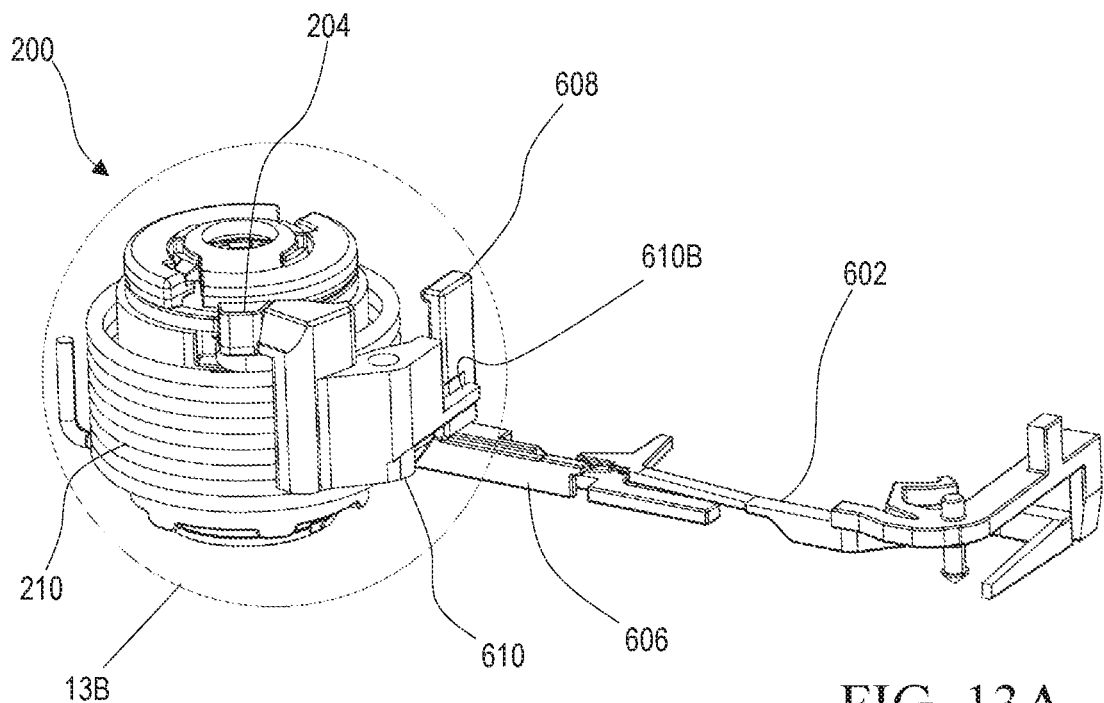
FIG. 13A is an isometric view of the insertion mechanism of FIG. 11A in an intermediate configuration.
Figure 13B:
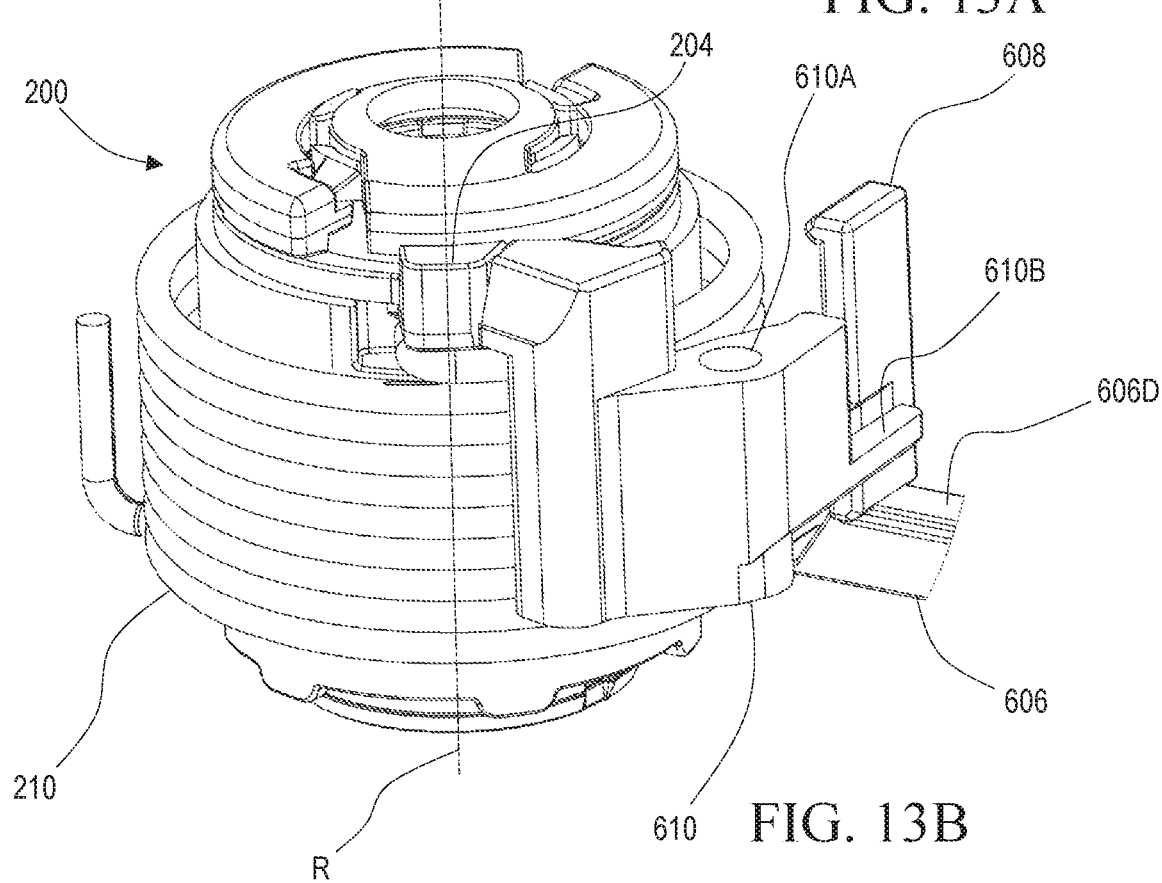
FIG. 13B is an enlarged, fragmentary isometric view of the insertion mechanism of FIG. 13A.
Figure 14A:
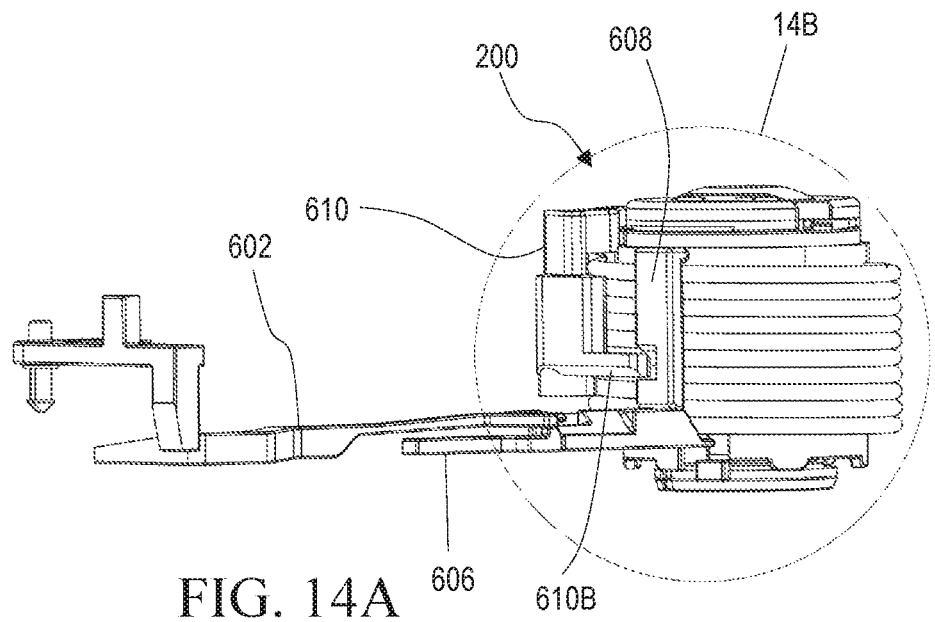
FIG. 14A is a side elevation view of the insertion mechanism of FIG. 11A in an intermediate configuration.
Figure 14B:
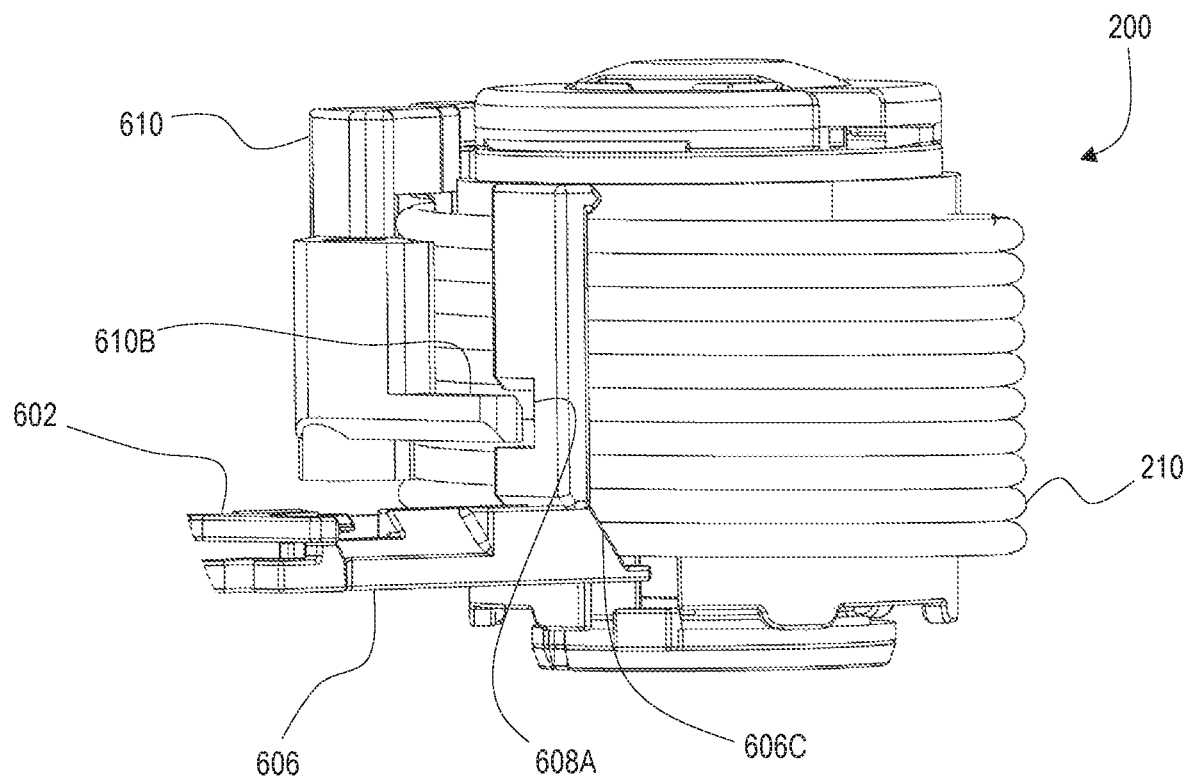
FIG. 14B is an enlarged, fragmentary, side elevation view of the insertion mechanism of FIG. 14A.
Figure 15A:
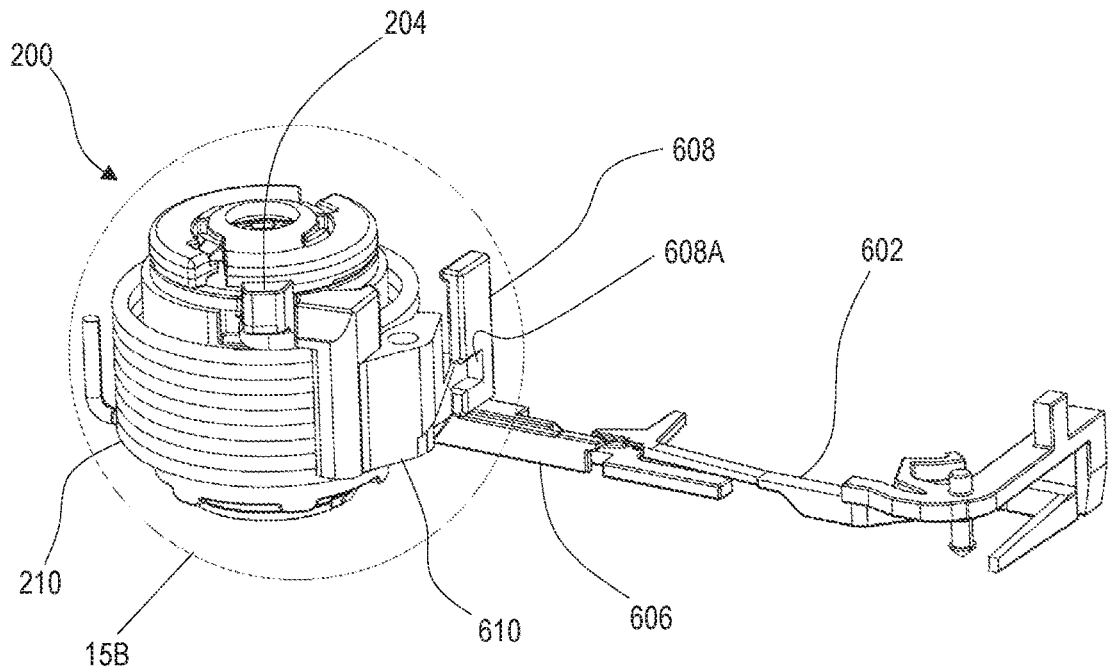
FIG. 15A is an isometric view of the insertion mechanism of FIG. 11A in a released configuration.
Figure 15B:
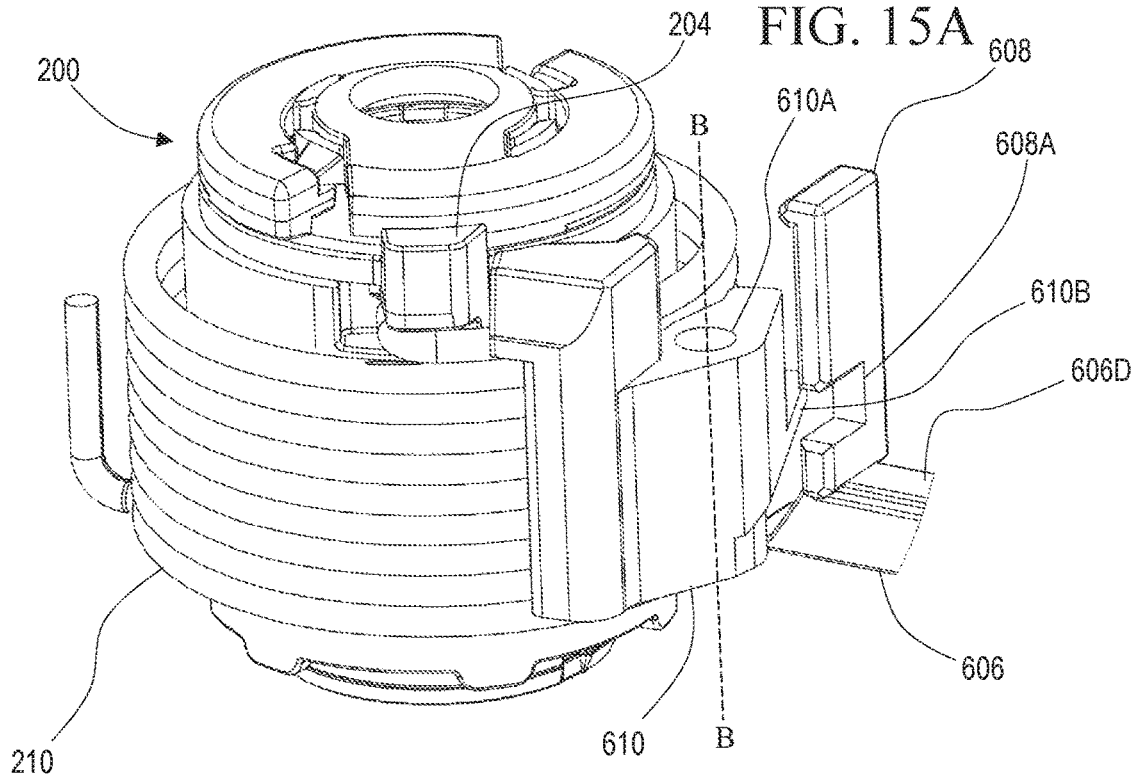
FIG. 15B is an enlarged, fragmentary isometric view of the insertion mechanism of FIG. 15A.
Figure 16A:
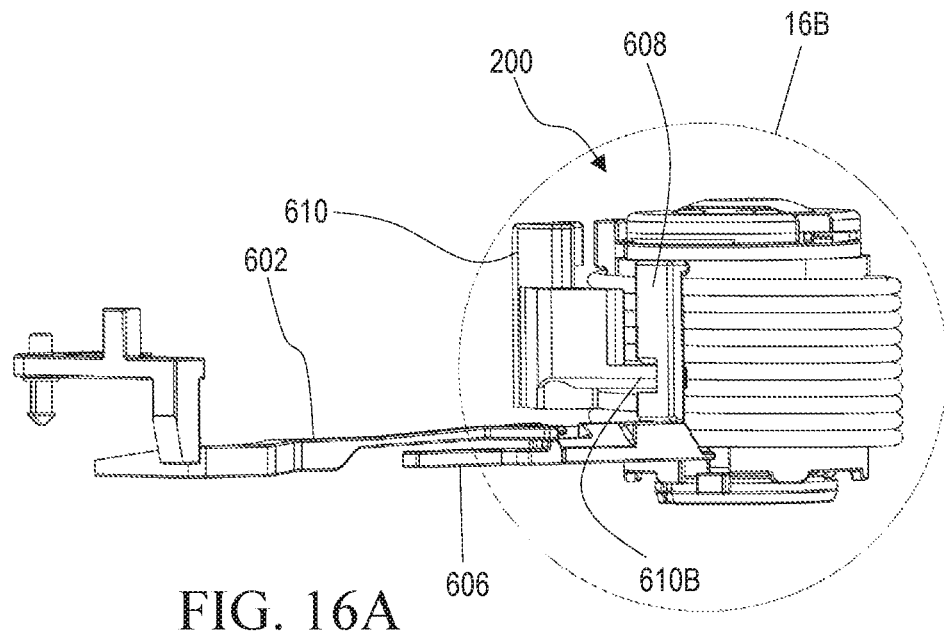
FIG. 16A is a side elevation view of the insertion mechanism of FIG. 11A in a released configuration.
Figure 16B:
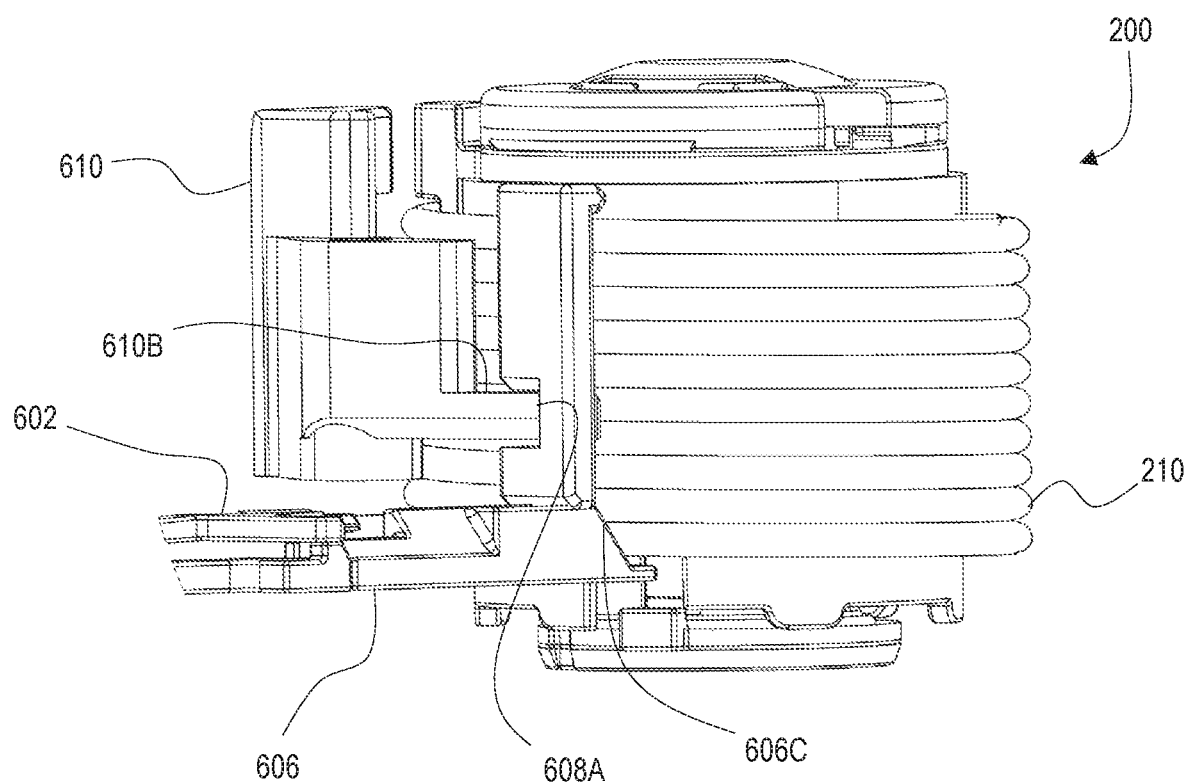
FIG. 16B is an enlarged, fragmentary, side elevation view of the insertion mechanism of FIG. 16A.

With the selector member 604 in the second configuration (shown in FIGS. 17A-17B) depression of the activation mechanism 14 causes translation of the throw arm 606 as described above (in the direction of the solid arrow in FIG. 11A). The ramped surface 606C of the throw arm 606 contacts the NIM interlock 608 and causes the NIM interlock 608 to translate in a direction substantially orthogonal to the direction of translation of the throw arm 606. FIGS. 13A-14B show the position of the throw arm 606 and NIM interlock 608 after translation of the throw arm. As shown, in this configuration, the NIM interlock 608 is positioned adjacent to or in contact with an upper surface 606D of the throw arm 606. The window 608A of the NIM interlock 608 is aligned with the arm 610B of the NIM retainer 610. Hence, as shown in FIGS. 15A-16B, the NIM retainer 610 is able to rotate about axis B. The contact surfaces of protrusion 204 and retainer 610 may be configured such that the protrusion 204 applies a rotational force to NIM retainer 610, thereby causing rotation of NIM retainer 610 about axis B. Alternatively, or additionally, the NIM retainer 610 may be biased to rotate by a biasing member. The biasing member may be, for example, a torsion spring. Rotation of the NIM retainer 610 causes the NIM retainer 610 to disengage the protrusion 204 of the NIM 200. Hence, the NIM 200 is able to activate to insert a fluid path into a target.

In other embodiments, the NIM interlock 608 may directly engage a portion of the NIM 200, such as the protrusion 204, to initially prevent activation of the NIM 200. Translation of the NIM interlock 608 in the direction orthogonal to the translation of the throw arm 606 may cause the NIM interlock 608 to disengage the NIM 200 and allow the NIM 200 to activate. Also, while the slide 602 and the throw arm 606 are shown here as separate components, it is contemplated that these can be combined into a single, unified component. In such an embodiment, the selector member may initially be configured to prevent translation of the slide and/or throw arm.

In another embodiment, the throw arm 606 is engaged with a portion of the NIM whereby translation of the throw arm 606 allows activation of the NIM 200.

Additionally or alternatively, the drive control system 820 may indirectly engage the needle insertion mechanism 200 in order to establish the sterile fluid connection sub-system 300, as described below.

Fluid Pathway Connection

The power and control system 800 and/or drive control system 820 may additionally establish the fluid pathway connection or sub-system 300 by connecting the sterile fluid conduit to the drug container, to enable the fluid pathway connection.

The establishment of the fluid pathway connection 300 may be performed prior to, during, or after the wait time period. Additionally, the pathway connection 300 may be established prior to, or during the actuation of the insertion mechanism 200. In some embodiments, the power and control system 800 may cause the establishment of the fluid pathway connection 300 via the multi-function drive mechanism 100, and/or one of the other sub-systems such as the needle insertion mechanism or sub-system 200. Generally, a suitable fluid pathway connection includes a sterile fluid conduit, a piercing member, and a sterile sleeve attached to a drug container or a sliding pierceable seal integrated within a drug container. The fluid pathway connection may further include one or more flow restrictors. Upon activation of the device 10, the fluid pathway connection 300 is established to connect the sterile fluid conduit to the drug container of the drive mechanism 100. Such connection may be facilitated by a piercing member, such as a needle, penetrating a pierceable seal of the drug container of the drive mechanism 100. The sterility of this connection may be maintained by performing the connection within a flexible sterile sleeve. Upon substantially simultaneous activation of the insertion mechanism 200, the fluid pathway between drug container and insertion mechanism is complete to permit drug delivery into the body of the user. In one such embodiment, the fluid pathway connection may be substantially similar to that described in International Patent Application No. PCT/US2012/054861, which is included by reference herein in its entirety for all purposes. In such an embodiment, a compressible sterile sleeve may be fixedly attached between the cap of the drug container and the connection hub of the fluid pathway connection. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connection may be integrated into a drug container as described in International Patent Applications No. PCT/US2012/054861, PCT/US2013/030478, No. PCT/US2014/052329, or PCT/US2016/020486, for example, which are included by reference herein in their entirety for all purposes.

According to such an embodiment, a drug container 50 may have a drug chamber 21 within a barrel between a pierceable seal (not shown) and a plunger seal 60. A drug fluid is contained in the drug chamber 21. Upon activation of the device by the user, a drive mechanism (e.g., multi-function drive mechanism 100) asserts a force on a plunger seal 60 contained in the drug container. As the plunger seal 60 asserts a force on the drug fluid and any air/gas gap or bubble, a combination of pneumatic and hydraulic pressure builds by compression of the air/gas and drug fluid and the force is relayed to the sliding pierceable seal. The pierceable seal is caused to slide towards the cap 52, causing it to be pierced by the piercing member retained within the integrated sterile fluid pathway connection. Accordingly, the integrated sterile fluid pathway connection is connected (i.e., the fluid pathway is opened) by the combination pneumatic/hydraulic force of the air/gas and drug fluid within the drug chamber created by activation of a drive mechanism 100. Once the integrated sterile fluid pathway connection is connected or opened, drug fluid is permitted to flow from the drug container 50, through the integrated sterile fluid pathway connection 300, sterile fluid conduit, and insertion mechanism 200, and into the body of the user for drug delivery. In at least one embodiment, the fluid flows through only a manifold and a cannula and/or needle of the insertion mechanism, thereby maintaining the sterility of the fluid pathway before and during drug delivery.

In one embodiment, the power and control system 800 may command the drive control system 820 to establish or activate the sterile fluid pathway subsystem or connection 300. For example, the connection 300 may be established via the needle insertion mechanism 200 which may be activated or controlled by the multi-function drive mechanism 100.

Additionally or alternatively, the sterile fluid pathway connection 300 may be directly initiated by the multi-function drive mechanism 100. For example, the control unit 810 may command the motor 101 to actuate a rotational gear, such as the star gear 102 described in detail herein, that may operate concurrently or sequentially to: (a) control the rate of drug delivery, (b) to actuate the needle insertion mechanism 200, and/or (c) initiate the sterile fluid pathway connection 300, based on various predetermined times (e.g., the wait time period, the drug delivery period) as provided by the power and control system 800.

In one embodiment, shown in FIGS. 1A-1C, the multi-function drive mechanism 100 performs all of these steps substantially concurrently. In that embodiment, the drive control system 820 causes the multi-function drive mechanism 100 to rotate a gear (e.g., star gear 102) that acts upon several other components (e.g., other gear assemblies). For example, the gear acts on a gear assembly to control the rate of drug delivery, while also contacting a needle insertion mechanism 200 to introduce a fluid pathway connection 200 into the user. As the needle insertion mechanism 200 is initiated, the sterile fluid connection is made to permit drug fluid flow from the drug container 50, through the fluid conduit, into the needle insertion mechanism 200, for delivery into the patient as the gear and gear assembly of the multi-function drive mechanism control the rate of drug delivery.

It will be appreciated that, the drug pump device 10 is configured to deliver a range of drugs with different viscosities and volumes via the established sterile fluid pathway subsystem or connection 300. In addition, the drug pump device 10 delivers a drug at a controlled flow rate (speed) and/or of a specified volume. In one embodiment, the drug delivery process is controlled by one or more flow restrictors (not shown) within the fluid pathway connection and/or the sterile fluid conduit. In other embodiments, other flow rates may be provided by varying the geometry of the fluid flow path or delivery conduit As shown in FIGS. 2A-2D and 3A-3D, rotation of the needle insertion mechanism 200 in this manner may also cause a connection of a sterile fluid pathway to a drug container to permit fluid flow from the drug container to the needle insertion mechanism for delivery to the user. In such an example, the control unit 810 may command and control: (a) drive mechanism 100, (b) the needle insertion mechanism 200, and (c) the sterile fluid pathway connection 300. For example, ramp aspect 222 of needle insertion mechanism 200 is caused to bear upon a movable connection hub 322 of the sterile fluid pathway connection 300. As the needle insertion mechanism 200 is rotated by the multi-function drive mechanism 100 (based on the control unit 810 command), ramp aspect 222 of needle insertion mechanism 200 bears upon and translates movable connection hub 322 of the sterile fluid pathway connection 300 to facilitate a fluid connection therein.

Regulating Mechanism 500 AND Multi-Function Drive Mechanism 100

Moreover, the drug pump device 10 may control the flow rate of the drug. In one example, the flow rate may be controlled by the drive control system 820 (e.g., the motor of the drive control system) by varying the speed at which one or more components of the drive mechanism 100 advances into the drug container 50 to dispense the drug. It is noted that, a combination of the different flow rate control methods may be implemented to control the flow of the drug via the sterile fluid pathway connection 300.

The power and control system 800 (e.g., the control unit 810) may send command signal to the drive control system 820 to control the flow rate control sub-system or regulating mechanism 500 via the multifunction drive mechanism 100 as discussed below. The rate of drug delivery as controlled by the drive control system 820 may be determined by: selection of the gear ratio of gear assembly 516; selection of the main/star gear 102; selection of the diameter of winding drum/gear 520 and further driving such elements by commanding the actuator 101 to control the rate of rotation of the main/star gear 102; or any other method known to one skilled in the art. By using electromechanical actuator 101 to control and adjust the rate of rotation of the main/star gear 102, it may be possible to configure the drug pump device 10 to provide a variable dose rate (i.e., the rate of drug delivery is varied during a treatment).

Additionally, the drive control system 820 may control the regulating mechanism or sub-system 500 which may include controlling the rate of drug delivery by metering, providing resistance, or otherwise preventing free axial translation of the plunger seal utilized to force a drug substance out of a drug container.

With references to the embodiments shown in FIGS. 2A-2D and 3A-3D, the power and control system 820 may control the drive mechanism 100 via the motor 101. The drive mechanism 100 may include a gear assembly 116 including a main gear 102, a drive housing 130, and a drug container 50 having a cap 52, a pierceable seal (not visible), a barrel 58, and a plunger seal 60. The main gear 102 may be, for example, a star gear disposed to contact multiple secondary gears or gear surfaces. A drug chamber 21, located within the barrel 58 between the pierceable seal and the plunger seal 60, may contain a drug fluid for delivery through the insertion mechanism and drug pump into the body of the user. The seals described herein may be comprised of a number of materials but are, in a preferred embodiment, comprised of one or more elastomers or rubbers. The drive mechanism 100 may further contain one or more drive biasing members, one or more release mechanisms, and one or more guides, as are described further herein. The components of the drive mechanism 100 function to force a fluid from the drug container out through the pierceable seal, or preferably through the piercing member of the fluid pathway connection 300, for delivery through the fluid pathway connection, sterile fluid conduit, and insertion mechanism into the body of the user.

In one particular embodiment, the drive mechanism 100 employs one or more compression springs as the drive biasing member(s) 122. In such embodiment, upon the activation of the drug pump by the user (e.g., via the activation button) the power and control system 800 may be configured to directly or indirectly (and electromechanically) release the drive biasing members 122 from an energized state. Upon release, the drive biasing members 122 may bear against and act upon the plunger seal 60 to force the fluid drug out of the drug container. The compression spring may bear against and act upon a piston which, in turn, acts upon the plunger seal 60 to force the fluid drug out of the drug container. In one example, one or more drive biasing members 122 may be compressed between the drive housing 130 and piston 110, wherein the drive biasing members 122 may bear upon an interface surface of the piston 110.

Optionally, a cover sleeve (not shown) may be utilized between the drive biasing members 122 and the interface surface of the piston 110 for example, to promote even distribution of force from the drive biasing member 122 to the piston 110, prevent buckling of the drive biasing members 122, and/or hide biasing members 122 from user view. Interface surface of piston 110 is caused to rest substantially adjacent to, or in contact with, a proximal end of seal 60. Although the embodiments shown in FIGS. 2A-2D and 3A-3D show a singular biasing member it is also contemplated that one or more biasing members disposed to act in parallel may be used.

As discussed below, in some embodiments, the drive control system 820 and/or the power and control system 800 may control the delivery rate of the drug via the drive mechanism 100, insertion mechanism 200 and the regulating mechanism 500.

Figure 2A:
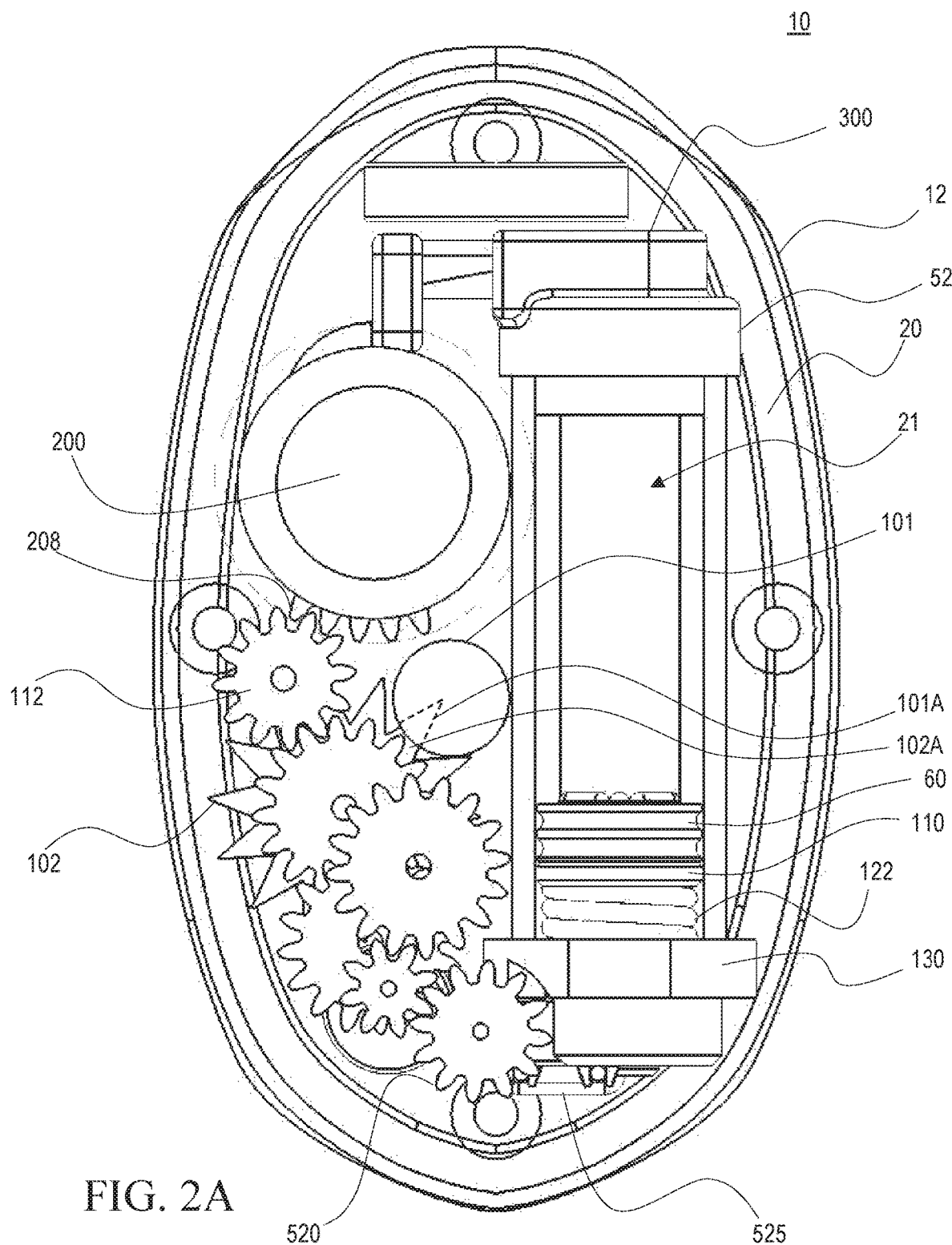
FIG. 2A shows a top view of the interior components of a drug delivery pump according to at least one aspect of the present invention.
Figure 2B:
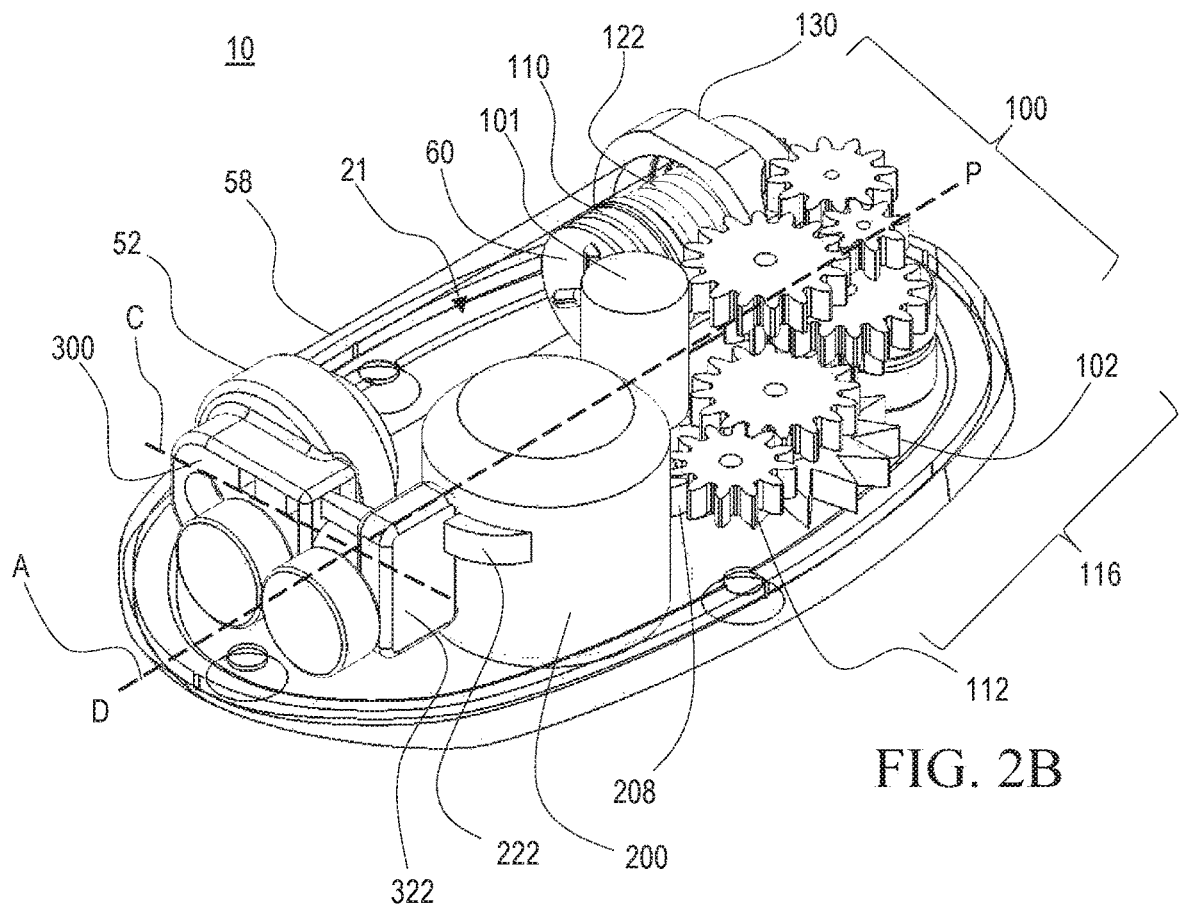
FIG. 2B shows an isometric view of a multi-function drive mechanism, according to at least one embodiment of the present invention prior to activation.
Figure 2C:
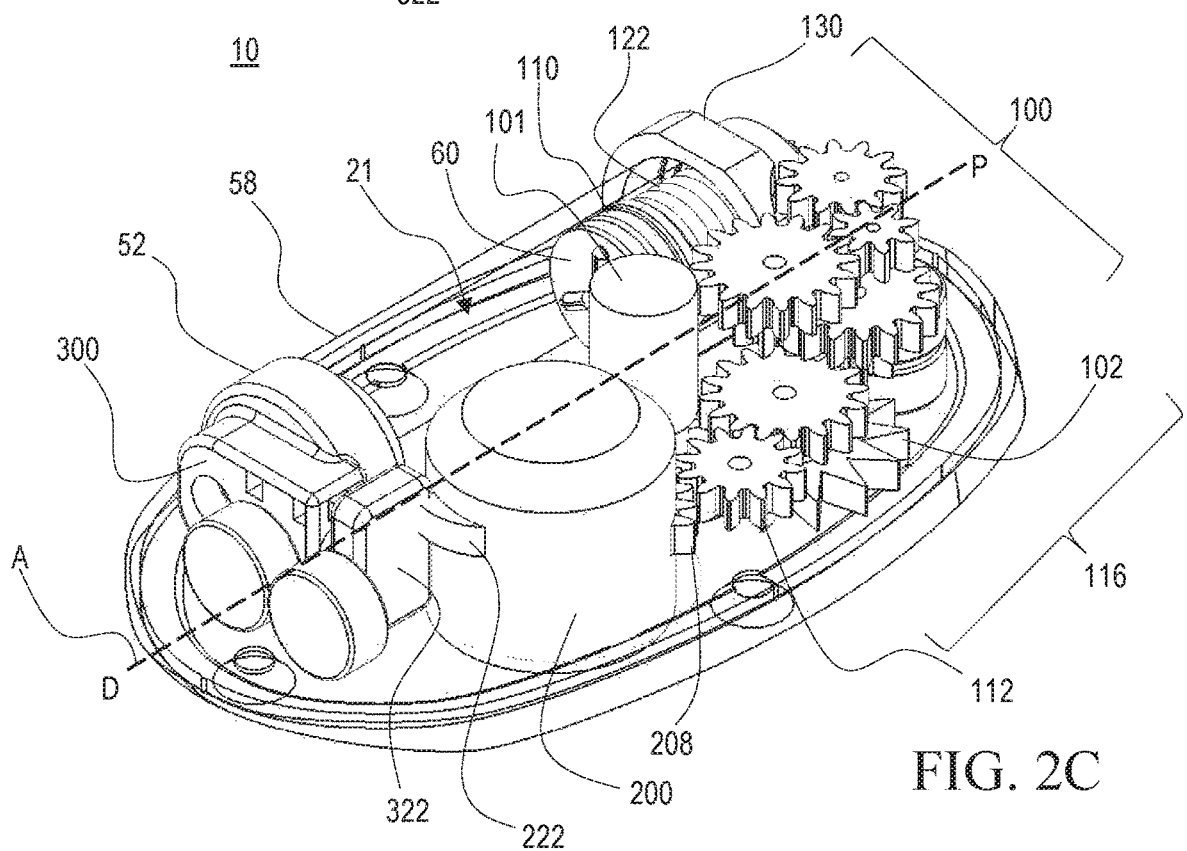
FIG. 2C shows an isometric view of a multi-function drive mechanism, according to at least one embodiment of the present invention during activation.
Figure 2D:
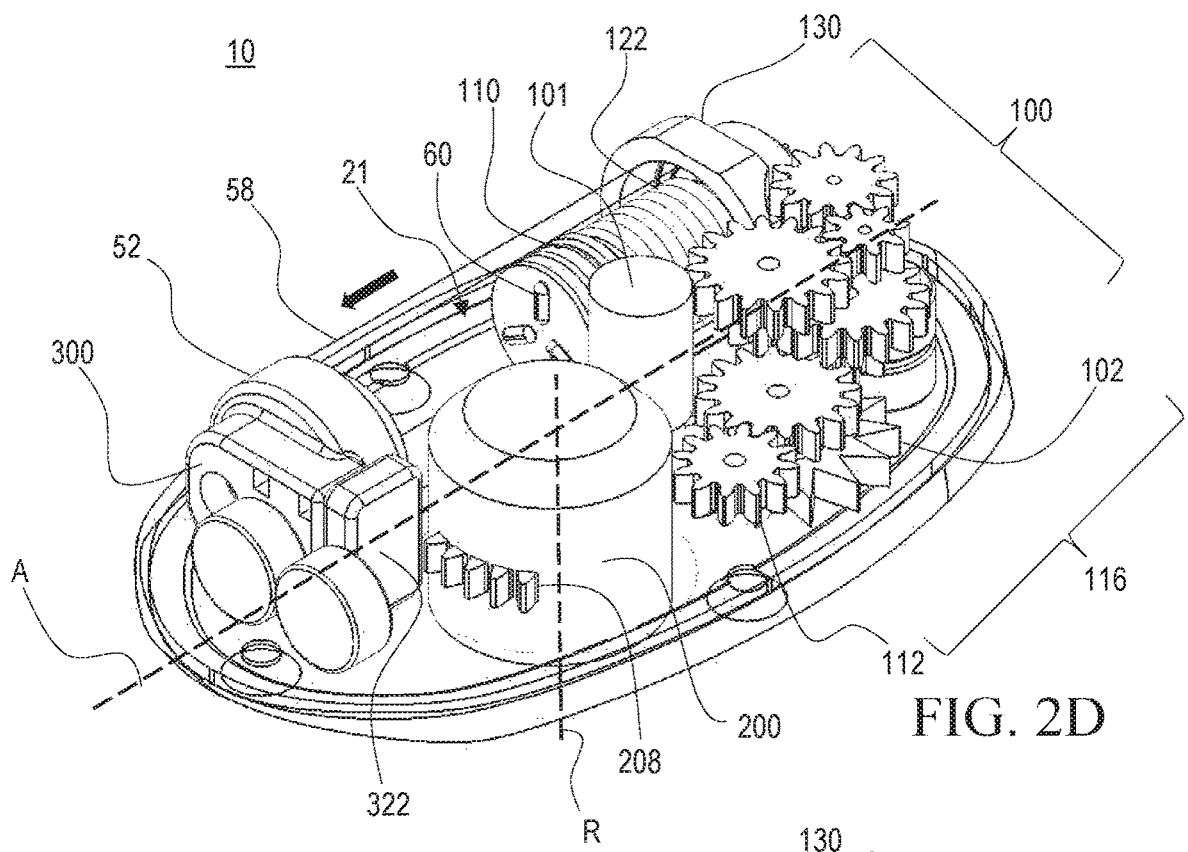
FIG. 2D shows an isometric view of a multi-function drive mechanism, according to at least one embodiment of the present invention at a later stage during activation.
Figure 2E:
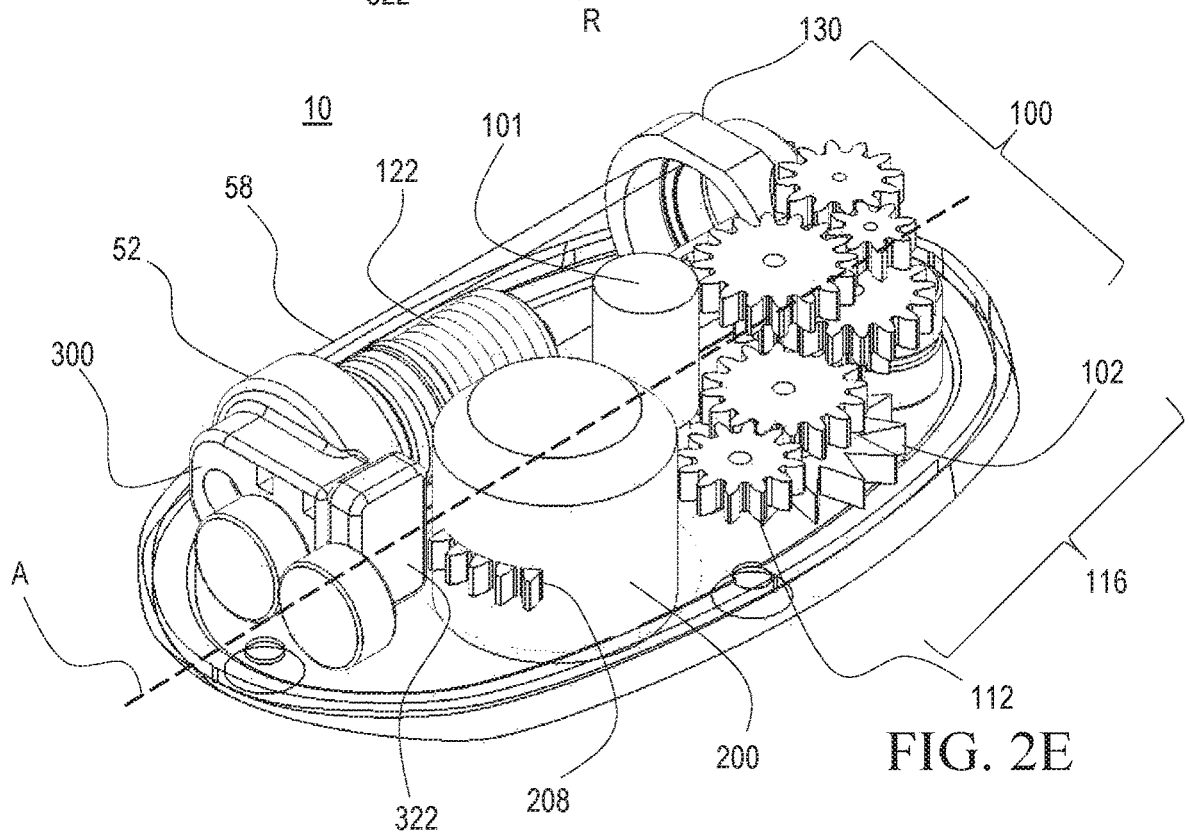
FIG. 2E shows an isometric view of a multi-function drive mechanism, according to at least one embodiment of the present invention near or at completion of drug delivery.
Figure 3A:
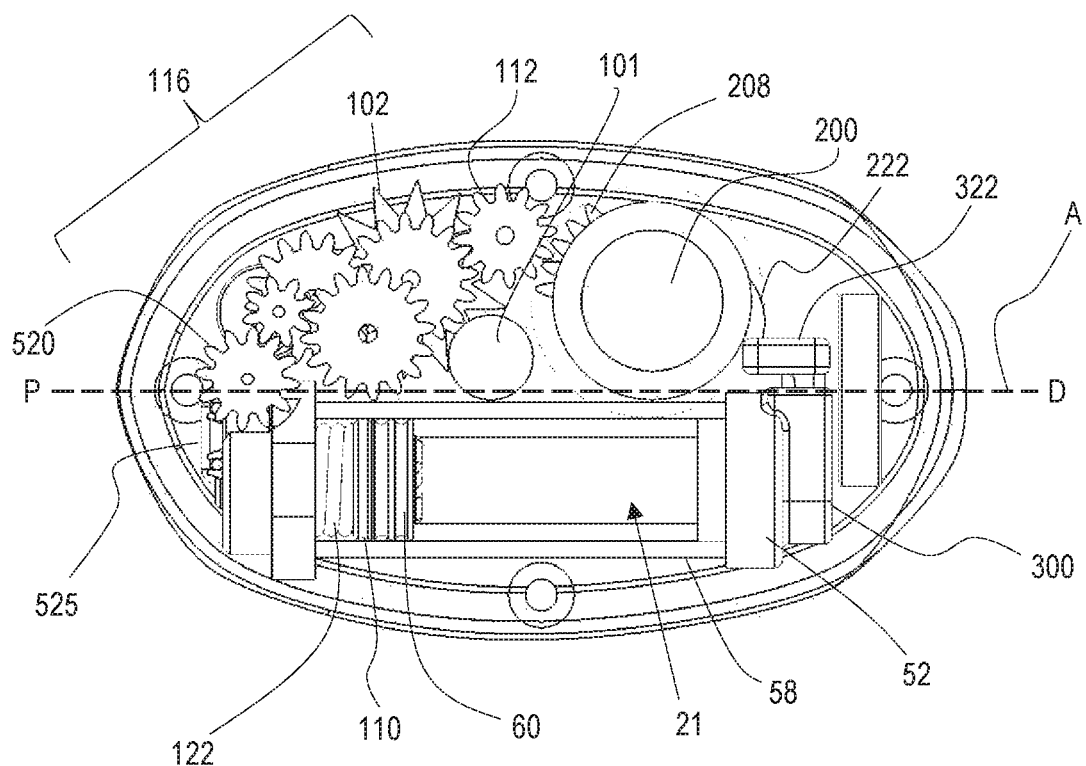
FIGS. 3A-3D show top views which correspond with the stages of operation shown in FIGS. 2B-2E, respectively.
Figure 3B:
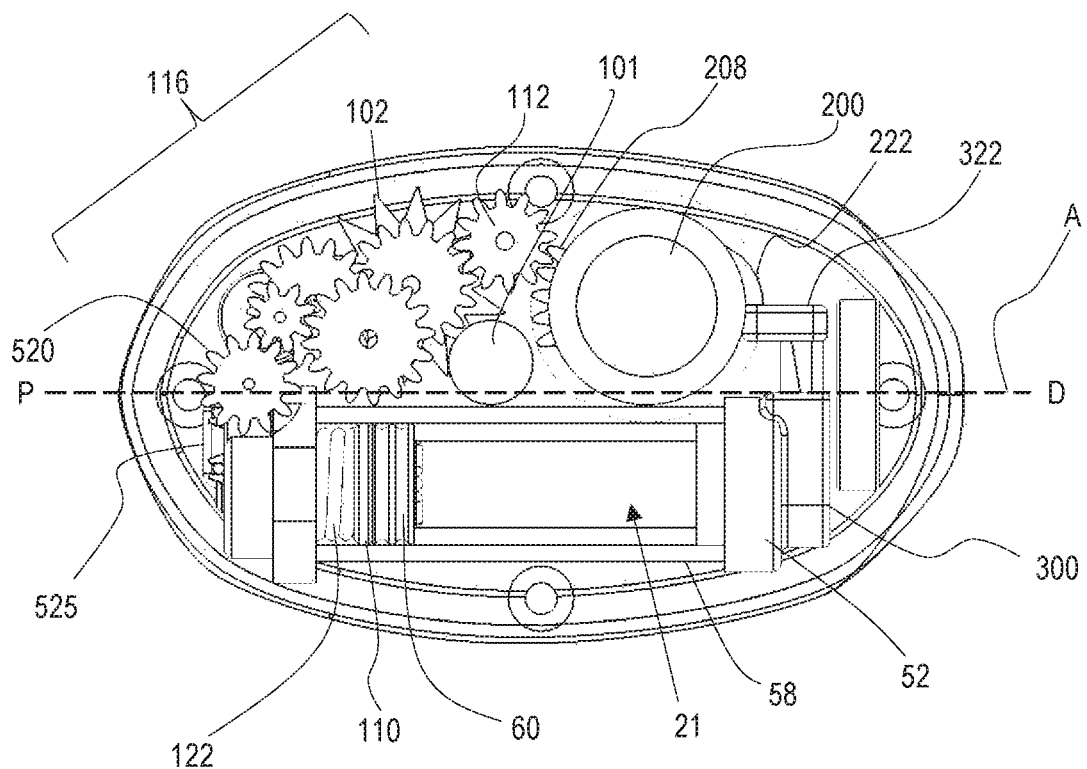
Figure 3C:
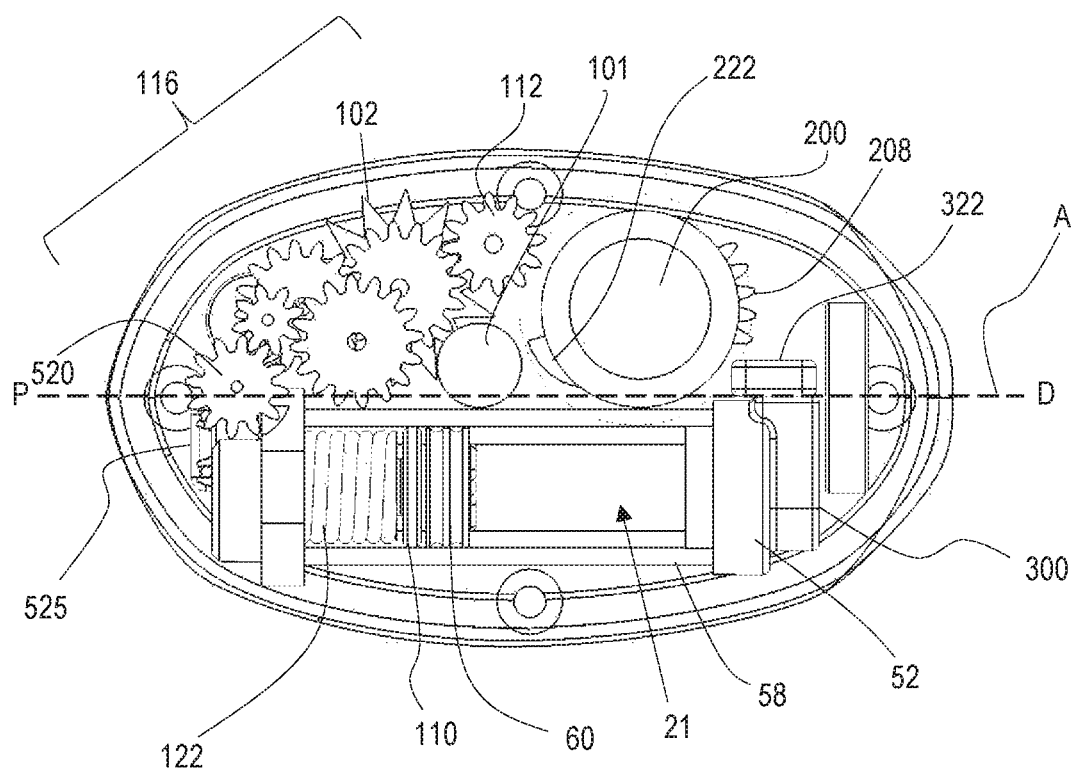
Figure 3D:
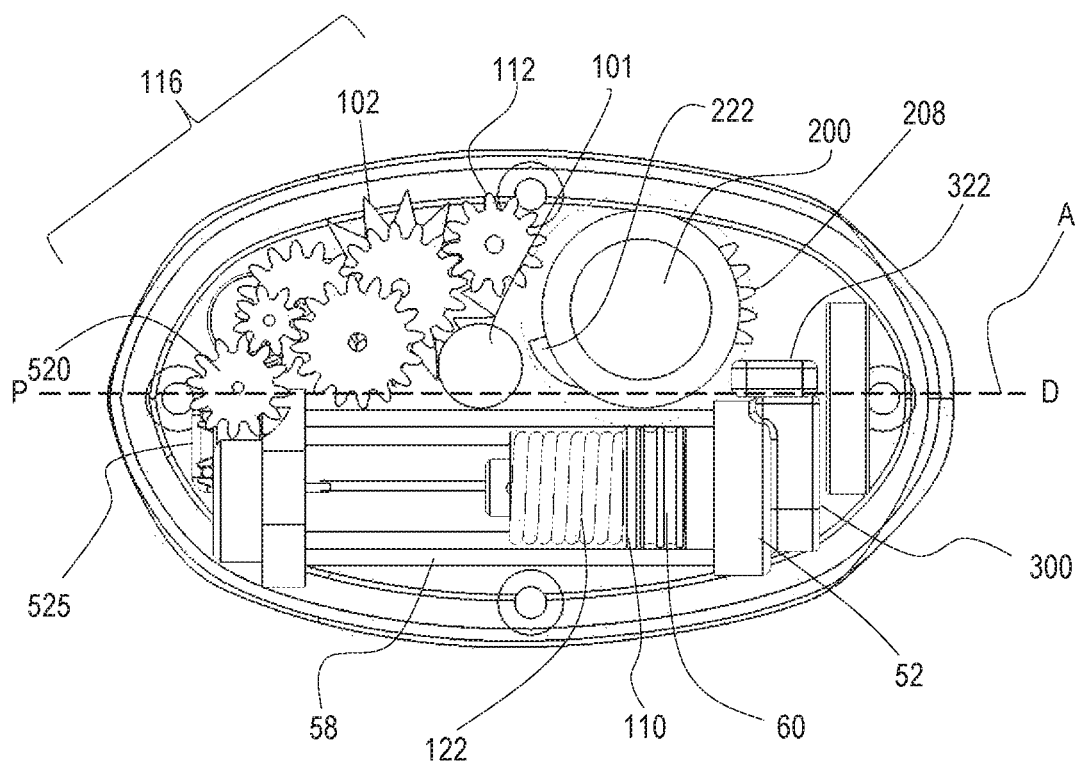

As best shown in FIG. 2D and FIG. 3D, the piston 110 may be comprised of two components and have an interface surface to contact the plunger seal 60.

Moreover, a tether, ribbon, string, or other retention strap (referred to herein as the "tether" 525) may be connected at one end to the piston 110. For example, the tether 525 may be connected to the piston 110 by retention between the two components of the piston 110 when assembled. The tether 525 is connected at another end to a winch drum/gear 520 (including a winch drum 520B and a winch gear 520A) of regulating control mechanism 500. Through the use of the winch drum/gear 520 connected to one end of the tether 525, and the tether 525 connected at another end to the piston 110, the regulating mechanism 500 functions to control, meter, provide resistance, or otherwise prevent free axial translation of the piston 110 and plunger seal 60 utilized to force a drug substance out of a drug container 50.

Accordingly, the power and control system 800 may control the regulating sub-system or mechanism 500 which may be a portion of the gear assembly 116 aspect of the multi-function drive mechanism, and which together may function to control the rate or profile of drug delivery to the user.

With reference to FIG. 8C, the power and control system, via the drive control system 820, may control the regulating mechanism 500 (e.g., via the drive control mechanism 100). For example, the control unit 810 may drive the actuator or motor 101 to drive the gear assembly (e.g., gear assembly 516) of the regulating mechanism 500, by selecting appropriate configurations for the motor 101 and the gear assembly. Moreover, the driving of the regulating mechanism may be time-controlled, as discussed herein.

Figure 4:
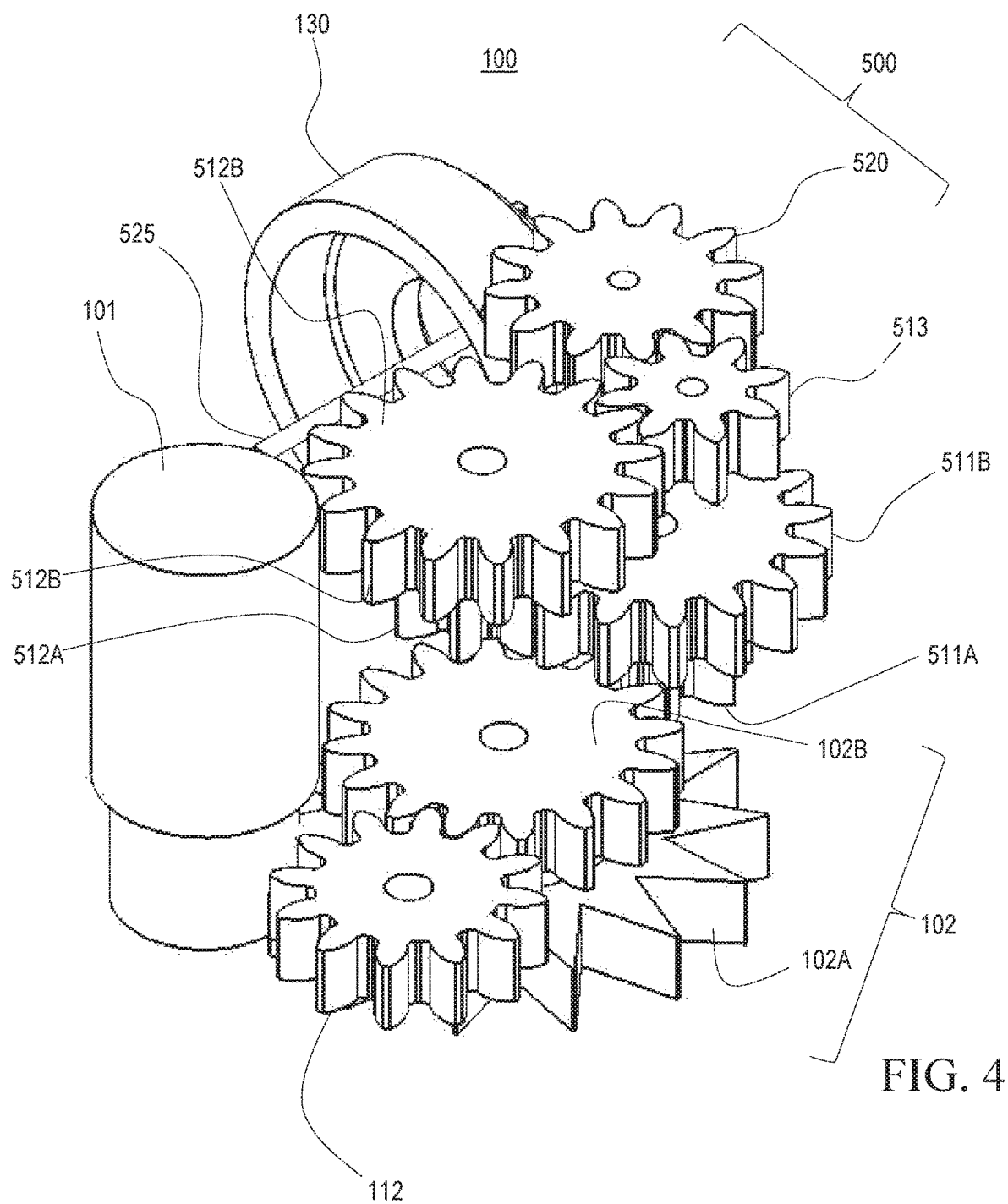
FIG. 4 shows the multi-function drive mechanism, according to at least one embodiment of the present invention, in isolation from the drug delivery device.
Figure 5A:
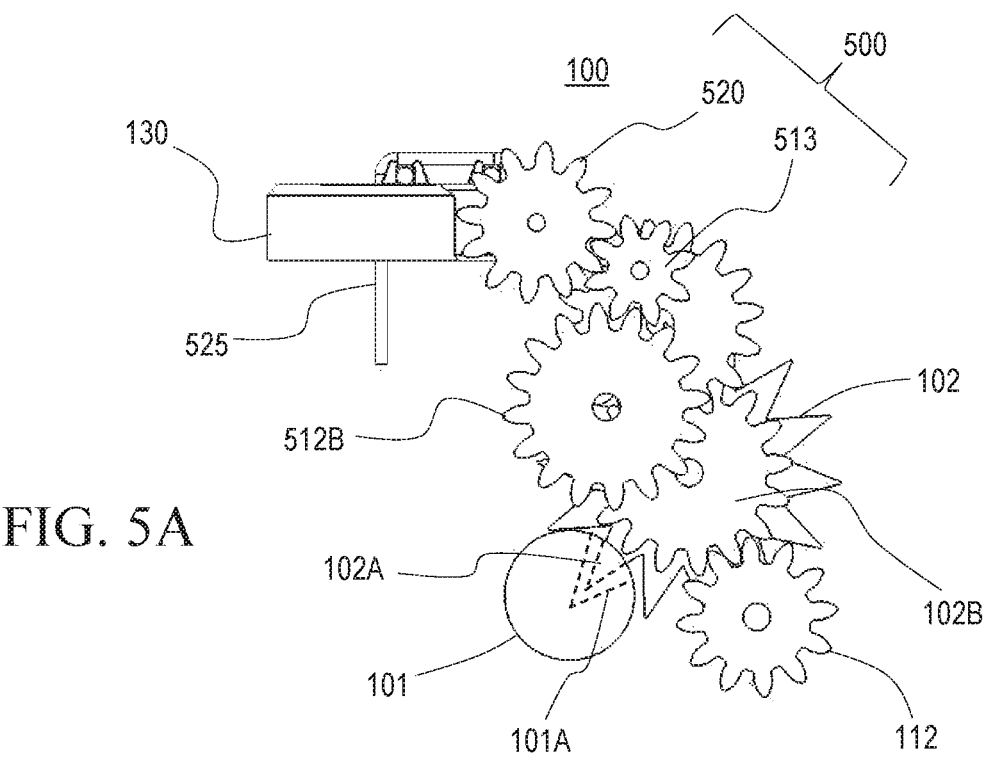
FIGS. 5A-5B show top and bottom views, respectively, of the multi-function drive mechanism shown in FIG. 4.
Figure 5B:
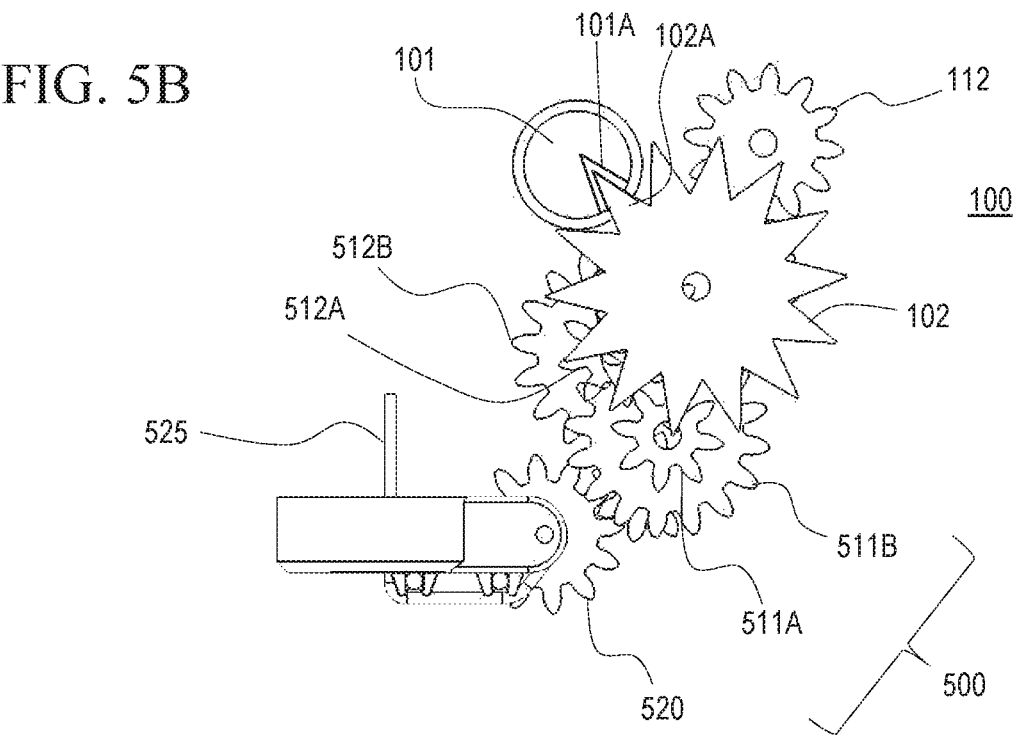
Figure 5C:
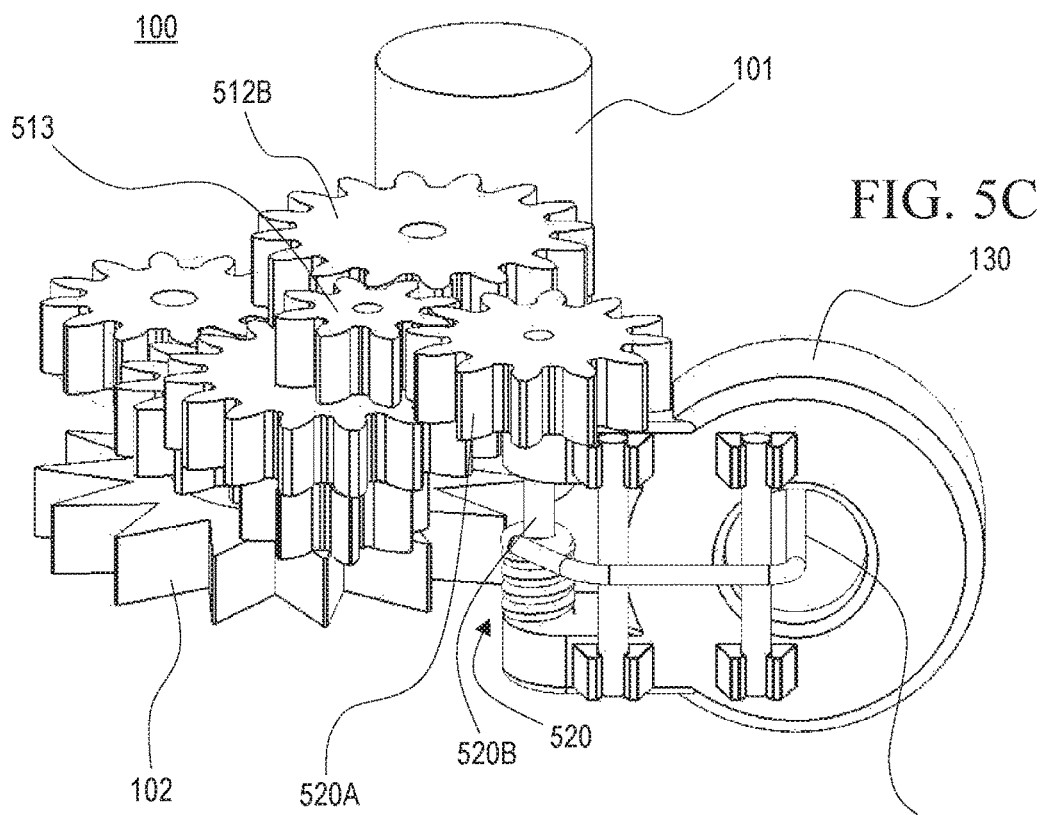
FIGS. 5C-5D show front and back perspective views, respectively, of the multi-function drive mechanism shown in FIG. 4.
Figure 5D:
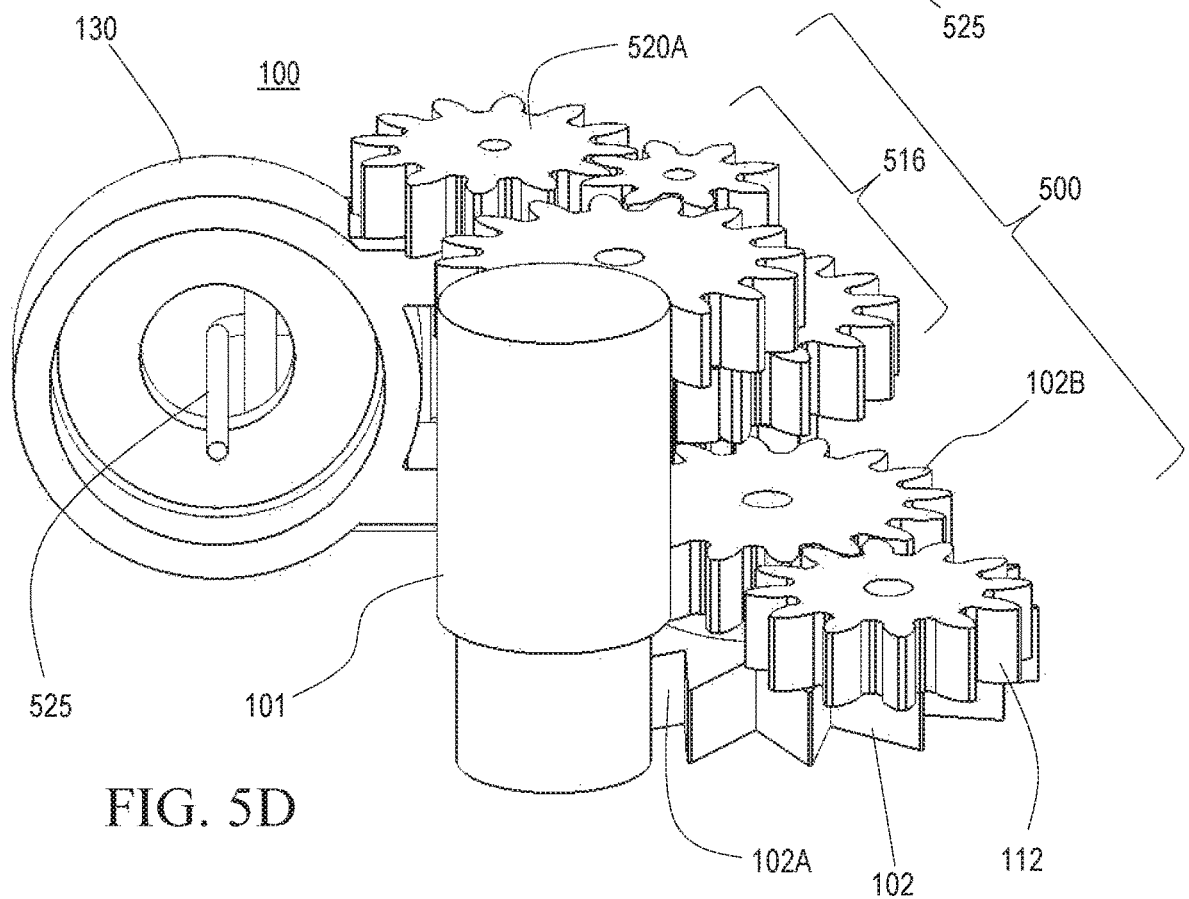

As shown in FIGS. 2A-2D and 3A-3D, and in isolation in FIGS. 4 and 5A-5B, in the embodiments of the present disclosure, the regulating mechanism 500 is a gear assembly driven by an actuator 101. Moreover, upon receiving command signals from the control unit 810, the motor 101 may control the regulating mechanism 500 to retard or restrain the distribution of tether 525, thus allowing the tether 525 to advance at a regulated or desired rate. This restricts movement of piston 110 within barrel 58, which is pushed by one or more biasing members 122, hence controlling the movement of plunger seal 60 and delivery of the drug contained in chamber 21. As the plunger seal 60 advances in the drug container 50, the drug substance is dispensed through the sterile pathway connection 300, conduit, insertion mechanism 200, and into the body of the user for drug delivery. In one example, the regulated motion of the tether 525 may be monitored by an optional tether sensor 875 which may provide status feedback to the control unit 810 of the power and control system 800. The control unit 810 may process the feedback status information of the regulated motion of the tether 525 to further control the regulating mechanism 500.

As discussed above, in at least one embodiment, the motor 101 may be a Pac-Man motor that has a gear interface within which one or more teeth of the main gear may partially reside during operation of the drug delivery pump device 10. The operation of the Pac-Man motor may be controlled by the control unit 810 (see FIGS. 5A-5B).

In one example, when the gear interface 101A of the Pac-Man motor 101 is in alignment with a tooth 102A of the main gear 102, rotational motion of the Pac-Man motor 101 causes gear interface rotation of the main gear 102. When the Pac-Man motor 101 is between gear teeth of the main gear, it may act as a resistance for, for example, back-spinning or unwinding of the gear assembly 116. In one particular embodiment, the Pac-Man motor 101 utilizes an alternating direction type motor to rotate the Pac-Man motor 101 backwards and forwards. This configuration aids in the prevention of a runaway condition, where the motor and the gears are freely permitted to rotate, by using the multi-direction of the motor to prevent continuous spin in one direction (as would be needed for a runaway condition). This bi-directional movement of the motor, coupled with the use of the gear interface cut within the Pac-Man motor, may provide suitable safety features to prevent a runaway condition that could potentially lead to over-delivery of drug to the user. Further detail about the gear assembly 116, regulating mechanism 500, and multi-function drive mechanism 100 are provided herein. In a particular embodiment shown in FIGS. 5A-5B, the regulating mechanism 500 further includes one or more gears 511, 512, 513, 514, of a gear assembly 516. One or more of the gears 511, 512, 513, 514 may be, for example, compound gears having a small diameter gear attached at a shared center point to a large diameter gear. Gear 513 may be rotationally coupled to winch drum/gear 520, for example by a keyed shaft, thereby coupling rotation of gear assembly 516 to winch drum/gear 520. Compound gear 512 engages the small diameter gear 513 such that rotational movement of the compound gear aspect 512B is conveyed by engagement of the gears (such as by engagement of corresponding gear teeth) to gear 513. Compound gear aspect 512A, the rotation of which is coupled to gear aspect 512B, is caused to rotate by action of compound gear aspect 102B of the main/star gear 102. Compound gear aspect 102B, the rotation of which is coupled to main/star gear 102, is caused to rotate by interaction between main/star gear 102A and interface 101A of the actuator 101. Thus, rotation of main/star gear 102 is conveyed to winch drum/gear 520. Accordingly, rotation of the gear assembly 516 initiated by the actuator 101 (of the drive control system 820) may be coupled to winch drum/gear 520 (i.e., through the gear assembly 516), thereby controlling the distribution of tether 525, and the rate of movement of plunger seal 60 within barrel 58 to force a fluid from drug chamber 21. The rotational movement of the winch drum/gear 520, and thus the axial translation of the piston 110 and plunger seal 60, are metered, restrained, or otherwise prevented from free axial translation by other components of the regulating element 500, as described herein. As described above, the actuator 101 may be a number of known power/motion sources including, for example, a motor (e.g., a DC motor, AC motor, or stepper motor) or a solenoid (e.g., linear solenoid, rotary solenoid).

Figure 7B:
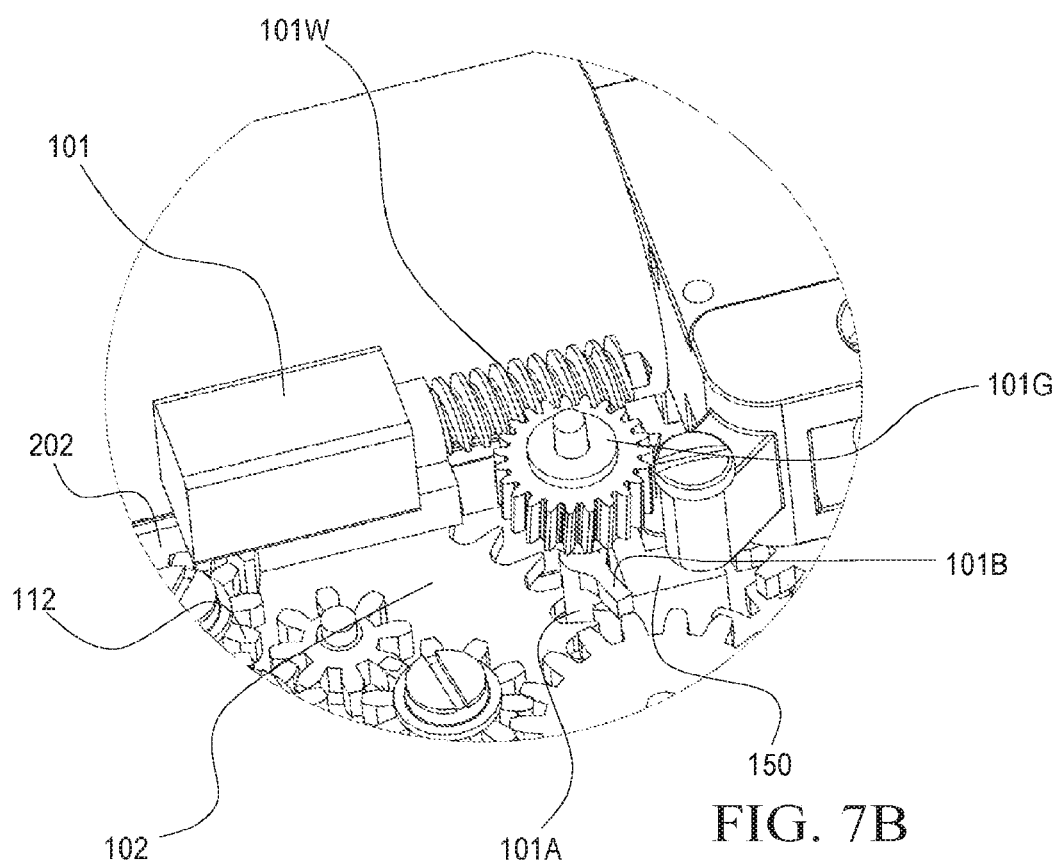
FIG. 7B shows an enlarged view of the drive mechanism shown in FIG. 7A.

As discussed above, the embodiments shown in FIGS. 7A-7B show an actuator 101 that is driven by the control unit 810, and is in horizontal alignment and indirect engagement with the main/star gear 102. Such an embodiment may utilize a rack and pinion engagement, a drive screw, or a worm gear 101W, as shown in FIGS. 7A-7B, to change the direction of motion from horizontal to vertical (i.e., perpendicular interaction). Actuator 101 (based on command signals received from the control unit 810) rotates worm gear 101W, which engages gear 101G and conveys the motion to the Pac-Man gear 101A. The Pac-Man gear 101A engages main/star gear 102 to enable operation of the drive mechanism and the drug delivery device, as described herein.

The control unit 810 controls main star gear 102 via the motor 101. The main star gear 102 may then drive the gear assembly. For example, main/star gear 102 may drive operation of gear 112 to enable operation of the needle insertion mechanism 200, as described herein.

In one embodiment, the control unit 810 provides command signals such that the actuator 101 rotate the worm gear 101W, gear 101G, and Pac-Man gear 101A backwards and forwards. This configuration aids in the prevention of a runaway condition, where the motor and the gears are freely permitted to rotate, by using the multi-direction of the motor to prevent continuous spin in one direction (as would be needed for a runaway condition). This bi-directional movement of the actuator 101, coupled with the use of the gear interface of the worm gear 101W, gear 101G, and Pac-Man gear 101A with the main/star gear 102, provide suitable safety features to prevent a runaway condition that could potentially lead to over-delivery of drug to the user.

Additionally, the motor 101 may include a stop member 101B that stops the rotation of the Pac-Man gear 101A against a stop block 150. Stop block 150 further prevents over-rotation of the Pac-Man gear 101A and, accordingly, the main/star gear 102 to prevent a runaway condition that could potentially lead to over-delivery of drug to the user. For the device to function in this configuration, the Pac-Man gear 101A must be rotated backwards the other direction before rotating forwards again to progress the main/star gear 102 because the stop member 101B prevents over rotation in one direction by interaction with the stop block 150.

Additionally, the geometry of worm gear 101W may be configured such that it is self-locking and/or cannot be back-driven by gear 101G. This may be done by configuration of parameters such as: pitch, lead angle, pressure angle, and number of threads. In so doing, runaway conditions of the drive mechanism will be prevented by the worm gear's resistance to rotations that are not caused by actuator 101. Alternatively or additionally, the control unit 810 may be configured to determine whether there is any feedback from the worm gear 101W that is caused by the rotations of other gears (e.g., gear 101G) and not by the motor 101. If the control unit 810 determines or receives such feedback, the control unit 810 may terminate further operations.

It is noted that, the power and control system 800 does not control the regulating mechanisms 500 of the present invention to drive the delivery of fluid substances from the drug chamber 21. The delivery of fluid substances from the drug chamber 21 is caused by the expansion of the biasing member 122 from its initial energized state acting upon the piston 110 and plunger seal 60 (which may be actuated by the control unit 810 via the motor 101). The regulating mechanisms 500 instead function to provide resistance to the free motion of the piston 110 and plunger seal 60 as they are pushed by the expansion of the biasing member 122 from its initial energized state. The regulating mechanism 500 does not drive the delivery but only controls the delivery motion. The tether limits or otherwise restrains the motion of the piston 110 and plunger seal 60, but does not apply the force for the delivery. According to a preferred embodiment, the controlled delivery drive mechanisms and drug pumps of the present invention include a regulating mechanism indirectly or directly connected to a tether metering the axial translation of the piston 110 and plunger seal 60, which are being driven to axially translate by the biasing member 122.

In one example, the power and control system 800 of the drug pump device 10 may be configured to receive one or more regulating parameters for controlling the regulating mechanism 500. Alternatively, or additionally the power and control system 800 may receive sensor inputs (e.g., heart rate sensor, glucose monitor sensor information) and may then translate the sensor inputs into regulating parameters. The control unit 810 may then control the regulating mechanism 500 after a predetermined time (e.g., after the wait time period). Based on the inputs, the control unit 810 may meter the release of the tether 525 by the winch drum/gear 520 and thereby permit axial translation of the piston 110 by the biasing member 122 to translate a plunger seal 60 within a barrel 58.

Based on the regulating parameters, the control unit 810 and motor 101 may additionally control the restraint provided by the tether 525 and winch drum/gear 520 on the free axial translation of the piston 110 upon which the biasing member 122 bears upon via the motor 101. The control unit 810 may control such operations to provide a desired drug delivery rate or profile, to change the dose volume for delivery to the user, and/or to otherwise start, stop, or pause operation of the drive mechanism In one example, the control unit 810 may control the drug delivery rate in order to complete a drug delivery dose within a desired or a predetermined time. In one embodiment, the tether may be released and permitted to unwind unrestrained. This may provide a bolus delivery of the fluid.

During the drug delivery process, and after a predetermined wait time period, the power and control system may provide delivery instructions to the drive control system 820. Based on the instructions, the drive control system may control the components of the drive mechanism 100, to axially translate the plunger seal 60 of the drug container 50 in the distal direction. Optionally, the drive mechanism 100 and/or the regulating mechanism 500 may include one or more compliance features which enable additional axial translation of the plunger seal 60 to, for example, ensure that substantially the entire drug dose has been delivered to the user. For example, the plunger seal 60, itself, may have some compressibility permitting a compliance push of drug fluid from the drug container.

For example, the controlled delivery drive mechanisms and/or drug pumps of the present invention may additionally enable a compliance push to ensure that substantially all of the drug substance has been pushed out of the drug chamber 21. The plunger seal 60, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container. Additionally or alternatively, an electromechanical status switch may be utilized to contact, connect, or otherwise enable a transmission to the control unit 810 of the power and control system 800 to signal end-of-dose to the user. This configuration may further enable true end-of-dose indication to the user.

As discussed with reference to FIG. 8B, the drive control system 820 may include various sensors (e.g., the tether sensor 875, valve sensor 877, pressure sensor 870) that may be coupled to the control unit 810 and/or to the motor 101. The sensors may be configured to provide signal or status information for various elements of the systems and sub-systems of the drug pump device 10. In one example, the control unit 810 may process the feedback signals or the status information received from the sensors to control the sub-systems, such as the regulating sub-system or mechanism 500.

Additionally, the power and control system 800 may provide notification to the user based on the feedback provided by the sensors to the control unit. The notification may be tactile, visual, and/or auditory, as described above, and may be redundant such that more than one signal or type of notification is provided to the user during use of the device. For example, the user may be provided an initial notification to indicate that the drug pump device 10 is operational and ready for drug delivery and may further provide an end-of-dose notification, based on the feedback signal provided, for example, by one or more sensors. In one example, pressure sensor 870 and/or a valve sensor 877, positioned at appropriate location in the drug pump device 10, may sense the end-of-dose when the piston reaches the end of its axial translation. Accordingly, the control unit 810 may then provide an end-of-dose notification based on the sensor signals received from the sensors.

Additionally or alternatively, tether 525 may have one or more sensor triggers such as electrical contacts, optical markings, and/or electromechanical pins or recesses that are configured to provide status feedback to the tether sensors 875, and in turn, to the control unit 820. In at least one embodiment, an end-of-dose status notification may be provided to the user once the tether sensor 875 detects that the final status trigger positioned on the tether 525 has reached a final position upon the end of axial travel of the piston 110 and plunger 60 within the barrel 58 of the drug container 50. The tether sensor 875 may be, for example, an electrical switch reader to contact the corresponding electrical contacts, an optical reader to recognize the corresponding optical markings, or a mechanical or electromechanical reader configured to contact corresponding pins, holes, or similar aspects on the tether 525.

In one example, the status triggers (not shown) may be positioned along the tether 525 to be read or detected at positions which correspond with the beginning and end of drug delivery, as well as at desired increments during drug delivery.

In some examples, the drive control system 820 initiates the drug delivery (upon actuation of the drive mechanism 100) by release of the biasing member 122 and the resulting force applied to the piston 110 and plunger seal 60. The power and control system 800 further instructs the drive control system 820 to control the rate or profile of drug delivery to the user by controlling the regulating mechanism 500, gear assembly 516, winch drum/gear 520, releasing the tether 525 and permitting expansion of the biasing member 122 and axial translation of the piston 110 and plunger seal 60. As this occurs, the status triggers of the tether 525 are contacted or recognized by the tether sensor and the status of the drive mechanism before, during, and after operation can then be relayed to the control unit 810 of the power and control system 800 to provide feedback to the user. Depending on the number of status triggers located on the tether 525, the frequency of the incremental status indication may be varied as desired. As described above, a range of tether sensors may be utilized depending on the status triggers utilized.

In some embodiments, the tether sensor may include one or more sensors of similar type, and/or a combination of different types of sensors. In one example, a tension force may be applied to the tether 525 (e.g., according to one or more command signals from the control unit 810). When the drug pump device 10 reaches the end-of-dose, the tether 525 goes slack which may be detected by a tether sensor 875 such as an electrical or electromechanical switch. The tether sensor 875 may signal a slack in the tether 525 to the control unit 810 of the power and control system 800.

Additionally, gear 511A and/or gear 511B, or any other gear of gear assembly 516 may be configured as an encoder along with a sensor. For example, the sensor/encoder combination 873 may be configured to provide feedback of gear assembly rotation. In one example, the encoder/sensor 873 may be calibrated to an initial position of the piston (e.g., the position of piston 110 when there is no slack in the tether 525). Moreover, this positional information may be recorded or stored in the control unit 810. As such, the control unit 810 or the power and control system 800 may receive positional feedback, end-of-dose signal, and error indication, such as an occlusion, for example, due to a slack in the tether 525 prior to reaching the expected number of motor rotations as counted by the sensor/encoder 873c. Alternatively or additionally, the drive control system 820 may control the rate of flow of drug via the tether 525 in combination with the regulating mechanism 500.

It will be appreciated that, additional and/or alternative means may be implemented for terminating or restraining the flow of the medicament in the case of slack in, or failure of, the tether 525 (e.g., during a breakage of the tether). For example, International Patent Application Publication Number WO 2016/130679, which is incorporated herein by reference, describes a number of such safety mechanisms.

Figure 6A:
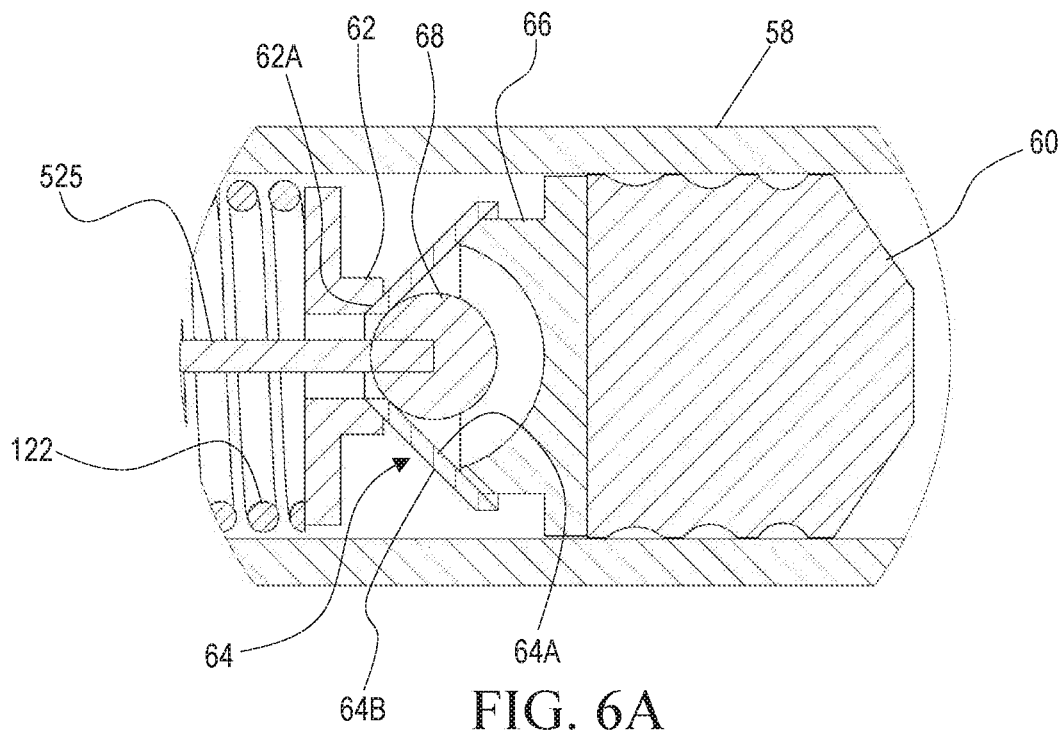
FIG. 6A shows a cross-sectional view of a drug container and safety mechanism in an initial, unrestrained configuration.
Figure 6B:
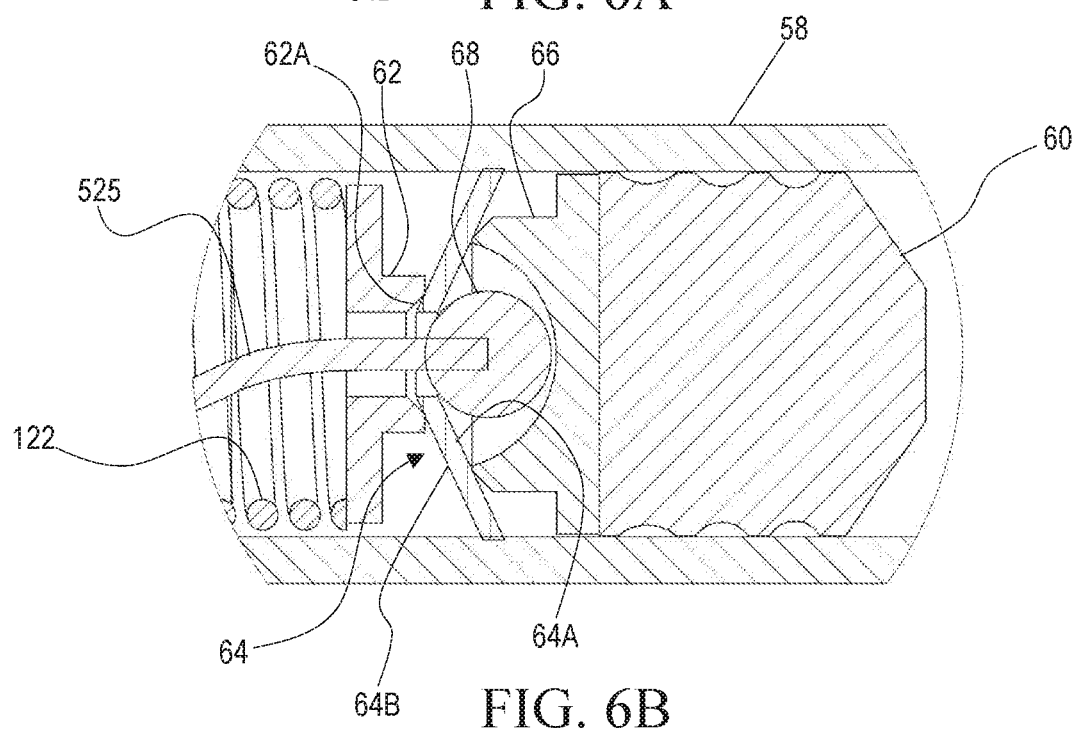
FIG. 6B shows a cross-sectional view of the drug container and safety mechanism of FIG. 6A in an activated configuration.

FIGS. 6A-6B shows one such embodiment for a safety-stop during a failure of the tether 525. Disposed within barrel 58 are brake 64, sleeve 62, and plug 68, and optionally retainer 66. Biasing member 122 bears against sleeve 62. Initially, the tether 525 is engaged with plug 68, thereby allowing tether 525 to restrain the motion of sleeve 62. This restraint controls the rate of expansion or de-energizing of biasing member 122. When tether 525 is under tension, plug 68 bears against distal face 64A of brake 64, causing proximal face 64B of brake 64 to bear against sleeve 62. Due to this contact, and the profile of the distal end 62A of sleeve 62, brake 64 is maintained in a substantially conical configuration as shown in FIG. 6A. In this configuration, expansion or de-energizing of biasing member 122 is restrained. Also, in this conical configuration, the outer diameter of brake 64 is less than the inner diameter of barrel 58, thus translation of the brake is not restrained by contact with the inner wall of the drug container. Also, a portion of brake 64 is in contact with retainer 66. Because brake 64 is maintained in this configuration by plug 68 and sleeve 62, translation of sleeve 62, caused by decompression of biasing member 122, is transferred to retainer 66. Likewise, contact of retainer 66 with plunger seal 60 causes translation of plunger seal 60.

As shown in FIG. 6B, in the event of slack in, or failure of, tether 525, plug 68 is no longer held in position by tether 525 and, therefore, no longer restrains motion of sleeve 62. As biasing member 122 decompresses or de-energizes, brake 64 transforms to a relatively less conical or flatter configuration. This may be caused by a natural bias of brake 64 to transform to this configuration or, alternatively, may be caused by contact of brake 64 with both retainer 66 and sleeve 62. As the brake is transformed, it comes into contact with the inner wall of barrel 58. The brake thus acts as a wedge to restrict translation of sleeve 62. This may prevent further translation or may act to restrict the rate of translation. Optionally, restoring tension in the tether may cause the plug to contact the brake and to transform the brake back to its conical configuration and thus restore normal operation of the drug pump.

FIGS. 6A-6B shows the plug as having a spherical shape and the brake as having a conical shape. Such shapes are used herein merely for exemplary purposes and other shapes or configurations could readily be utilized to achieve the same or similar functionality. For example, the plug may itself be conical in shape and, in one embodiment, be shaped to interface the brake when the brake is in a conical shape. In such a configuration, the conical shape of the plug assists in maintaining the conical shape of the brake, thereby preventing contact between the outer diameter of the brake with the inner diameter of the barrel in order to restrict the axial translation of the sleeve 62 (i.e., applying a braking force). In another embodiment, the brake 64 could employ a star-shaped or other configuration when in a substantially flattened position so as to make contact with the inner diameter of the barrel 58 to prevent or restrict further axial translation of sleeve 62. Without further translation of sleeve 62, biasing member 122 cannot expand or de-energize further which, in turn, prevents or restricts further drug delivery to the user. This provides a necessary and useful safety measure for drug delivery, to prevent over-delivery or accelerated delivery of drug to the user.

Moreover, as discussed above, the control of the tether 525 may be provided by the control unit 810. Additionally, any feedback related to slack or failure of the tether 525 may be provided to the drive control system 820 and/or to the power and control system 800.

As described above, the regulating mechanisms 500 provide resistance to the free motion of the piston 110 and plunger seal 60 as they are pushed by the expansion of the biasing member 122 from its initial energized state. The regulating mechanism 500 may not drive the delivery but may only control the delivery motion.

It is noted that, the tether may limit or restrain the motion of the piston 110 and plunger seal 60, but may not apply the force for the delivery (see FIGS. 2A-2D and 3A-3D). The motion of the piston 110 and plunger seal 60 as they are pushed by the expansion of the biasing member 122 from its initial energized state are shown in the direction of the solid arrow along axis 'A' from proximal or first position 'ID' to the distal or second position 'D', as shown in the transition of FIGS. 2A-2D and 3A-3D.

Control of the tether 525 is further described with reference to FIG. 4 and FIGS. 5A-5B.

FIG. 4 shows a perspective view of the multi-function drive mechanism, according to at least a first embodiment, during its initial locked stage. Initially, the tether 525 may retain the biasing member 122 in an initial energized position within piston 110. When the power and control system 800 receives inputs for activation, it commands the drive control system to initiate the multi-function drive mechanism 100. In one example, the drive mechanism 100 may cause the biasing member to impart a force to piston 110 and therefore to tether 525. This force on tether 525 imparts a torque on winding drum 520 which causes the gear assembly 516 and regulating mechanism 500 to begin motion.

Moreover, as shown in FIG. 3C, the piston 110 and biasing member 122 are both initially in a compressed, energized state behind the plunger seal 60. The biasing member 122 may be maintained in this state until activation of the device between internal features of drive housing 130 and interface surface of piston 110. As the drug pump 10 is activated and the drive mechanism 100 is triggered to operate, biasing member 122 is permitted to expand (i.e., decompress) axially in the distal direction (i.e., in the direction of the solid arrow shown in FIGS. 2A-2D and FIGS. 3A-3D). Such expansion causes the biasing member 122 to act upon and distally translate interface surface and piston 110, thereby distally translating plunger seal 60 to push drug fluid out of the drug chamber 21 of barrel 58.

As discussed above, an end-of-dose status indication may also be provided to the user once one or more sensors contacts or detects the end of axial travel of the piston 110 and plunger seal 60 within the barrel 58 of the drug container 50 (e.g., based on a status trigger positioned on the tether 525). The status triggers may be positioned along the tether 525 at various increments, such as increments which correspond to certain volume measurement, to provide incremental status indication to the user. In at least one embodiment, the sensor is an optical status reader configured to recognize the corresponding optical status triggers on the tether. As would be understood by an ordinarily skilled artisan, such optical status triggers may be markings which are recognizable by the optical status reader. In another embodiment, the status reader is a mechanical or electromechanical reader configured to physically contact corresponding pins, holes, or similar aspects on the tether. Electrical contacts could similarly be utilized on the tether as status triggers which contact or are otherwise recognized by the corresponding electrical sensors. The status triggers may be positioned along the tether 525 to be read or recognized at positions which correspond with the beginning and end of drug delivery, as well as at desired increments during drug delivery. As shown, tether 525 passes substantially axially through the drive mechanism housing 130, the biasing member 122, and connects to the piston 110 to restrict the axial translation of the piston 110 and the plunger seal 60 that resides adjacent thereto. The sensors may communicate the detected information (e.g., the end of dose information, incremental motion, restricted motion, etc.) to the drive control system 820 and/or to the power and control system 800 to notify or provide feedback of the controlled motion of the various components.

As mentioned above various sensors may be coupled directly to the power and control system 800 or via the drive control system 820, and may be configured to provide the incremental status indication. A user may then be notified of such indication based on, for example, the detection of the rotational movement of one or more gears of gear assembly 516. For example, as the gear assembly 516 rotates, a sensor may read or detect one or more corresponding status triggers on one of the gears in the gear assembly to provide incremental status indication before, during, and after operation of the variable rate controlled delivery drive mechanism. A number of sensors may be utilized within the embodiments of the present invention.

In one example, the drive mechanism 100 may utilize an electro-mechanical sensor which may be physically in contact with the gear teeth of one of the gears of the gear assembly. As the sensor is contacted by the status or sensor trigger(s), which in this exemplary embodiment may be the gear teeth of one of the gears (or holes, pins, ridges, markings, electrical contacts, or the like, upon the gear), the sensor measures or detects the rotational position of the gear and transmits a signal to the power and control system 800 for status indication or notification to the user.

Additionally or alternatively, the drive mechanism 100 may utilize an electro-optical sensor. The optical sensor may include a light beam that may be configured detect a motion and transmit a status signal to the power and control system. For example, the optical sensor may be configured to detect motion of the gear teeth of one of the gears in the gear assembly (or holes, pins, ridges, markings, electrical contacts, or the like, upon the gear). In another embodiment, the sensor may be an electrical switch configured to recognize electrical contacts on the gear. In any of these embodiments, the sensor may be utilized to then transmit a signal to the power and control system to provide notification feedback to the user about the controlled motion and/or the delivery of the drug.

As would be appreciated by one having ordinary skill in the art, electro-optical sensors and corresponding triggers, electromechanical sensors and corresponding triggers, and/or electrical or mechanical sensor and corresponding triggers may all be implemented by the embodiments of the present invention to provide incremental status indication to the user power and control system 800. While the drive mechanisms of the present invention are described with reference to the gear assembly and regulating mechanism, a range of configurations may be acceptable and capable of being employed within the embodiments of the present invention, as would readily be appreciated by an ordinarily skilled artisan. Accordingly, the embodiments of the present invention are not limited to the specific gear assembly and regulating mechanism described herein, which is provided as an exemplary embodiment of such mechanisms for employment within the controlled delivery drive mechanisms and drug delivery pumps.

Moreover, in at least one embodiment of the present invention, the delivery profile of the medicament is adjustable. For example, it may be desirable to deliver a bolus injection of medicament before, during, or subsequent to certain activities such as eating, exercising, sleeping, etc. A "bolus injection" is any measured drug volume that is delivered often irrespective of the delivery time or duration. Conversely, a "basal injection" is often a controlled rate of delivery and/or a drug delivery profile having various rates of delivery at different time intervals. Similarly, the user may desire to increase or decrease the basal delivery rate of the medicament at these or other times. In at least one embodiment, the delivery profile may be adjustable by the user to achieve this desired drug delivery. The user may adjust the delivery profile by interacting with the drug delivery device itself or, alternatively, may use an external device, such as a smart-phone, to do so. For example, the user may adjust the delivery profile by displacing the activation mechanism or may engage a separate device-integrated or external delivery control mechanism.

In another embodiment of the present invention, the delivery profile may be adjusted automatically based on one or more inputs. For example, the delivery profile may be adjusted based on the patient's activity level, heart rate, blood sugar level, blood pressure, etc. As above, these measurements may be used to determine the need for a bolus injection or for the increase or decrease of the basal injection delivery rate or adjustment to the basal injection delivery profile. In at least one embodiment, these input measurements may be monitored by the device itself. Additionally, or alternatively, they may be monitored by a secondary device such as a smart-phone, smart watch, heart rate monitor, glucose monitor, blood pressure monitor, or the like. In some embodiments, the delivery profile may be adjusted based on these measurements with no required user intervention. In the case of monitoring and/or control by a secondary device, the secondary device and drug delivery device may be in wireless or wired communication with one another. This communication may be through Bluetooth, near field communication, Wi-Fi, or any other method known to one having ordinary skill in the relevant art of device interconnectivity.

In a preferred embodiment, however, the monitoring/adjustment mechanism may alert and make recommendations to the user and the user may have active control to initiate/authorize or disregard the recommendation made by the monitoring/adjustment mechanism. For example, if one or more of the measurements is above or below a specified threshold value the device may emit an audible, visual, or tactile alert to the user. In one example, the alert is provided by a vibration of the device, thereby providing a discrete alert to the user. Additionally or alternatively, the alert may be provided by the user's smart-phone or other secondary device. The user may be able to view the current status of the measurements in a computer program or web interface on the device itself, a computer, smart-phone, or other device. The computer program or web interface may provide a recommended adjustment to the delivery profile. Based on this information, the user may adjust the delivery rate of the drug delivery device. As above, the user may adjust the delivery profile by displacing the activation mechanism or engaging a separate device-integrated or external delivery control mechanism.

In one embodiment, in response to a signal to adjust the delivery profile, either based on user input or based on the measurements described above, the power and control system may cause a change in the rate of movement of actuator 101. The change in the rate of movement of actuator 101 causes a change in the rotation rate of regulating mechanism 500 which, in turn, controls the rate of drug delivery to the user. Alternatively, the delivery profile may be altered by a change in the characteristics of the flow path of medicament through the conduit connecting the drug container and insertion mechanism. The change may be caused by the introduction, removal, or modification of a flow restrictor which restricts flow of medicament from the drug container to the insertion mechanism. For example, a flow restrictor may have multiple flow paths which may be selectively placed in fluid communication with an input and an output of the flow restrictor. By providing flow paths which are of different length or cross-section the rate of delivery may be controlled. In other embodiments, the delivery profile may be altered by the introduction or removal of an impingement of the conduit. An impingement of the flow path may interrupt or slow flow of medicament through the conduit, thereby controlling the rate of delivery to the user. Accordingly, one or more embodiments of the present invention are capable of producing a change to the rate of medicament delivery from the drug container thereby providing a dynamic control capability to the multi-function drive mechanism and/or the drug delivery device.

Figure 9A:
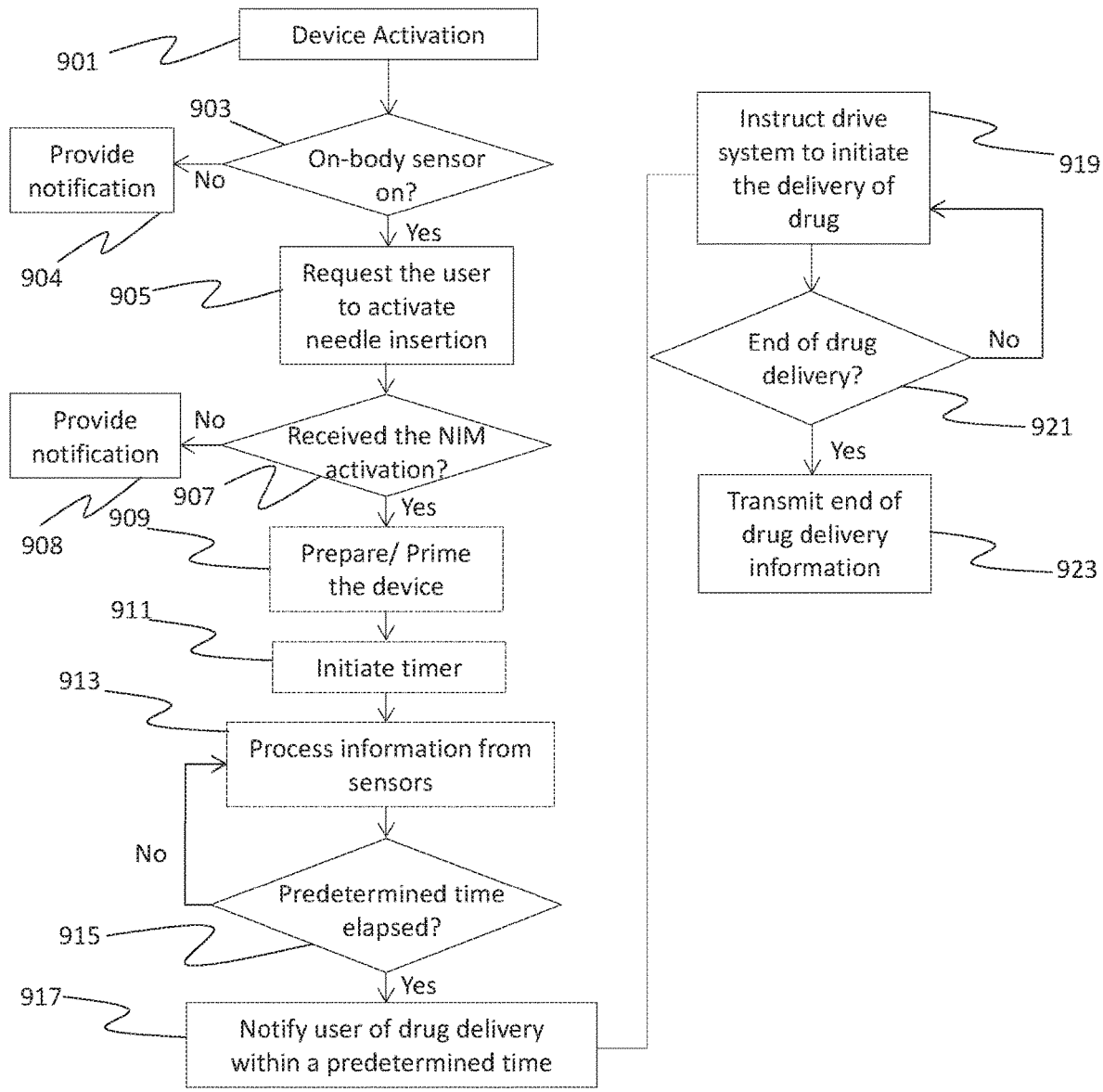
FIGS. 9A-9C are flow-charts of embodiments describing methods of drug delivery by the drug delivery device based on one or more mechanisms.

Details of an exemplary method associated with drug delivery in a predetermined time are now provided with references to FIG. 9A. One or more steps of the method 900 may be executed during active power mode or non-active power mode of the power and control system 800. The method 900, for example, includes steps related to initiating and delivering drug at an adjusted rate to a user by a drug pump device 10 after a predetermined wait time period. The method may include steps of communication between the drug pump device 10 and a mobile device 11. The method may optionally monitor and receive information (e.g., heart rate of the user, glucose/insulin information, etc.) related to the health of the patient during the monitoring period. Particularly, the method requests a user of the drug pump device 10 to activate the needle insertion (i.e., initiate NIM 200), after the device has been activated. Upon activation, by the user, of the needle insertion mechanism, a status switch may be activated, indicating to the power and control system that needle insertion has been completed. When the needle insertion has been actuated, the drug pump device 10 may then initiate a timer to track delay time period. Alternatively, a timer may be initiated by the activation of the device.

Furthermore, the method determines whether the predetermined wait time period has elapsed, and based on the determination may notify the user accordingly about the initiation of the drug delivery process. Optionally, the power and control system may regulate the delivery rate of the drug based on information received from sensors (e.g., temperature sensor, heart rate sensor, glucose monitor sensor). Regulation of the delivery rate may be based on optimization of the effectiveness of the drug. Alternatively, or additionally, the delivery rate may be regulated to reduce and/or minimize the user's discomfort. For example, delivery of a relatively cold drug may cause pain to the user. Hence, if the temperature sensor provides a signal to the control unit that the drug and/or drug container is low, the delivery rate may be reduced.

The method may further determine whether the drug delivery has ended, and based on the determination, in one example may further transmit the end of drug delivery information to the mobile device or cause an audible or visual indication to be emitted from the drug delivery device. The mobile device may further provide the received information to a remote server (e.g., a cloud server). Other parameters may be regulated based on the inputs from the sensors. For example, the delay between activation of an end-of-dose sensor and notification, to the user, that drug delivery has completed. The viscosity of the drug may be dependent on the temperature of the drug and a more viscous drug may require additional time to be fully delivered to the user. Hence, the control unit may use the input from the temperature sensor to determine how long to delay notification to the user of completion of delivery. The control unit may, for example, compare the input from the temperature sensor to a look-up table which is either stored locally or is accessed remotely. Alternatively, the control unit may use the input from the temperature sensor as an input in an equation used to calculate the delay.

Referring now to FIG. 9A, the process flows depicted are merely embodiments of the invention and are not intended to limit the scope of the invention. For example, the steps recited in any of the method or process descriptions may be executed in any order and are not limited to the order presented. Furthermore, it will be appreciated that the following description makes appropriate references not only to the steps depicted in FIG. 9A, but also to the various system components as described with reference to the present invention.

Referring now to FIG. 9A, at step 901, the pump device 10 is activated. The drug pump device 10 may be configured with an activation mechanism that may include receiving a trigger signal from the user to power the power and control system 800. In one example, a user may activate the drug pump device 10 by pressing a start button that may be an on/off switch, and/or a toggle switch. The activation button or the switch may be located through the pump housing 12, such as through an aperture between upper housing and lower housing, and which contacts either directly or indirectly the power and control system 800 (e.g., a via electrical contacts). The user may press the activation button or the switch a predetermined number of times (e.g., one single press) to initially activate the drug pump device 10. Alternatively, pump device 10 may be activated by actuation of an on-body sensor. For example, pump device 10 may include a mechanical or electrical on-body sensor, such as those described in PCT/US2016/021585. In at least one embodiment, actuation of the on-body sensor completes a connection to provide power to the power and control system. Alternatively, the pump device 10 may be configured such that it is activated upon removal from a portion of its packaging. The pump device 10 may include one or more packaging status sensors that are configured to detect the removal of the pump device from a portion of the packaging. The packaging status sensor may take any form capable of detecting a removal of the pump device from a portion of the packaging. For example, the packaging status sensor may be in the form of a pin interconnect on the power and control system 800 that is either connected or disconnected when packaged. Removal from the packaging may cause the pin interconnect to change state from connected to disconnected or vice versa. This change of state may cause initiation of the timer. Alternatively, the packaging status sensor may consist of an optical sensor which is configured to detect a change in lighting conditions caused by a removal of the pump device 10 from a portion of the packaging.

In one example, upon receiving the activation input, a short-range wireless communication link may be initiated between the drug pump device 10 and the mobile device 11. In one example, the wireless communication link may be established based on a Bluetooth pairing between the mobile device 11 and the drug pump device 10.

In one example, during and/or upon the activation, the drug pump device 10 may be in a discovery mode, during which the mobile device 11 may discover the drug pump device 10, and establish the wireless communication with the drug pump device 10. Alternatively, the drug pump device 10 may initiate and establish the wireless communication with the mobile device 11 by sending short-burst signals or pings to the mobile device 11.

Upon receiving the activation signal, the pump device 10 may provide notification or feedback to the user to indicate that the device 10 has been activated. For example, notification signals, such as audible tones, and/or visual notification such as LED lights, may be provided by the power and control system 800.

It is contemplated that, in one example, a user may use the mobile device 11 to activate the drug pump device 10. In such an example, prior to activation, the drug pump device 10 may be in communication only mode during which the drug pump device 10 may be configured to establish a communication link with the mobile device 11 (e.g., Bluetooth pairing). Upon establishing the communication link between the two devices, the user may select or press activation/start button 10*b* to activate the drug pump device 10.

In one example, the housing 12 may include one or more status indicators (e.g., light emitting diodes (LEDs) and/or speakers) and windows that may provide indication of the activation of the drug pump device 10. The activation mechanism, the status indicator, the window, and combinations thereof may be provided on the upper housing or the lower housing such as, for example, on a side visible to the user when the drug pump 10 is placed on the body of the user. Housing 12 is described in further detail hereinafter with reference to other components and embodiments of the present invention.

Additionally or alternatively, the drug pump device 10 may push the activation notification to the mobile device 11. In this example, the mobile app 10*a* may cause the mobile device 11 to provide the notification via speakers or LED lights (not shown) of the mobile device 11. Alternatively, the user may select the notification/data button 10*d* to receive the notification of the activation.

When the drug pump device 10 and the mobile device 11 are linked via the short range wireless communication based on the device activation, the mobile device 11 may provide notification and guidance related to the operation of the drug pump device 10. In one example, the mobile device 11 may provide instruction to place the drug pump device 10 on the body of the user.

It is noted that, during the device activation step, the drug pump device 10 may be in the non-active power mode (i.e., the power and control system 800 may be receiving power from the power source and the drive control system 820 (i.e., motor 101) may not be receiving power from the power source).

Optionally, at step 903, if on-body sensor 840 is not used to activate drug pump device 10, after the drug pump device 10 has been activated, the control unit 810 may determine the status of the on-body skin sensor 840. For example, the control unit 810 may monitor signals from the on-body skin sensor 840 and/or the electro-mechanical skin sensor to determine whether the drug pump device 10 is in contact with the user's skin or body. When the control unit 810 determines that the on-body skin sensor 840 is in contact with the skin of the user for a predetermined amount of time (e.g., 2 minutes), the control unit 810 may set a flag to "on". In some embodiments, activation of the needle insertion mechanism is only possible when the on-body sensor flag is "on". This may be the case whether or not on-body sensor 840 is used to activate drug pump device 10.

It will be appreciated that, the status check of the on-body sensor provides safety measure for the drug pump device 10. Specifically, because the control unit 810 monitors the on-body sensor indication signal for substantial amount of time prior to setting the flag to "on", any quick contact (for a few seconds) or touch (e.g., by mistake) between the drug pump device 10 and the skin of the user may be disregarded by the control unit 810 and/or not allow activation of the needle insertion mechanism. Moreover, any subsequent activation button press by the user for various operations of the drug pump device 10 may only be recognized by the control unit, upon determining that the on-body sensor 840 is on.

At step 904, the drug pump device 10 may provide notification to terminate the drug delivery process if the control unit 810 determines that the drug pump device 10 is not in contact with the body of the user for the predetermined amount of time. Additionally or alternatively, the drug pump device 10 may notify the user of the termination of the drug delivery process or to properly position the drug pump device 10 via the mobile app 10*a*.

At step 905, the drug pump device 10 provides a NIM request notification to the user to activate the needle insertion. For example, as described above, the request notification may be provided via audible tones (continuous or variable tones) and/or via LED lights of the drug pump device 10 to press the activation button a predetermined number of times (e.g., two times) to activate the needle insertion. In at least one embodiment, the request notification is only provided if needle insertion is not activated within a given time period. For example, the request notification may initially be provided two minutes after activation of the device. If needle insertion is performed prior to the expiration of this period, no request notification will be provided.

In another example, the request notification may be provided via the mobile device 11 after control unit 810 determines that the "on" status of the on-body skin sensor 840. In that example, the drug pump mobile app 10*a* may cause the mobile device 11 to provide the request notification for activation of the needle insertion. In one example, the mobile device may provide the user with a request notification to press the activation button (e.g., two times) to activate the needle insertion. For example, the request and/or notification may be provided via a text message. In another example, the user may receive an indication of the notification of the request message via the notification button 10*d*. Upon selecting the button 10*d*, the user may be provided with the request notification message.

At step 907, the control unit 810 may determine whether the user has provided the appropriate input for the activation of the needle insertion (e.g., press of the activation button).

At step 908, when the control unit 810 determines that the needle activation has not been activated within a predetermined amount of time, the method may notify the user to terminate the drug delivery process. In such an example, the control unit 810 may wait for the predetermined amount of time, prior to providing the termination notification. Optionally, in such an embodiment, subsequent initiation of needle insertion may be ineffective.

At step 907, the control unit may determine that the user has responded to the request notification by executing the needle insertion activation (e.g., by pressing the activation button according to the request message). For example, activation of needle insertion may cause a NIM status switch to be activated. The NIM status switch may be activated by contact with a portion of the needle insertion mechanism while inserting the needle or cannula into the target. For example, as shown in FIG. 10, extension 610C of NIM retainer 610 may contact status switch 620 as NIM retainer 610 rotates to allow operation of needle insertion mechanism 200. The method then proceeds to step 909.

It is noted that, the user initiated needle insertion activation is beneficial, as this makes the user aware of the activation of the needle insertion into the body of the user and/or initiation of the drug delivery process.

At step 909, the power and control system 800, may prepare or prime the drug pump device 10. In one example, the power and control system 800 may activate the needle insertion mechanism 200, upon receiving user activation at step 907.

Additionally, the power and control system may prime or initiate the SFPC sub-system 300. It is contemplated that, in some embodiments, the SFPC may be initiated when the drug is being delivered (e.g., at step 921), or concurrently with the needle insertion activation. In one example, during the priming of the device, the piston may be controlled to fill the fluid conduit with fluid drug, thereby displacing any air originally present therein.

It is noted that, during the steps 901, 903, 904, 907 and 908 the power and control system may be in non-active power mode (i.e., the drive control system 820 or motor 101 may not be receiving any power from the power source).

At step 911, timer unit 812 may be initiated automatically. For example, the control unit 810 may initialize the timer unit 812 which may start the wait time period. Optionally, the wait time period may be monitored by the mobile device 11. For example, upon the initiation of the timer unit 812, the control unit 810 may communicate the timing information (e.g., when the timer was initiated, the amount of time left before the drug delivery, etc.) to the mobile device 11. The user may receive such timing information via app 11a (e.g., by pressing timer button 10c).

It is noted that, the control unit 810 may access or consult the timer unit 812 to monitor a wait time period or a delay period. The wait time period may correspond to a time period that needs to be elapsed prior to the initiation of the drug delivery. In one example, the wait time period may be pre-programmed in the power and control system 800. In one example, the wait time period may be 27 hours. Alternatively, the wait time period may be any other suitable time period for the drug delivery process.

Moreover, during the wait time period, the drug pump device 10 may be in the non-active power mode or delay mode. In such embodiments, during the wait time period, the drug pump device may intermittently enter a communication mode in which notifications may be provided to the user and the status of the timer may be monitored. In one example, the drug pump device 10 may communicate with the mobile device 11 intermittently during the wait time period. For example, the control unit 810 via the communication unit 830 of the drug pump device 10 may send a status signal (e.g., a ping signal) to the mobile device 11 to indicate that the drug pump device 10 is operational. Additionally, the drug pump device 10 may send information related to timing information (as discussed above) to the mobile device 11. Additionally, or alternatively, during the wait time period drug pump device 10 may intermittently provide a delay mode indicator, such as an audible or visual notification, to the user.

At step 913, the power and control system 800 may monitor sensor signals from the various internal and/or external sensors. For example, the control unit 810 may monitor signals from the temperature sensor 880 to determine the temperature of the drug. In one example, the control unit 810 may process the detected temperature values to determine that the drug has reached predetermined optimal temperature for drug delivery. The drug pump device 10 may send the temperature information of the drug to the mobile device 11, during the wait time period. The mobile device 11 may process such received data to provide further notification to the user during the wait time period. Step 913 may also include the continuous monitoring of the on-body sensor by the control unit. In the event that the on-body sensor indicates to the control system 800 that the pump device 10 is not in contact with the patient's skin, the control system may provide a notification to the user.

Optionally, the control unit 810 may request the mobile device 11 to monitor signals or data from external sensors such as the glucose rate monitor 11b and the heart rate monitor 11a, and further process the captured data.

In one example, based on the request signal from the drug pump device 10, the mobile app 10a may process the data received from the external sensors to determine various operations of the drug delivery process. For example, based on the data received from the external sensors, the mobile app 10a may determine an adjusted drug delivery rate of the drug that may be delivered to the patient.

In one example, a user may work-out during the wait time period, during which, the mobile app 10a may monitor the heart rate of the user by communicating with the heart rate monitor 11a. The mobile app 10a may execute an algorithm to determine and adjust the drug delivery rate based on the change in the heart rate of the user. Additionally, or alternatively, the mobile app 10a may communicate with the glucose rate monitor 11b to determine and adjust the drug delivery rate based on the change in the glucose rate of the user. Accordingly, the mobile app 11a may provide notification and instruction that provides information as to how to deliver the drug at the adjusted rate. In one example, the user may access such information via the notification button 10d. For example, the notification may include the number of times the user needs to press the activation button on the drug pump device 10 to deliver the drug at the adjusted rate. During the drug delivery period, the control unit 810 of drug pump device 10, upon receiving such specified activation signal (e.g., the number of the press of activation button), may consult the storage unit 813 to translate the adjusted delivery rate information into the drive mechanism information (e.g., gear ratio of various gear assemblies, rate of rotation of the motor 101, etc.) in order to deliver the drug at the adjusted delivery rate. For example, the control unit 810 may control the regulating mechanism 500 or the flow-rate control sub-system 825 via the drive control system 820.

Optionally, in another example, the mobile device 11 may wirelessly communicate the adjusted drug delivery rate to the drug pump device 10, and the drug pump device 10 may automatically deliver the drug at the adjusted rate when the predetermined wait time period expires. In that example, the user may not need to press the activation button to adjust the delivery rate of the drug.

Yet in another example, for a bolus delivery of the drug, the drug pump device 10 may not adjust the delivery rate. In that example, the control unit 810 may optionally monitor the temperature of the drug during the wait time period, and deliver the drug to the user after the wait time period elapses. Optionally, after the wait time period has elapsed, drug delivery may be further delayed if the temperature of the drug and/or drug container is below a predefined value. Additionally, the mobile app 11a may provide notification to the user prior to the delivery of the drug.

At step 915, the drug pump device 10 may determine whether the wait time period has elapsed and/or nearing the end of the wait time period. For example, the control unit 810, upon consulting the timer unit 812, may perform the determination.

In one example, the control unit 810 may determine that the wait time period has elapsed and/or nearing the end of the wait time period. The method may then proceed to step 917.

However, if it is determined that the wait time period has not elapsed and/or not near the wait time period (e.g., if the control unit 810 performs the check 4 hours prior to the end of the wait time period), the method goes back to step 913.

In one example, for a bolus delivery process, at step 917, the drug pump device 10 provides notification to the user to indicate that the wait time period has elapsed and/or the end of the wait time period is approaching. The notification may further indicate that the drug delivery will be initiated. For example, as described above, the notification may be provided via audible tones (continuous or variable tones) and/or via LED lights of the drug pump device 10. In another example, the notification may be provided via the mobile device 11. As described above, the mobile device 10 may receive indication signal from the drug pump device 10, or alternatively, may determine that the drug is to be delivered. Accordingly, the mobile device 11 may then provide the appropriate notification to the user.

Figure 9B:
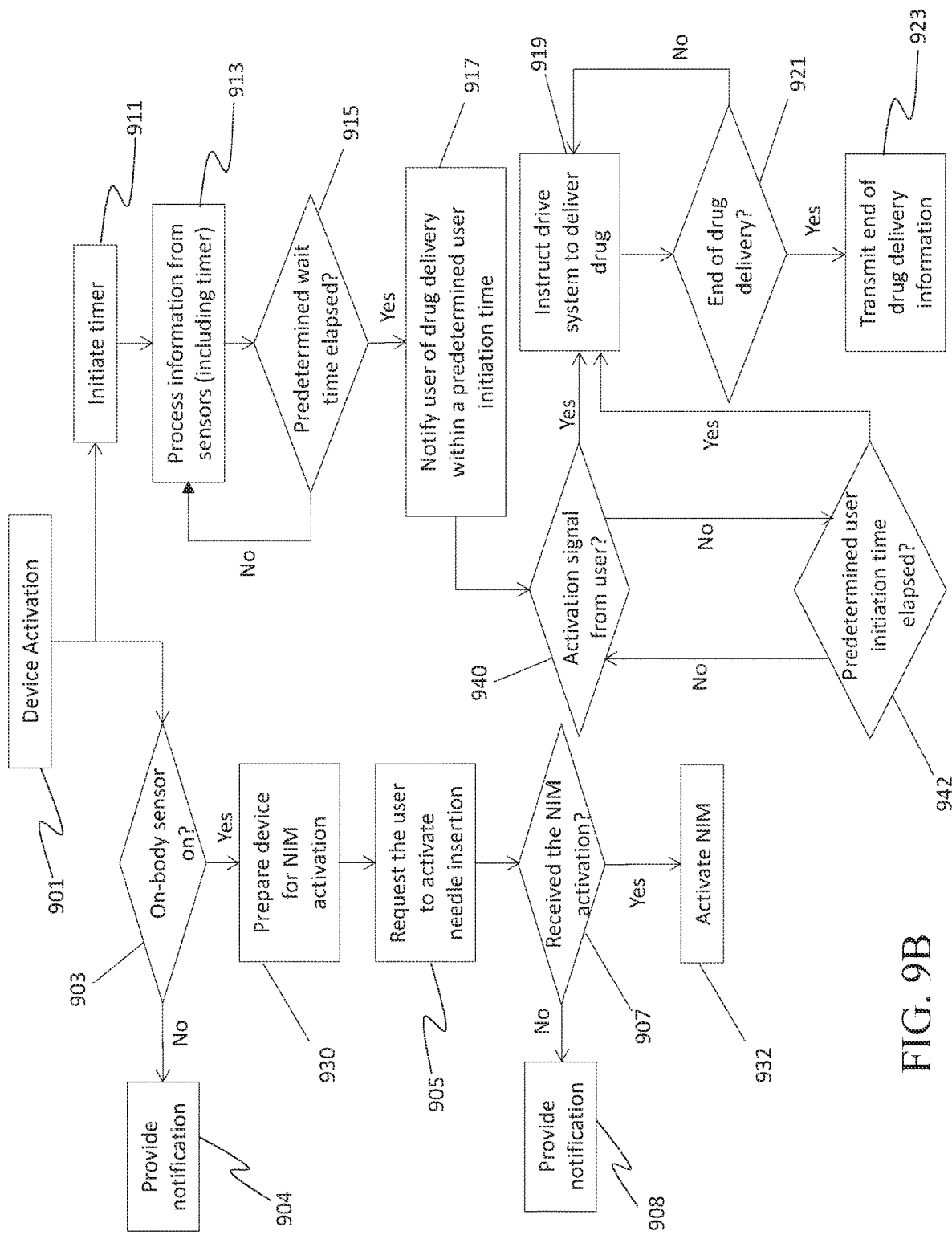

In another example, as shown in FIG. 9B, the drug device may be configured such that the user has the option of initiating drug delivery near to the completion of the wait time, or soon thereafter. In such a scenario, the notification may be provided just before the predetermined time has elapsed (e.g., about 5 minutes before the 27 hour wait period). This may provide the user with sufficient time to prepare and initiate the drug delivery process. For example, the user may be in an office meeting when the predetermined wait time period is about to elapse, and may not be aware of the wait time period. As such, if the user receives the alarm or notification alert prior to end of the wait time period, the user may have sufficient time to step out of the office meeting to initiate the drug delivery, or simply initiate the drug delivery while at the meeting. As shown in FIG. 9B, at step 940 the pump device monitors whether the user has activated delivery of the fluid at step 942. If the user does not activate within the initiation time, the power and control system may automatically initiate delivery.

In another example, the notification may be provided via the pump device 10 or mobile device 11 after or near the wait time period expiration. In that example, the drug pump mobile app 10a may cause the mobile device 11 to provide notification, as described above. In one example, the mobile app 10a may further provide the user with a request message to prepare to initiate the drug delivery (based on the monitored external sensor data). For example, the request and/or notification may be provided via a text message. In another example, the user may receive an indication of the notification of the request message via the notification button 10d. Upon selecting the button 10d, the user may be provided with the request and/or the notification message. Alternatively, or in addition, the pump device may provide notification to the user of the expiration of the wait time period through audible tones, visual indications, or other means.

It is contemplated that, the mobile drug pump app 10a may track the wait time period. For example, the user may select the timer button 10c to gather information such as how much time is left or how much time has elapsed in the wait time period prior to the drug delivery. In some examples, based on the information, the user may terminate the drug delivery process, or send information to the drug pump device 10.

As described above, the notification may further provide instruction related to the delivery of adjusted drug delivery rate to the user. The power and control system 800 may determine if the user has activated the initiation of the drug delivery within a predetermined time. For example, the control unit 810 may determine whether the activation button has been pressed (e.g., within about 2 minutes), after the notification.

If the drug pump device 10 determines that the user has not provided any input to initiate the drug delivery process within the predetermined time at the adjusted rate, the control unit 810 may terminate the drug delivery process. However, if the user provides the input for activation within the predetermined time upon receiving the notification, the method then proceeds to step 919 and enter a delivery mode. In another embodiment, drug pump device 10 automatically proceeds to step 919 at the completion of the predetermined time with or without providing notification to the user. While in the delivery mode, the power and control system may provide one or more delivery mode indicators, such as an audible or visual indicator, to notify the user that delivery of the drug is in progress.

Optionally, as shown in FIG. 9B, the pump device 10 may be configured such that, the user has the option to initiate drug delivery within some predetermined time after completion of the wait time period. If the user does not initiate drug delivery within this predetermined time, the pump device may automatically initiate drug delivery at the expiration of the predetermined time.

At step 919, the power and control system 800 may provide instructions to the drive control system 820 to control the various drive mechanisms of the drug pump device 10 to deliver the drug after the predetermined wait time period.

For example, the control unit of the power and control system 800 may translate the delivery rate information to the settings and configurations for the various components of the drive control system to enable the delivery of the drug according to the determined delivery rate. As described above, the translation may include consulting lookup tables and/or databases stored in the storage units. Alternatively, the power and control system 810 may send the delivery rate information to the drive control system 820, and another controller (not shown) of the drive control system may perform the translation to enable the delivery of the drug according to the determined delivery rate, as described above.

Optionally, at step 919, the power and control system 800 may appropriately change (e.g., increase or decrease) the drug delivery rate, based on the processed data received from the external sensors (e.g., based on the heart rate and/or the glucose rate information of the user, as described at step 913).

Accordingly, the control unit 810 may instruct the drive control system 820 to initiate the drug delivery process (irrespective of the user activation). The drive control system may then deliver the drug by controlling via the drive mechanism 100.

It is contemplated that, in some examples, the power and control system 800 may instruct the drive control system to initiate the insertion mechanism 200 and create the connection between the drug container and the sterile pathway during the drug delivery, after the predetermined wait time period has elapsed. In such a scenario, the user may provide the input for the NIM activation after the predetermined time has elapsed. In another embodiment, the NIM is activated by the power and control system 800 prior to initiation of drug delivery.

At step 921, the power and control system 810 may determine whether the delivery of the drug has ended. For example, motor 101 may receive signal from the tether sensor 875, a valve sensor 877 and/or pressure sensor 870 that indicates an end-of-dose of the drug. Accordingly, the drive control system 820 may then communicate the end-of-dose information to the control unit 810. The method then proceeds to step 923 to provide an end-of-delivery indicator to the user.

When the drug pump device 10 determines that the drug has been delivered, the power and control system 800 may provide notification via audible tones and/or LED lights as described above. Additionally and/or alternatively, notification of the end-of-dose information may be provided by the drug pump device 10 via the drug pump mobile app 10a.

In one example, the drug pump device 10 may determine that the drug has not been delivered or the end-of-dose did not occur in a predetermined amount of time. In such a case, the drug pump device 10 may provide error notification (e.g., via the LED lights and/or via the drug pump mobile app 10a), and the method may then go back to step 919. Alternatively, the power and control system 800 may terminate drug delivery and/or activate retraction of the NIM if an end-of-dose signal is not received within the expected delivery time.

At step 923, upon the determination that the end-of-dose of the drug has occurred (i.e., the drug has been delivered in a predetermined time and/or according to a desired rate of delivery), the drug pump device 10 may communicate various end-of delivery information to the drug pump mobile app 10a. The mobile app 10a may then cause the mobile device 11 to transmit such information to one or more remote servers or storage 11c of various entities (e.g., healthcare provider, health insurance provider, drug manufacturer, etc.). In one example, data stored in the drug pump app 10a related to the end of delivery information may be transmitted to the cloud server 11c via cellular network interface. Moreover, the end of delivery information may include, but is not limited to, validation of the end-of-dose, total time period of the drug delivery, delivery rate information, etc. In one example, a user may select the button 10d of the mobile app 10a to transfer such information. In one example, the mobile app 10a may be configured to selectively transfer the end of delivery information to the various entities. It is contemplated that, the end of delivery information, and/or any other information related to the drug delivery may not be stored permanently upon transfer of such information to the cloud server 11c.

Figure 9C:
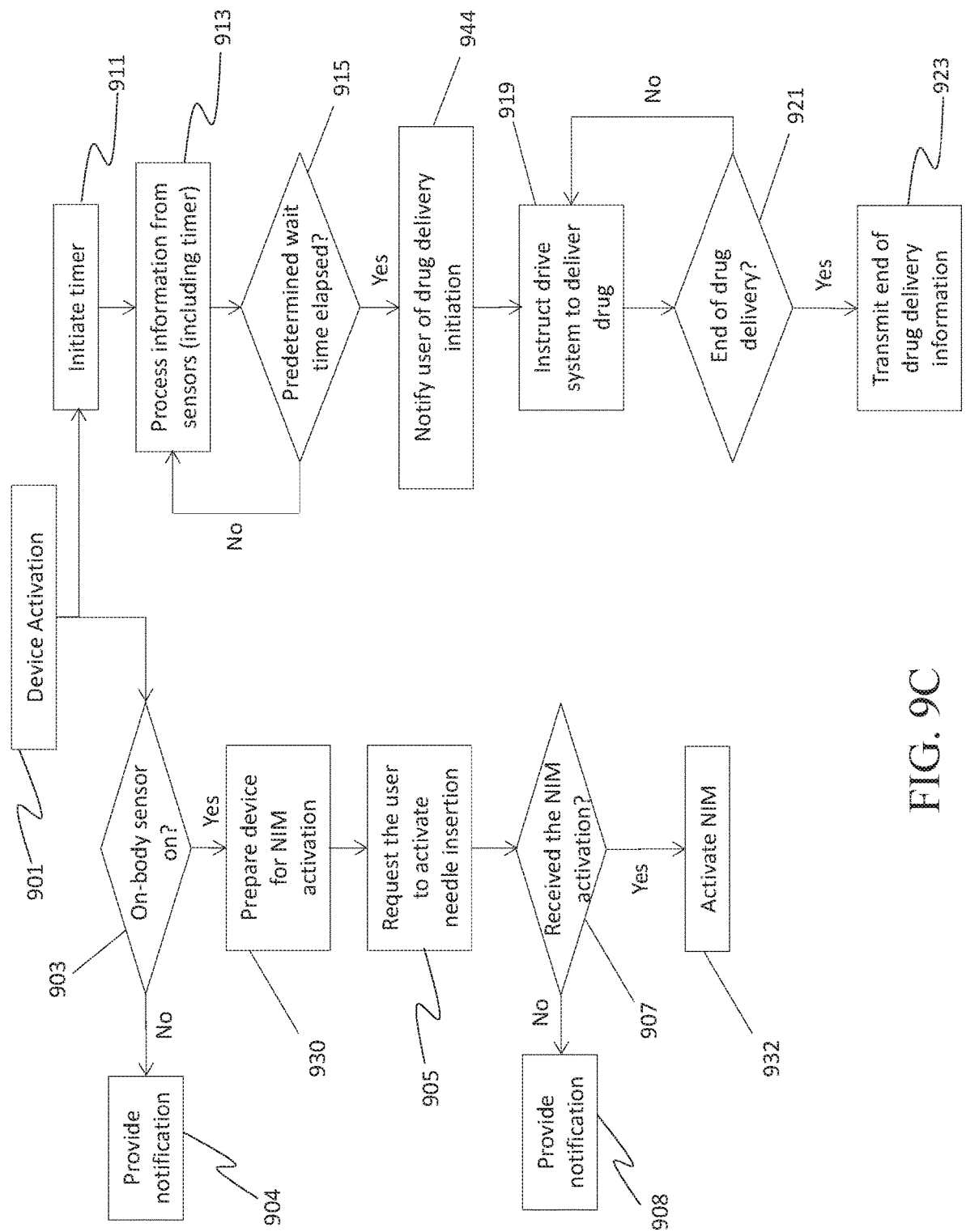

FIGS. 9B and 9C show alternative methods of operation of the pump device 10 and/or mobile device 11. In the methods illustrated in FIGS. 9B and 9C, activation of the device initiates the timer to mark the beginning of the predetermined wait time. Additionally, device activation also initiates the first step in the NIM activation process. As shown in the figures, the first step in the NIM activation process may be to determine if the on-body sensor detects the presence of a target. If the target is detected for the required time period, the device may be prepared for NIM activation, at step 930. The preparation of the device for NIM activation may include configuring one or more of the drive mechanism, regulating mechanism, and actuation mechanism such that the user may activate the NIM. After the device is prepared for NIM activation, the user may be notified to activate the NIM. The notification may be in the form of audible, visual, or tactile feedback from the pump device. Alternatively, or additionally, the notification may be provided by the mobile device.

After notification, the user may activate the NIM to insert the fluid path into the target. For example, the user may activate the NIM by depressing or actuating the actuation mechanism or another mechanism of the pump device. The activation of the NIM may initiate the timer to begin monitoring the predetermined wait time, as described herein.

As shown in FIG. 9B, after the predetermined wait time has elapsed, the user may be notified that the pump device may be activated to begin drug delivery. The user may be able to initiate drug delivery within a predetermined "user initiation time." After the user initiation time has elapsed, the pump device may automatically initiate drug delivery.

The user may, optionally, be notified upon initiation of drug delivery. The notification may in the form of visual, audible, or tactile indication by the pump device or, alternatively, by notification by the mobile device.

In the method shown in FIG. 9C, the pump device 10 is configured such that drug delivery is automatically initiated after the wait time elapses. At step 944, the user may be notified that drug delivery will be, or has been, initiated. The user may be notified by an audible, visual, or tactile notification from the pump device. Alternatively, the user may be notified by the mobile device.

Assembly and/or manufacturing of controlled delivery drive mechanism 100, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the components and devices. Furthermore, known sterilization processes may be employed at one or more of the manufacturing or assembly stages to ensure the sterility of the final product.

The drive mechanism may be assembled in a number of methodologies. In one method of assembly, the drug container 50 may first be assembled and filled with a fluid for delivery to the user. The drug container 50 includes a cap 52, a pierceable seal 56, a barrel 58, and a plunger seal 60. The pierceable seal 56 may be fixedly engaged between the cap 52 and the barrel 58, at a distal end of the barrel 58. The barrel 58 may be filled with a drug fluid through the open proximal end prior to insertion of the plunger seal 60 from the proximal end of the barrel 58. An optional connection mount 54 may be mounted to a distal end of the pierceable seal 56. The connection mount 54 may guide the insertion of the piercing member of the fluid pathway connection into the barrel 58 of the drug container 50. The drug container 50 may then be mounted to a distal end of drive housing 130.

One or more drive biasing members 122 may be inserted into a distal end of the drive housing 130. Optionally, a cover sleeve 140 may be inserted into a distal end of the drive housing 130 to substantially cover biasing member 122. A piston may be inserted into the distal end of the drive housing 130 such that it resides at least partially within an axial pass-through of the biasing member 122 and the biasing member 122 is permitted to contact a piston interface surface of piston 110 at the distal end of the biasing member 122. An optional cover sleeve 140 may be utilized to enclose the biasing member 122 and contact the piston interface surface of piston 110. The piston 110 and drive biasing member 122, and optional cover sleeve 140, may be compressed into drive housing 130. Such assembly positions the drive biasing member 122 in an initial compressed, energized state and preferably places a piston interface surface in contact with the proximal surface of the plunger seal 60 within the proximal end of barrel 58. The piston, piston biasing member, contact sleeve, and optional components, may be compressed and locked into the ready-to-actuate state within the drive housing 130 prior to attachment or mounting of the drug container 50. The tether 525 is pre-connected to the proximal end of the piston 110 and passed through the axial aperture of the biasing member 122 and drive mechanism 130, and then wound through the interior of the drug pump with the other end of the tether 525 wrapped around the winch drum/gear 520 of the regulating mechanism 500.

A fluid pathway connection, and specifically a sterile sleeve of the fluid pathway connection, may be connected to the cap and/or pierceable seal of the drug container. A fluid conduit may be connected to the other end of the fluid pathway connection which itself is connected to the insertion mechanism such that the fluid pathway, when opened, connected, or otherwise enabled travels directly from the drug container, fluid pathway connection, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug pump, as shown in FIG. 1B.

Certain optional standard components or variations of drive mechanism 100 or drug pump 10 are contemplated while remaining within the breadth and scope of the present invention. For example, the embodiments may include one or more batteries utilized to power a motor or solenoid, drive mechanisms, and drug pumps of the present invention. A range of batteries known in the art may be utilized for this purpose. Additionally, upper or lower housings may optionally contain one or more transparent or translucent windows 18 to enable the user to view the operation of the drug pump 10 or verify that drug dose has completed. Similarly, the drug pump 10 may contain an adhesive patch and a patch liner on the bottom surface of the housing 12. The adhesive patch 26 may be utilized to adhere the drug pump 10 to the body of the user for delivery of the drug dose. As would be readily understood by one having ordinary skill in the art, the adhesive patch may have an adhesive surface for adhesion of the drug pump to the body of the user. The adhesive surface of the adhesive patch may initially be covered by a non-adhesive patch liner, which is removed from the adhesive patch prior to placement of the drug pump 10 in contact with the body of the user. Removal of the patch liner may further remove the sealing membrane of the insertion mechanism 200, opening the insertion mechanism to the body of the user for drug delivery (as shown in FIG. 1 C).

Similarly, one or more of the components of controlled delivery drive mechanism 100 and drug pump 10 may be modified while remaining functionally within the breadth and scope of the present invention. For example, as described above, while the housing of drug pump 10 is shown as two separate components upper housing 12A and lower housing 12B, these components may be a single unified component. As discussed above, a glue, adhesive, or other known materials or methods may be utilized to affix one or more components of the controlled delivery drive mechanism and/or drug pump to each other. Alternatively, one or more components of the controlled delivery drive mechanism and/or drug pump may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present invention.

It will be appreciated from the above description that the controlled delivery drive mechanisms and drug pumps disclosed herein provide an efficient and easily-operated system for automated drug delivery from a drug container. The embodiments described herein provide drive mechanisms for the controlled delivery of drug substances and drug delivery pumps which incorporate such controlled delivery drive mechanisms. The drive mechanisms of the present invention control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present invention may provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. The controlled delivery drive mechanisms of the present invention may be directly or indirectly activated by the user. Furthermore, the configurations of the controlled delivery drive mechanism and drug pumps of the present invention maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present invention, the power and control system, the assembly platform, the control arm, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly.

Manufacturing of a drug pump includes the step of attaching both the controlled delivery drive mechanism and drug container, either separately or as a combined component, to an assembly platform or housing of the drug pump. The method of manufacturing further includes attachment of the fluid pathway connection, drug container, and insertion mechanism to the assembly platform or housing. The additional components of the drug pump, as described above, including the power and control system, the activation mechanism, and the control arm may be attached, preformed, or pre-assembled to the assembly platform or housing. An adhesive patch and patch liner may be attached to the housing surface of the drug pump that contacts the user during operation of the device.

A method of operating the drug pump includes the steps of: activating, by a user, the activation mechanism; displacing a control arm to actuate an insertion mechanism; and actuating a power and control system to activate a controlled delivery drive mechanism to drive fluid drug flow through the drug pump according to a controlled rate or drug delivery profile. The method may further include the step of: engaging an optional on-body sensor prior to activating the activation mechanism. The method similarly may include the step of: establishing a connection between a fluid pathway connection to a drug container. Furthermore, the method of operation may include translating a plunger seal within the controlled delivery drive mechanism by the expansion of the biasing member acting upon a piston within a drug container to force fluid drug flow through the drug container, the fluid pathway connection, a sterile fluid conduit, and the insertion mechanism for delivery of the fluid drug to the body of a user, wherein a regulating mechanism acting to restrain the distribution of a tether is utilized to meter the free axial translation of the piston. The method of operation of the drive mechanism and the drug pump may be better appreciated with reference to FIGS. 2A-2D and FIGS. 3A-3D, as described above.

Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

We claim:

1. A drug delivery device comprising:
    a housing;
    a drug container disposed at least partially within the housing and containing a fluid;
    a drive system;
    a power and control system;
    a timer; and
    a needle insertion mechanism adapted for mechanical activation by a user and comprising a mechanical trigger disposed at least partially within the housing and configured to mechanically engage the power and control system;
    wherein the mechanical trigger is configured to activate the needle insertion mechanism to initiate insertion of a cannula into a target and initiate the power and control system to enter a delay mode for a predetermined duration which is monitored by the timer and further wherein at the completion of the predetermined duration the power and control system enters a delivery mode in which the power and control system causes the drive system to initiate delivery of the fluid from the drug container through the needle insertion mechanism and to the target, the mechanical trigger of the needle insertion mechanism mechanically engaging the power and control system after activation of the needle insertion mechanism to activate the power and control system to enter the delay mode.

2. The drug delivery device of claim 1, further comprising a status switch and wherein actuation of the status switch causes the power and control system to enter the delay mode.

3. The drug delivery device of claim 2, wherein the status switch is configured to be actuated by contact with the trigger of the needle insertion mechanism after activation of the needle insertion mechanism.

4. The drug delivery device of claim 3, wherein the needle insertion mechanism is a rotational needle insertion mechanism and rotation of a portion of the needle insertion mechanism causes contact with the status switch.

5. The drug delivery device of claim 1, wherein while in the delay mode the power and control system intermittently enters a communication mode in which the power and control system provides a delay mode indicator.

6. The drug delivery device of claim 5, wherein the delay mode indicator is a visual indication or an audible indication.

7. The drug delivery device of claim 1, wherein the drive system causes a bolus delivery of the fluid.

8. The drug delivery device of claim 1, wherein the power and control system causes activation of an end-of-delivery indicator at completion of delivery of the fluid.

9. The drug delivery device of claim 1, further comprising an on-body sensor, the on-body sensor configured to detect proximity of the drug delivery device to the target, actuation of the on-body sensor causing activation of the power and control system.

10. The drug delivery device of claim 9, wherein the power and control system causes activation of a needle insertion mechanism (NIM) request notification if the needle insertion mechanism is not activated within a predetermined time after activation of the power and control system.

11. The drug delivery device of claim 1, wherein the power and control system causes activation of a delivery mode indicator upon entering the delivery mode.

12. The drug delivery device of claim 11, wherein the delivery mode indicator is a visual indication or an audible indication.

13. A method of operating a drug delivery device comprising:
    initiating insertion of a cannula into a target upon manual activation of a needle insertion mechanism by a user;
    initiating a delay mode of a power and control system, manual activation of the needle insertion mechanism causing a mechanical trigger of the needle insertion mechanism to mechanically engage the power and control system after activation of the needle insertion mechanism to activate the power and control system to enter the delay mode, wherein the mechanical trigger is disposed at least partially within a housing of the drug delivery device;
    entering a delivery mode of the power and control system at the completion of a predetermined duration of the delivery mode; and
    upon entering the delivery mode, activating a drive system to initiate delivery of a fluid from a drug container disposed at least partially within the housing of the drug delivery device, through the needle insertion mechanism and to a target.

14. The method of claim 13, further comprising actuating a status switch.

15. The method of claim 14, wherein the status switch is actuated by contact with the trigger of the needle insertion mechanism.

16. The method of claim 13, further comprising, while in the delay mode, the power and control system intermittently entering a communication mode to provide a delay mode indicator.

17. The method of claim 13, further comprising actuating an on-body sensor to cause activation of the power and control system.

18. The method of claim 13, further comprising the power and control system causing activation of a delivery mode indicator upon entering the delivery mode.

19. The method of claim 13, further comprising the power and control system causing activation of a needle insertion mechanism (NIM) request notification if the needle insertion mechanism is not activated within a predetermined time after activation of the power and control system.

20. The method of claim 13, further comprising the power and control system causing activation of an end-of-delivery indicator at completion of delivery of the fluid.

* * * * *